US009533033B2

(12) United States Patent
Bakaletz et al.

(10) Patent No.: US 9,533,033 B2
(45) **Date of Patent: *Jan. 3, 2017**

(54) ***HAEMOPHILUS INFLUENZAE* TYPE IV PILI**

(71) Applicant: NATIONWIDE CHILDREN'S HOSPITAL, INC., Columbus, OH (US)

(72) Inventors: Lauren O. Bakaletz, Hilliard, OH (US); Robert S. Munson, Jr., Columbus, OH (US)

(73) Assignee: NATIONWIDE CHILDREN'S HOSPITAL, INC., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/062,897

(22) Filed: Mar. 7, 2016

(65) Prior Publication Data

US 2016/0175424 A1 Jun. 23, 2016

Related U.S. Application Data

(60) Continuation of application No. 14/593,401, filed on Jan. 9, 2015, now Pat. No. 9,309,294, which is a division of application No. 13/766,008, filed on Feb. 13, 2013, now abandoned, which is a division of application No. 13/005,166, filed on Jan. 12, 2011, now Pat. No. 8,399,000, which is a continuation of application No. 11/970,273, filed on Jan. 7, 2008, now Pat. No. 7,893,237, which is a continuation of application No. 11/019,005, filed on Dec. 21, 2004, now Pat. No. 7,501,131.

(60) Provisional application No. 60/532,296, filed on Dec. 23, 2003.

(51) Int. Cl.

| | |
|---|---|
| ***A61K 39/102*** | (2006.01) |
| ***A61K 45/00*** | (2006.01) |
| ***A61K 39/02*** | (2006.01) |
| ***C07K 14/285*** | (2006.01) |
| ***C07K 14/195*** | (2006.01) |
| *A61K 39/00* | (2006.01) |

(52) U.S. Cl.

CPC ........... *A61K 39/102* (2013.01); *C07K 14/195* (2013.01); *C07K 14/285* (2013.01); *A61K 39/00* (2013.01); *A61K 2039/505* (2013.01); *C07K 2319/00* (2013.01); *Y10S 435/851* (2013.01)

(58) Field of Classification Search

CPC ...... A61K 38/16; A61K 38/164; A61K 39/00; A61K 39/02; A61K 39/102

USPC ......... 424/184.1, 185.1, 234.1, 242.1, 256.1, 424/278.1

See application file for complete search history.

(56) References Cited

U.S. PATENT DOCUMENTS

| | | | | |
|---|---|---|---|---|
| 6,054,265 | A | 4/2000 | Barney et al. | |
| 6,268,171 | B1 | 7/2001 | Meyer et al. | |
| 6,476,208 | B1 | 11/2002 | Cohen et al. | |
| 6,506,581 | B1 | 1/2003 | Fleischmann et al. | |
| 7,501,131 | B2 | 3/2009 | Bakaletz et al. | |
| 8,399,000 | B2 * | 3/2013 | Bakaletz ............. | C07K 14/195 424/184.1 |
| 9,309,294 | B2 * | 4/2016 | Bakaletz ............. | C07K 14/195 424/184.1 |

FOREIGN PATENT DOCUMENTS

| | | | |
|---|---|---|---|
| WO | WO-96/02648 | A1 | 2/1996 |
| WO | WO-03/078453 | A1 | 9/2003 |

OTHER PUBLICATIONS

Adams et al., Epitope-mapping the immune response of children to otitis media and adults with chronic obstructive pulmonary disease to the PilA protein of the nontypeable *Haemophilus influenza* type IV pilus, Abstract D-158, *American Society for Microbiology*, 107th General Meeting, Toronto, Canada, May 21-27, 2007.

Adams et al., Epitope-mapping the immune response of children to otitis media and adults with chronic obstructive pulmonary disease to the PilA protein of the nontypeable *Haemophilus influenza* type IV pilus, Abstract P53, 9th International Symposium on Recent Advances in Otitis Media, St. Peter Beach, Florida, Jun. 3-7, 2007.

Anderson et al., Human serum activities against *Hemophilus influenzae*, type B, *J. Clin. Invest.*, 51:31-8 (1972).

Bakaletz et al., Evidence for transudation of specific antibody in the middle ears of parenterally immunized chinchillas after an upper respiratory tract infection with adenovirus, *Clin. Diagn. Lab. Immunol.*, 4:223-5 (1997).

Bakaletz et al., Frequency of fimbriation of nontypable *Haemophilus influenzae* and its ability to adhere to chinchilla and human respiratory epithelium, *Infect. Immun.*,56: 331-5 (1988).

(Continued)

*Primary Examiner* — Rodney P Swartz

(74) *Attorney, Agent, or Firm* — Marshall, Gerstein & Borun LLP

(57) ABSTRACT

The invention described herein relates to a *Haemophilus influenzae* (*H. influenzae*) regulon encoding type IV pili. In particular, the invention relates to type IV pili from non-typeable *H. influenzae* (NTHi) and from *H. influenzae* strains a, b, c, e and f. The invention provides isolated *H. influenzae* pilus polynucleotides and polypeptides encoded by the polynucleotides as well as polynucleotides and polypeptides encoded by the polynucleotides involved in the assembly/disassembly of the structure. The invention also relates to uses of these polynucleotides and/or polypeptides including methods for eliciting an immune response to *H. influenzae* and methods of treating and preventing *H. influenzae* related pathological conditions.

9 Claims, 1 Drawing Sheet

(56) References Cited

OTHER PUBLICATIONS

Bakaletz et al., Modeling adenovirus type 1-induced otitis media in the chinchilla: Effect on ciliary activity and fluid transport function of Eustachian tube mucosal epithelium, *J. Infect. Dis.*, 168: 865-72 (1993).
Bakaletz et al., Protection against development of otitis media induced by nontypeable *Haemophilus influenzae* by both active and passive immunization in a chinchilla model of virus-bacterium superinfection, *Infect. Immun.*, 67:2746-62 (1999).
Bakaletz et al., Relative immunogenicity and efficacy of two synthetic chimeric peptides of fimbrin as vaccinogens against nasopharyngeal colonization by nontypeable *Haemophilus influenzae* in the chinchilla, *Vaccine*, 15:955-61 (1997).
Baldwin, Effects of otitis media on child development, *Am. J. Otol.*,14:601-4 (1993).
Bardy, Prokaryotic motility structures, *Microbiology*,149: 295-304 (2003).
Bendler et al., The type b capsulation locus of *Haemophilus influenzae:* Map location and size, *J. Microbiol.*, 70:411-22 (1972).
Berman et al., Theoretical cost effectiveness of management options for children with persisting middle ear effusions, *Pediatrics*, 93(3):353-63 (1994).
Black et al., Efficacy, safety and immunogenicity of heptavalent pneumococcal conjugate vaccine in children, *Pedriatr. Infect. Dis. J.*, 19:187-95 (2000).
Bright et al., The prevalence of tympanostomy tubes in children in the United States, 1988, *Am. J. Public Health*, 83(7):1026-8 (1993).
Chen et al., DNA uptake during bacterial transformation, *Nat. Rev. Microbiol.*, 2(3): 241-9 (2004).
Cimons, Lurid reports obscure reality of strep a outbreaks, *ASM News*, 60:527-30 (1994).
Coleman et al., Chemically defined media for growth of *Haemophilus influenzae* strains, *J. Clin. Micro.*, 41:4408-10 (2003).
Coleman et al., Molecular cloning, expression, and sequence of the pilin gene from nontypeable *Haemophilus influenzae* M37, *Infect. Immun.*, 59(5):1716-22 (1991).
Daines et al., *Haemophilus influenzae* Rd KW20 has virulence properties, *J. Med. Microbiol.*, 52:277-82 (2003).
Darzins et al., Molecular genetic analysis of type-4 pilus biogenesis and twitching motility using *Pseudomonas aeruginosa* as a model system—a review, *Gene*, 192:109-15 (1997).
Demaria et al., Immunization with outer membrane protein P6 from nontypeable *Haemophilus influenzae* induces bactericidal antibody and affords protection in the chinchilla model of otitis media, *Infect. Immun.*, 64:5187-92 (1996).
Dougherty et al., Identification of *Haemophilus influenzae* Rd transformation genes using cassette mutagenesis, *Microbiology*, 145(2):401-9 (1999).
Doughty et al., The type 4 fimbrial subunit gene of *Pasteurella multocida, Vet. Microbiol.*,72:79-90 (2000).
Ehrlich et al., Mucosal biofilm formation on middle-ear mucosa in the chinchilla model of otitis media, *JAMA*, 287(13):1710-5 (2002).
Eskola et al., Efficacy of a pneumococcal conjugate vaccine against acute otitis media, *N. Engl. J. Med.*, 344:403-9 (2001).
Eskola et al., Potential of bacterial vaccines in the prevention of acute otitis media, *Pedriatr. Infect. Dis. J.*,19:S72-8 (2000).
Fleischmann et al., Whole-genome random sequencing and assembly of *Haemophilus influenzae* Rd, *Science*, 269:496-512 (1995).
Friedrich et al., Molecular analyses of the natural transformation machinery and identification of pilus structures in the extremely thermophilic bacterium *Thermus thermophilus* strain HB27, *Appl. Environ. Microbiol.*, 68(2):745-55 (2002).
Friedrich et al., Pilin-like proteins in the extremely thermophilic bacterium *Thermus thermophilus* HB27:Implication in competence for natural transformation and links to type IV pilus biogenesis, *Appl. Environ. Microbiol.*, 69:3695-700 (2003).
Fussenegger et al., Transformation competence and type-4 pilus biogenesis in *Neisseria gonorrhoeae*—a review, *Gene*, 192:125-34 (1997).
Genbank Accession No. U32715, *Haemophilus influenzae* Rd KW20 section 30 of 163 of the complete genome (Aug. 9, 1995).
Gilsdorf et al., Role of pili in *Haemophilus influenzae* adherence and colonization, *Infect. Immun.*, 65:2997-3002 (1997).
Gilsdorf et al., Role of pili in *Haemophilus influenzae* adherence to, and internalization by, respiratory cells, *Pediatr. Res.*, 39:343-8 (1996).
Hill et al., Comparison of the efficacy of a novel chimeric type IV pilus protein-derived vaccine candidate with other candidate immunogens in a nontypeable *Haemophilus influenzae* otitis media superinfection model in the chinchilla, *American Society for Microbiology*, 106th General Meeting, Orlando, Florida, May 21-25, 2006.
Holmes et al., Adherence of non-typeable *Haemophilus influenzae* promotes reorganization of the actin cytoskeleton in human or chinchilla epithelial cells in vitro, *Microb. Pathog.*, 23:157-66 (1997).
Hunter et al., Identification of hearing loss in children with otitis media, *Ann. Otol. Rhinol. Laryngol. Suppl.*,163:59-61 (1994).
Jesaitis et al., Compromised host defense on *Pseudomonas aeruginosa* biofilms: Characterization of neutrophil and biofilm interactions, *J. Immunol.*,171:4329-39 (2003).
Kaplan et al., Overall cost in the treatment of otitis media, *Pediatr. Infect. Dis. J.*,16:S9-11 (1997).
Karudapuram et al., The *Haemophilus influenzae dprABC* Genes Constitute a Competence-Inducible Operon That Requires the Product of the *tfoX*(*sxy*) gene for transcriptional activation, *J. Bacteriology*,179(15):4815-20 (1997).
Keizer et al., Structure of a pilin monomer from *Pseudomonas aeruginosa, J. Biol. Chem.*, 276:24186-93 (2001).
Kennedy et al., Passive transfer of antiserum specific for immunogens derived from a nontypeable *Haemophilus influenzae* adhesin and lipoprotein D prevents otitis media after heterologous challenge, *Infect. Immun.*, 68:2756-65 (2000).
Klausen et al., Biofilm formation by *Pseudomonas aeruginosa* wild type, flagella and type IV pili mutants, *Mol. Microbiol.*,48:1511-24 (2003).
Klausen et al., Involvement of bacterial migration in the development of complex multicellular structures in *Pseudomonas aeruginosa* biofilms, *Mol. Microbiol.*, 50:61-68 (2003).
Klein, Role of nontypeable *Haemophilus influenzae* in pediatric respiratory tract infections, *Pedriatr. Infect. Dis. J.*, 16:S5-8 (1997).
Klein, The burden of otitis media, *Vaccine*, 19(Suppl. 1):S2-S8 (2001).
Kyd et al., Potential of a Novel Protein, OMP26, from Nontypeable *Haemophilus influenzae* to enhance pulmonary clearance in a rat model, *Infect. Immun.*, 66:2272-2278 (1998).
Mason et al., Nontypeable *Haemophilus influenzae* gene expression induced in vivo in a chinchilla model of otitis media, *Infect. Immun.*, 71:3454-3462 (2003).
Mattick, Type IV pili and twitching motility, *Annu. Rev. Microbiol.*,56:289-314 (2002).
McCrea et al., Identification of *hif*D and *hif*E in the Pilus Gene Cluster of *Haemophilus influenzae* Type b Strain Eagan, *Infect. Immun.*, 62: 4922-8.
Merz et al., Pilus retraction powers bacterial twitching motility, *Nature*, 407:98-102 (2000).
Mhlanga-Mutangadura et al., Evolution of the major pilus gene cluster of *Haemophilus influenzae, J. Bacteriol.*, 180(17):4693-4703 (1998).
Microbial-Pathogenesis.org, The genomic sequence of an otitis media isolate of nontypeable *Haemophilus influenzae* (http://www.microbial-pathogenesis.org).
Mudannayake et al., Whole genome analysis of gene expression changes during competence development in *Haemophilus influenzae, Abstracts of the General Meeting of the American Society for Microbiology*, 103:D-001 (2003).

(56) References Cited

OTHER PUBLICATIONS

Novotny et al., Epitope mapping immunodominant regions of the PilA protein of nontypeable *Haemophilus influencae* (NTHI) to facilitate the design of two novel chimeric vaccine canidates. *Vaccine,* 28: 279-89 (2010).
Novotny et al., Epitope mapping of the outer membrane protein P5-homologous fimbrin adhesin of nontypeable *Haemophilus influenzae, Infect. Immunity,* 68(4):2119-2128 (2000).
Novotny et al., Passive immunization with human anti-protein D antibodies induced by polysaccharide protein D conjugates protects chinchillas against otitis media after intranasal challenge with *Haemophilus influenzae, Vaccine,* 24: 4804-11 (2006).
Novotny et al., The fourth surface-exposed region of the outer membrane protein P5-homologous adhesion of nontypable *Haemophilus influenzae* is an immunodominant but nonprotective decoying epitope, *J. Immunol.,* 171:1978-1983 (2003).
O'Toole et al., Flagellar and twitching motility are necessary for *Pseudomonas aeruginosa* biofilm development, *Mol. Microbiol.,* 30:295-304 (1998).
Paap, Management of otitis media with effusion in young children, *Ann. Pharmacother.,* 30(11):1291-1297 (1996).
Perez-Casal et al., Mry, a trans-acting positive regulator of the M protein gene of *Streptococcus pyogenes* with similarity to the receptor proteins of two-component regulatory systems, *J. Bacteriol.,*173:2617-2624 (1991).
Poje et al., in Herbert et al., (Eds.), *Haemophilus influenzae* Protocols, Transformation of *Haemophilus influenzae,* pp. 57-70, Humana Press Inc., Toronto, 2003.
Poolman et al., Developing a nontypeable *Haemophilus influenzae* (NTHi) vaccine, *Vaccine,*19 (Suppl. 1):S108-S115 (2001).
Prymula et al., Pneumococcal capsular polysaccharides conjugated to protein D for prevention of acute otitis media caused by *Streptococcus pneumonia* and non-typable *Haemophilus influenzae:* A randomized double-bind efficacy study, *Lancet,* 367: 740-8 (2006).
Risberg et al., Structural analysis of the lipopolysaccharide oligosaccharide epitopes expressed by a capsule-deficient strain of *Haemophilus influenzae* Rd, *Eur. J. Biochem.,*261:171-180 (1999).
Ruffolo et al., Identification, Purification, and characterization of the type 4 fimbriae of *Pasteurella multocida, Infect. Immun.,* 65:339-343 (1997).
Search Report from European Patent Office for corresponding European application No. EP10153732, mailing date Apr. 26, 2010.
Semmler et al., A re-examination of twitching motility in *Pseudomonas aeruginosa, Microbiology,*145:2863-2873 (1999).
Skerker et al., Direct observation of extension and retraction of type IV pili, *Proc. Natl. Acad. Sci. USA,* 98:6901-6904 (2001).
Snow et al., Progress in the prevention of otitis media through immunization, *Otol. Neurotol.,* 23:1-2 (2002).
Spinola et al., Epidemiology of colonization of nontypable *Haemophilus influenzae* in children: A longitudinal study, *J. Infect. Dis.,* 154:100-9 (1986).
St. Geme III, Molecular and cellular determinants of non-typeable *Haemophilus influenzae* adherence and invasion, *Cell Microbiol.,* 4:191-200 (2002).
Stevenson et al., Cloning and characterisation of type 4 fimbrial genes from *Actinobacillus pleuropneumoniae, Vet. Microbiol.,* 92:121-34 (2003).
Strom et al., Structure-function and biogenesis of the type IV pili, *Annu. Rev. Microbiol.,* 47:565-96 (1993).
Suzuki et al., Synergistic effect of adenovirus type 1 and nontypeable *Haemophilus influenzae* in a chinchilla model of experimental otitis media, *Infect. Immun.,* 62:1710-8 (1994).
Swiss Prot Accession No. P31768, Jul. 1, 1993.
Swiss Prot Accession No. P31769, Jul. 1, 1993.
Swiss Prot Accession No. P31770, Jul. 1, 1993.
Swiss Prot Accession No. P31771, Jul. 1, 1993.
Swiss Prot Accession No. P31772, Jul. 1, 1993.
Swiss Prot Accession No. P31773, Jul. 1, 1993.
Teele et al., Otitis media in infancy and intellectual ability, school achievement, speech, and language at age 7 years, *J. Infect. Dis.,* 162:685-94 (1990).
Tønjum et al., The pilus colonization factor of pathogenic neisserial species: Organelle biogenesis and structure/function relationships—a review, *Gene,* 192:155-63 (1997).
Wall and Kaiser, Type IV pili and cell motility, *Mol. Microbiol.,* 32:1-10 (1999).
Watson et al., Identification of a gene, *pil*F, required for type 4 fimbrial biogenesis and twitching motility in *Pseudomonas aeruginosa, Gene,* 180:49-56 (1996).
Wolfgang et al., Components and dynamics of fiber formation define a ubiquitous biogenesis pathway for bacterial pili, *EMBO J.,* 19:6408-18 (2000).
Zhang et al., Identification of type 4 fimbriae in *Actinobacillus pleuropneumoniae, FEMS Microbiol Lett.,* 189:15-8 (2000).
Zwahlen et al., Participation of complement in host defense against capsule-deficient *Haemophilus influenzae, Infect. Immun.,* 42:708-15 (1983).

* cited by examiner

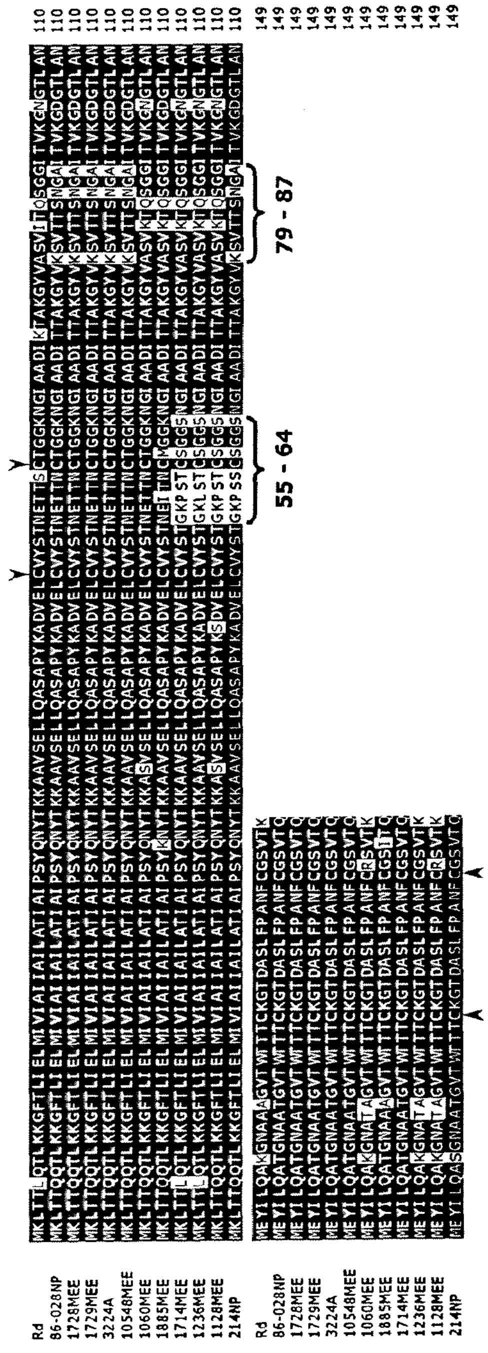
Rd
86-028NP
1728MEE
1729MEE
3224A
10548MEE
1060MEE
1885MEE
1714MEE
1236MEE
1128MEE
214NP
55 - 64
79 - 87
110
149

*HAEMOPHILUS INFLUENZAE* TYPE IV PILI

This application is a continuation of U.S. application Ser. No. 14/593,401, filed Jan. 9, 2015, now U.S. Pat. No. 9,309,294, which is a divisional of U.S. application Ser. No. 13/766,008, filed Feb. 13, 2013, now abandoned, which is a divisional of U.S. application Ser. No. 13/005,166, filed Jan. 12, 2011, now U.S. Pat. No. 8,399,000, which is a continuation of U.S. application Ser. No. 11/970,273, now U.S. Pat. No. 7,893,237, which is a continuation of U.S. application Ser. No. 11/019,005, filed Dec. 21, 2004, now U.S. Pat. No. 7,501,131, which claims priority benefit of U.S. Provisional Patent Application No. 60/532,296, filed Dec. 23, 2003, all of which are incorporated by reference herein in their entirety.

Experimental work relating to the invention described herein was supported by grants R01 DC03915 and R01 DC005980 from the NIH/NIDCD. The United States government may have certain rights in the invention.

FIELD OF INVENTION

The invention described herein relates to a *Haemophilus influenzae* (*H. influenzae*) regulon encoding type IV pili. In particular, the invention relates to type IV pili from non-typeable *H. influenzae* (NTHi) and from *H. influenzae* strains a, b, c, e and f. The invention provides isolated *H. influenzae* pilus polynucleotides and polypeptides encoded by the polynucleotides as well as polynucleotides and polypeptides encoded by the polynucleotides involved in the assembly/disassembly of the structure. The invention also relates to uses of these polynucleotides and/or polypeptides including methods for eliciting an immune response to *H. influenzae* and methods of treating and preventing *H. influenzae* related pathological conditions.

BACKGROUND

The clinical term for middle ear infections is otitis media (OM). According to Klein, *Vaccine,* 19 (Suppl. 1): S2-S8, 2000, OM is the most common reason for an ill child to obtain healthcare and for a child in the United States to receive antibiotics or undergo a general anesthetic. Statistics indicate that 24.5 million physician office visits were made for OM in 1990, representing a greater than 200% increase over those reported in the 1980s. While rarely associated with mortality, the morbidity associated with OM is significant. Hearing loss is a common problem associated with this disease, often affecting a child's behavior, education and development of language skills (Baldwin, *Am. J. Otol.,* 14: 601-604, 1993; Hunter et al., *Ann. Otol. Rhinol. Laryngol. Suppl.,* 163: 59-61, 1994; Teele et al., *J. Infect. Dis.,* 162: 685-694, 1990). The socioeconomic impact of OM is also great, with direct and indirect costs of diagnosing and managing OM exceeding $5 billion annually in the U.S. alone (Kaplan et al., *Pediatr. Infect. Dis. J.,* 16: S9-11, 1997).

OM is thought to result from infectious, environmental and host genetics factors. Bacteria such as *Haemophilus influenzae, Streptococcus pneumoniae* and *Moraxella catarrhalis* are the most common infectious organisms in OM. Acute OM is a disease characterized by rapid onset and short duration of signs and symptoms of inflammation in the middle ear, while chronic OM refers to a condition that is defined by the relatively asymptomatic presence of fluid (or effusion) in the middle ear. However, in chronic OM, despite the absence of certain signs of acute infection (i.e., ear pain or fever), these abnormal middle ear fluids can persist for periods exceeding three months. Treatment of acute OM by antibiotic therapy is common, but antibiotic-resistant bacteria have emerged. Surgical management of chronic OM involves the insertion of tympanostomy tubes through the tympanic membrane of the ear while a child is under general anesthesia. While this procedure is commonplace (prevalence rates are ~13%; Bright et al., *Am. J. Public Health,* 83(7): 1026-8, 1993) and is highly effective in terms of relieving painful symptoms by draining the middle ear of accumulated fluids, it is invasive and carries incumbent risks (Berman et al., *Pediatrics,* 93(3):353-63, 1994; Bright et al., supra.; Cimons, *ASM News,* 60: 527-528; Paap, *Ann. Pharmacother.,* 30(11): 1291-7, 1996). There is thus a need for additional approaches to the management and, preferably, the prevention of OM.

OM vaccine development is most advanced for *S. pneumoniae*, the primary causative agent of acute OM (AOM), as evidenced by the recent approval and release of a seven-valent capsular-conjugate vaccine, PREVNAR® (Eskola and Kilpi, *Pedriatr. Infect. Dis. J.* 16: S72-78, 2000). While PREVNAR® has been highly efficacious for invasive pneumococcal disease, coverage for OM has been disappointing (6-8%) with reports of an increased number of OM cases due to serotypes not included in the vaccine (Black et al., *Pedriatr. Infect. Dis J,* 19: 187-195, 2000; Eskola et al., *Pedriatr. Infect. Dis J.,* 19: S72-78, 2000; Eskola et al., *N. Engl. J. Med.,* 344: 403-409, 2001; Snow et al., *Otol. Neurotol.,* 23: 1-2, 2002).

*H. influenzae* is a gram-negative bacterium that, as noted above, plays a role in OM. Clinical isolates of *H. influenzae* are classified either as serotypes "a" through "f" or as non-typeable depending on the presence or absence, respectively, of type-specific polysaccharide capsules on the bacteria. A vaccine for *H. influenzae* type b has been developed. Like Prevnar®, the type b *H. influenzae* vaccines target the polysaccharide capsule of this organism and thus the vaccine is comprised of capsule polysaccharide that has been conjugated to a protein carrier. Less progress has been made for a vaccine for non-typeable *H. influenzae* (NTHi) which causes approximately 20% of acute OM in children and predominates in chronic OM with effusion (Coleman et al., *Inf and Immunity,* 59(5), 1716-1722, 1991; Klein, *Pedriatr. Infect. Dis J.,* 16, S5-8, 1997; Spinola et al., *J. Infect. Dis.,* 154, 100-109, 1986). NTHi can also cause pneumonia, sinusitis, septicemia, endocarditis, epiglottitis, septic arthritis, meningitis, postpartum and neonatal infections, postpartum and neonatal sepsis, acute and chromic salpingitis, epiglottis, pericardis, cellulitis, osteomyelitis, endocarditis, cholecystitis, intraabdominal infections, urinary tract infection, mastoiditis, aortic graft infection, conjunctivitis, Brazilian purpuric fever, occult bacteremia and exacerbation of underlying lung diseases such as chronic bronchitis, bronchietasis and cystic fibrosis. A prototype NTHi isolate is the low passage isolate 86-028NP which was recovered from a child with chronic OM. This strain has been well characterized in vitro (Bakaletz et al., *Infect. Immun.,* 53: 331-5, 1988; Holmes et al., *Microb. Pathog.,* 23: 157-66, 1997) as well as in a chinchilla OM model (Bakaletz et al., *Vaccine,* 15: 955-61, 1997; Suzuki et al., *Infect. Immun.,* 62: 1710-8, 1994; DeMaria et al., *Infect. Immun.,* 64: 5187-92, 1996). The NTHi strain 86-026NP was deposited with the American Type Culture Collection, 10801 University Blvd., Manassas, Va. 20110, on Oct. 16, 2001 and assigned accession no. PTA-4764. A contig set from the genome of stain 86-028NP can be found at http://www.microbial-pathogenesis.org.

Adherence and colonization are acknowledged first steps in the pathogenesis of *H. influenzae*. As such, *H. influenzae* express multiple adhesions including hemagglutinating pili, fimbriae and non-fimbrial adhesions (Gilsdorf et al., *Pediatr Res* 39, 343-348, 1996; Gilsdorf, *Infect. Immun.,* 65, 2997-3002, 1997; and St. Geme III, *Cell. Microbiol.,* 4, 191-200, 2002). Notably, none of the adhesions described have previously been associated with a motility function. Moreover, *H. influenzae* do not express flagella with are also associated with motility. Twitching motility is a flagella-independent form of bacterial translocation over moist surfaces and occurs by extension, tethering, and then retraction of polar structures known as type IV pili (Bardy, *Microbiology,* 149, 295-304, 2003; Tonjum and Koomey, *Gene,* 192, 155-163, 1997; Wolfgang et al., *EMBO J.,* 19, 6408-6418; Mattick, *Annu. Rev. Microbiol.,* 56, 289-314, 2002). Type IV pili are typically 5-7 nm in diameter, several micrometers in length and comprised of a single protein subunit assembled into a helical conformation with 5 subunits per turn (Bardy et al., *Microbiology,* 149, 295-304, 2003; Wall and Kaiser, *Mol. Microbiol.,* 32, 1-10, 1999). Type IV pilin subunits are usually 145-160 amino acids in length and may be glycosylated or phosphorylated. There are two classes of pilin subunits, type IVa and type IVb, which are distinguished from one another by the average length of the leader peptide and the mature subunit, which N-methylated amino acid occupies the N-terminal position of the mature protein, and the average length of the D-region (for disulfide region). Most of the respiratory pathogens express class IVa pilins, whereas the enteropathogens more typically express class IVb pilins. Type IVa pili are distinguished by the presence of a highly conserved, hydrophobic N-terminal methylated phenylalanine.

Type IV pili serve as a means of rapid colonization of new surfaces. Thus type IV pilus expression is important to both adherence and biofilm formation by many bacteria (Mattick, *Annu. Rev. Microbiol.,* 56, 289-314 2002; O'Toole and Kolter, *Mol. Microbiol.,* 30, 295-304, 1998; Klausen et al., *Mol. Microbiol.,* 50, 61-68, 2003; Jesaitis et al., *J. Immunol.,* 171, 4329-4339, 2003), as well as virulence of *Neisseria* species, *Moraxella bovis, Vibrio cholerae*, enteropathogenic *Escherichia coli* and *Pseudomonas aeruginosa*, among others (O'Toole and Kolter, supra; Klausen et al., supra; Klausen et al., *Mol. Microbiol.,* 48, 1511-1524, 2003; Strom and Lory, *Annu. Rev. Microbiol.,* 47, 565-596, 1993). A biofilm is a complex organization of bacteria that are anchored to a surface via a bacterially extruded exopolysaccharide matrix. The matrix envelopes the bacteria and protects it from the human immune system. Ehrlich et al., *JAMA,* 287(13), 1710-1715 (2002) describes biofilm formation by *H. influenzae*. It has been postulated that blocking the interaction between type IV pili and the human body can avoid or stop the bacterial infection (Meyer et al., U.S. Pat. No. 6,268,171 issued Jul. 31, 2001).

Type IV pilus expression is a complex and highly regulated bacterial function. In *P. aeruginosa*, the biogenesis and function of type IV pili is controlled by over forty genes (Strom and Lory, supra). To date, only a subset of the vast number of related type IV pilus genes (Tonjum and Koomey, supra; Darzins and Russell, *Gene,* 192, 109-115, 1997) have been found in several members of the HAP (*Haemophilus, Actinobacillus* and *Pasteurella*) family (Stevenson et al., *Vet. Microbiol.,* 92, 121-134, 2003; Doughty et al., *Vet. Microbiol.,* 72, 79-90, 2000; Dougherty and Smith, *Microbiology,* 145, 401-409 1999), but neither expression of type IV pili nor twitching motility has ever been described for any *H. influenzae* isolate. In fact, *H. influenzae* is classically described as a bacterium that does not express these structures (Friedrich et al. *Appl. Environ. Microbiol.,* 69, 3695-3700, 2003; Fussenegger et al., *Gene,* 192, 125-134, 1997), despite the presence of a cryptic gene cluster within the strain Rd genome (Fleischmann et al., *Science,* 269, 496-512, 1995). Strain Rd is a non-encapsulated derivative of an *H. influenzae* serotype d organism (Zwahlen et al., *Infect. Immun.,* 42, 708-715, 1983; Bendler and Goodgal, *J. Microbial.,* 70, 411-422, 1972; Risberg et al., *Eur. J. Biochem.,* 261, 171-180, 1999). Although strain Rd has some virulence properties, serotype d strains are generally considered to be commensals; they do not frequently cause disease (Daines et al., *J. Med. Microbiol.,* 52, 277-282, 2003). It is therefore important to make the distinction between disease-causing strains of *H. influenzae* and strain Rd.

SUMMARY OF THE INVENTION

The present invention relates to Type IV pilus gene clusters of *H. influenzae*, in particular non-typeable *H. influenzae* (NTHi) and *H. influenzae* strains a, b, c, e and f.

Polynucleotides and Polypeptides of the Invention

The present invention provides *H. influenzae* polynucleotides and particularly open reading frames from a regulon arranged in two gene clusters plus one other gene. The regulon includes a gene (pilA) that encodes the major subunit of a heretofore uncharacterized *H. influenzae* type IV pilus. The regulon includes polynucleotides from a gene cluster encoding pilin polypeptides PilA (major pilin subunit), PilD (leader peptidase), PilB and PilC (involved in the assembly/disassembly of the pilin structure); another gene cluster encoding ComA, ComB, ComC, ComD, ComE, and ComF (involved in competence for transformation and pilus expression); and a gene encoding PilF (required for type IV pilus biogenesis) (Watson et al, *Gene,* 49: 56, 1996). In one embodiment, the pilus regulon is that of NTHi *H. influenzae* strain 86-028NP.

Polynucleotides encoding the NTHi 86-028NP pilin polypeptides set out in the following SEQ ID NOs are provided by the invention: PilA polypeptide in SEQ ID NO: 2, PilB polypeptide in SEQ ID NO: 4, PilC polypeptide in SEQ ID NO: 6, PilD polypeptide in SEQ ID NO: 8, ComA polypeptide in SEQ ID NO: 10, ComB polypeptide in SEQ ID NO: 12, ComC polypeptide in SEQ ID NO: 14, ComD polypeptide in SEQ ID NO: 16, ComE polypeptide in SEQ ID NO: 18, ComF polypeptide in SEQ ID NO: 20 and PilF polypeptide in SEQ ID NO: 22. Alternative codon usage is thus specifically contemplated by the invention. In one embodiment, the polynucleotides comprise the NTHi 86-028NP gene sequences set out in the following SEQ ID NOs which respectively encode the foregoing polypeptides: pilA in SEQ ID NO: 1, pilB in SEQ ID NO: 3, pilC in SEQ ID NO: 5, pilD in SEQ ID NO: 7, comA in SEQ ID NO: 9, comB in SEQ ID NO: 11, comC in SEQ ID NO: 13, comD in SEQ ID NO: 15, comE in SEQ ID NO: 17, comF in SEQ ID NO: 19; and pilF in SEQ ID NO: 21. Each of the polynucleotide sequences includes a final three nucleotides representing a stop codon.

Also provided are polynucleotides encoding PilA polypeptides from NTHi clinical isolates 1728MEE, 1729MEE, 3224A, 10548MEE, 1060MEE, 1885MEE, 1714MEE, 1236MEE, 1128MEE and 214NP. The amino acid sequences of these PilA polypeptides are set out in SEQ ID NOs: 26, 28, 30, 32, 34, 36, 38, 40, 42 and 44, respectively. Again, the possibility of alternative codon usage is specifically contemplated in polynucleotides encoding the polypeptides. In one embodiment, the polypeptides are respectively encoded by the nucleotide sequences set out in SEQ ID NOs: 25, 27, 29, 31, 33, 35, 37, 39, 41 and 43.

The invention provides for polynucleotides that hybridize under stringent conditions to (a) the complement of the nucleotide sequences set out in SEQ ID NOs: 1, 3, 5, 7, 9, 11, 13, 15, 17, 19, 21, 25, 27, 29, 31, 33, 35, 37, 39, 41 or 43; (b) a polynucleotide which is an allelic variant of any polynucleotides recited above; (c) a polynucleotide which encodes a species homolog of any of the proteins recited above; or (d) a polynucleotide that encodes a polypeptide comprising a specific domain or truncation of the polypeptides of the present invention. Type IV pilin polynucleotides from other non-typeable *H. influenzae* strains and from *H. influenzae* strains a, b, c, e and f are specifically contemplated. These polynucleotides can be identified and isolated by techniques standard in the art such as hybridization and polymerase chain reaction using part or all of the polynucleotides of SEQ ID NOs: 1, 3, 5, 7, 9, 11, 13, 15, 17, 19, 21, 25, 27, 29, 31, 33, 35, 37, 39, 41 or 43 as probes or primers, respectively.

The polynucleotides of the invention also include nucleotide sequences that are substantially equivalent to the polynucleotides recited above. Polynucleotides according to the invention can have, e.g., at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the NTHi polynucleotides recited above.

Included within the scope of the nucleic acid sequences of the invention are nucleic acid sequence fragments that hybridize under stringent conditions to the NTHi nucleotide sequences of SEQ ED NOs: 1, 3, 5, 7, 9, 11, 13, 15, 17, 19, 21, 25, 27, 29, 31, 33, 35, 37, 39, 41 or 43, or complements thereof, which fragment is greater than about 5 nucleotides, preferably 7 nucleotides, more preferably greater than 9 nucleotides and most preferably greater than 17 nucleotides. Fragments of, e.g., 15, 17, or 20 nucleotides or more that are selective for (i.e., specifically hybridize to any one of the polynucleotides of the invention) are contemplated. These nucleic acid sequence fragments capable of specifically hybridizing to a NTHi polynucleotide of the invention can be used as probes to detect NTHi polynucleotides of the invention and/or can differentiate NTHi polynucleotides of the invention from other bacterial genes, and are preferably based on unique nucleotide sequences.

The term "stringent" is used herein to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., *Molecular Cloning: A Laboratory Manual,* 2$^{nd}$ Ed., Cold Spring Harbor Laboratory, (Cold Spring Harbor, N.Y. 1989).

More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

As noted above, polynucleotides contemplated by the present invention are not limited to the specific polynucleotides of SEQ ID NOs: 1, 3, 5, 7, 9, 11, 13, 15, 17, 19, 21, 25, 27, 29, 31, 33, 35, 37, 39, 41 or 43, but also include, for example, allelic and species variations thereof. Allelic and species variations can be routinely determined by comparing the sequence provided in SEQ ID NOs: 1, 3, 5, 7, 9, 11, 13, 15, 17, 19, 21, 25, 27, 29, 31, 33, 35, 37, 39, 41 or 43, preferably the open reading frames therein, a representative fragment thereof, or a nucleotide sequence at least 90% identical, preferably 95% identical, to the open reading frames within SEQ ID NOs: 1, 3, 5, 7, 9, 11, 13, 15, 17, 19, 21, 25, 27, 29, 31, 33, 35, 37, 39, 41 or 43 with a sequence from another isolate of the same species or another species. Preferred computer program methods to determine identity and similarity between two sequences include, but are not limited to, the GCG program package, including GAP (Devereux et al., *Nucl. Acid. Res.,* 12: 387, 1984; Genetics Computer Group, University of Wisconsin, Madison, Wis.), BLASTP, BLASTN, and FASTA (Altschul et al., *J. Mol. Biol.,* 215: 403-410, 1990). The BLASTX program is publicly available from the National Center for Biotechnology Information (NCBI) and other sources (*BLAST Manual*, Altschul et al. NCB/NLM/NIH Bethesda, Md. 20894; Altschul et al., supra). The well known Smith-Waterman algorithm may also be used to determine identity.

Polynucleotides of the invention may be isolated from natural sources or may be synthesized by standard chemical techniques, e.g., the phosphotriester method described in Matteucci et al., *J Am Chem Soc.,* 103: 3185 (1981).

Antisense polynucleotides complementary to the polynucleotides encoding the pilus polypeptides of the invention are also provided.

Polypeptides of the invention include pilin polypeptides PilA, PilD, PilB, PilC, ComA, ComB, ComC, ComD, ComE, ComF and PilF. In one embodiment the polypeptides comprise the NTHi 86-028NP amino acid sequences respectively set out in SEQ ID NO: 2, 4, 6, 8, 10, 12, 14, 16, 18, 20 or 22. Polypeptides of the invention also include PilA polypeptides set out in SEQ ID NOs: 26, 28, 30, 32, 34, 36, 38, 40, 42 or 44. In additional embodiments, the Type IV pilin polypeptides of the invention are those of other non-typeable *H. influenzae* strains and from *H. influenzae* strains a, b, c, e and f.

Polypeptides of the invention specifically include peptide fragments (i.e., peptides) that retain one or more biological or immunogenic properties of a full length polypeptide of the invention. In one embodiment PilA peptide fragments provided by the invention are designated TfpQ2, TFPQ3, TfpQ4 and OLP3 and respectively comprise amino acids 35 through 68 of SEQ ID NO: 2, amino acids 69 through 102 of SEQ ID NO: 2, amino acids 103 through 137 of SEQ ID NO: 2, and amino acids 21 through 35 of SEQ ID NO: 2.

The invention also provides for polypeptides with one or more conservative amino acid substitutions that do not affect the biological and/or immunogenic activity of the polypeptide. Alternatively, the polypeptides of the invention are contemplated to have conservative amino acids substitutions which may or may not alter biological activity. The term "conservative amino acid substitution" refers to a substitution of a native amino acid residue with a nonnative residue, including naturally occurring and nonnaturally occurring amino acids, such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alanine, according to the methods of "alanine scanning mutagenesis". Naturally occurring amino acids are characterized based on their side chains as follows: basic: arginine, lysine, histidine; acidic: glutamic acid, aspartic acid; uncharged polar: glutamine, asparagine, serine, threonine, tyrosine; and non-polar: phenylalanine, tryptophan, cysteine, glycine, alanine, valine, proline, methionine, leucine, norleucine, isoleucine General rules for amino acid substitutions are set forth in Table 1 below.

TABLE 1

| Amino Acid Substitutions | | |
|---|---|---|
| Original Residues | Exemplary Substitutions | Preferred Substitutions |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asn |
| Gly | Pro, Ala | Ala |
| His | Asn, Gln, Lys, Arg | Arg |
| Ile | Leu, Val, Met, Ala, Phe, | Leu |
| Leu | Norleucine, Ile, Val, Met, | Leu |
| Lys | Arg, 1,4 Diaminobutyric | Arg |
| Met | Leu, Phe, Ile | Leu |
| Phe | Leu, Val, Ile, Ala, Tyr | Arg |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, | Leu |

The invention also provides variants of the polypeptides of the present invention (e.g., a polypeptide exhibiting at least about 65%, at least about 70%, at least about 75%, at least about 80%, at least about 85%, 86%, 87%, 88%, 89%, at least about 90%, 91%, 92%, 93%, 94%, typically at least about 95%, 96%, 97%, more typically at least about 98%, or most typically at least about 99% amino acid identity to a polypeptide of SEQ ID NO: 2, 4, 6, 8, 10, 12, 14, 16, 18, 20 or 22) that retain biological and/or immunogenic activity.

The invention contemplates that polynucleotides of the invention may be inserted in a vector for amplification or expression. For expression, the polynucleotides are operatively linked to appropriate expression control sequences such as promoter and polyadenylation signal sequences. Further provided are host cells comprising polynucleotides of the invention. Exemplary prokaryotic host cells include bacteria such as *E. coli, Bacillus, Streptomyces, Pseudomonas, Salmonella* and *Serratia*. Methods of producing polypeptides of the invention by growing the host cells and isolating polypeptide from the host cells or growth medium are specifically contemplated. One or more polynucleotides from the pilus regulon may be expressed in a host cell. For example, expression of the pilA gene alone and expression of multiple polynucleotides from the pilus regulon in order to affect assembly of the native pili structure are both specifically contemplated. Alternatively, polypeptides of the invention can be prepared by chemical synthesis using standard means. Particularly convenient are solid phase techniques (see, e.g., Erikson et al., *The Proteins* (1976) v. 2, Academic Press, New York, p. 255). Automated solid phase synthesizers are commercially available. In addition, modifications in the sequence are easily made by substitution, addition or omission of appropriate residues. For example, a cysteine residue may be added at the carboxy terminus to provide a sulfhydryl group for convenient linkage to a carrier protein, or spacer elements, such as an additional glycine residue, may be incorporated into the sequence between the linking amino acid at the C-terminus and the remainder of the peptide.

The term "isolated" refers to a substance removed from, and essentially free of, the other components of the environment in which it naturally exists. For example, a polypeptide is separated from other cellular proteins or a DNA is separated from other DNA flanking it in a genome in which it naturally occurs.

Antibodies

The invention provides antibodies which bind to antigenic epitopes unique to (i.e., are specific for) *H. influenzae* pilus polypeptides of the invention. Also provided are antibodies which bind to antigenic epitopes common among multiple *H. influenzae* subtypes but unique with respect to any other antigenic epitopes. The antibodies may be polyclonal antibodies, monoclonal antibodies, antibody fragments which retain their ability to bind their unique epitope (e.g., Fv, Fab and F(ab)2 fragments), single chain antibodies and human or humanized antibodies. Antibodies may be generated by techniques standard in the art using pilun polypeptide(s) of the invention or host cells expressing pilin polypeptide(s) of the invention as antigens.

The present invention provides for antibodies specific for the pilin polypeptides of the present invention and fragments thereof, which exhibit the ability to kill both *H. influenzae* bacteria and to protect humans from infection. The present invention also provides for antibodies specific for the polypeptides of the invention which reduce the virulence, inhibit adherence, inhibit biofilm formation, inhibit twitching motility, inhibit cell division, and/or inhibit penetration into the epithelium of *H. influenzae* bacteria and/or enhance phagocytosis of the *H. influenzae* bacteria.

In vitro complement mediated bactericidal assay systems (Musher et al., *Infect. Immun.* 39: 297-304, 1983; Anderson et al., *J. Clin. Invest.* 51: 31-38, 1972) may be used to measure the bactericidal activity of anti-pilus antibodies.

It is also possible to confer short-term protection to a host by passive immunotherapy via the administration of preformed antibody against an *H. influenzae* polypeptide of the invention. Thus, antibodies of the invention may be used in passive immunotherapy. Human immunoglobulin is preferred in human medicine because a heterologous immunoglobulin may provoke an immune response to its foreign immunogenic components. Such passive immunization could be used on an emergency basis for immediate protection of unimmunized individuals subject to special risks.

In another embodiment, antibodies of the invention may be used in the production of anti-idiotypic antibody, which in turn can be used as an antigen to stimulate an immune response against pilin epitopes.

Methods for Eliciting an Immune Response and Compositions Therefore

The invention contemplates methods of eliciting in an individual an immune response to one or more *H. influenzae* type IV pilus polypeptides. In certain embodiments, the methods elicit an immune response to the PilA protein. These methods elicit one or more immune responses, including but not limited to, immune responses which inhibit bacterial replication, immune responses which block *H. influenzae* adherence to cells, immune responses which prevent *H. influenzae* twitching and immune responses which prevent biofilm formation. In one embodiment, the methods comprise a step of administering an immunogenic dose of a composition comprising one or more polypeptides of the invention. In another embodiment, the methods comprise administering an immunogenic dose of a composition comprising a cell expressing one or more polypeptides of the invention. In yet another embodiment, the methods comprise administering an immunogenic dose of a composition comprising one or more polynucleotides encoding one or more polypeptides of the invention. The polynucleotide may be a naked polynucleotide not associated with any other nucleic acid or may be in a vector such as a plasmid or viral vector (e.g., adeno-associated virus vector or adenovirus vector). The methods may be used in combination in a single individual. The methods may be used prior or subsequent to *H. influenzae* infection of an individual.

In one embodiment of methods of the invention, a composition of the invention is administered as a priming dose followed by one or more booster doses. Co-administration of proteins or polypeptides that beneficially enhance the immune response such as cytokines (e.g., IL-2, IL-12, GM-CSF), cytokine-inducing molecules (e.g. Leaf) or costimulatory molecules is also contemplated.

An "immunogenic dose" of a composition of the invention is one that generates, after administration, a detectable humoral (antibody) and/or cellular (T cell) immune response in comparison to the immune response detectable before administration or in comparison to a standard immune response before administration. The invention contemplates that the immune response resulting from the methods may be protective and/or therapeutic. In a preferred embodiment, the antibody and/or T cell immune response protects the individual from *H. influenzae* infection, particularly infection of the middle ear and/or the nasopharynx or lower airway. In this use, the precise dose depends on the patient's state of health and weight, the mode of administration, the nature of the formulation, etc., but generally ranges from about 1.0 μg to about 5000 μg per 70 kilogram patient, more commonly from about 10 to about 500 μg per 70 kg of body weight.

Humoral immune response may be measured by many well known methods, such as Single Radial Immunodiffussion Assay (SRID), Enzyme Immunoassay (EIA) and Hemagglutination Inhibition Assay (HAI). In particular, SRID utilizes a layer of a gel, such as agarose, containing the immunogen being tested. A well is cut in the gel and the serum being tested is placed in the well. Diffusion of the antibody out into the gel leads to the formation of a precipitation ring whose area is proportional to the concentration of the antibody in the serum being tested. EIA, also known as ELISA (Enzyme Linked Immunoassay), is used to determine total antibodies in the sample. The immunogen is adsorbed to the surface of a microtiter plate. The test serum is exposed to the plate followed by an enzyme linked immunoglobulin, such as IgG. The enzyme activity adherent to the plate is quantified by any convenient means such as spectrophotometry and is proportional to the concentration of antibody directed against the immunogen present in the test sample. HAI utilizes the capability of an immunogen such as viral proteins to agglutinate chicken red blood cells (or the like). The assay detects neutralizing antibodies, i.e., those antibodies able to inhibit hemagglutination. Dilutions of the test serum are incubated with a standard concentration of immunogen, followed by the addition of the red blood cells. The presence of neutralizing antibodies will inhibit the agglutination of the red blood cells by the immunogen. Tests to measure cellular immune response include determination of delayed-type hypersensitivity or measuring the proliferative response of lymphocytes to target immunogen.

The invention correspondingly provides compositions suitable for eliciting an immune response to pilus polypeptides of the invention. As noted above, the compositions comprise one or more pilus polypeptides, cells expressing one or more polypeptides, or one or more polynucleotides encoding one or more pilus polypeptides. The compositions may also comprise other ingredients such as carriers and adjuvants.

In compositions of the invention, a pilus polypeptide may be fused to another protein when produced by recombinant methods. In one embodiment, the other protein may not, by itself, elicit antibodies, but it stabilizes the first protein and forms a fusion protein retaining immunogenic activity. In another embodiment, the fusion protein comprises another protein that is immunogenic, such as Glutathione-S-transferase (GST) or beta-galactosidase, relatively large co-proteins which solubilize the fusion protein and facilitate production and purification thereof. The other protein may act as an adjuvant in the sense of providing a generalized stimulation of the immune system. The other protein may be fused to either the amino or carboxy terminus of the NTHi protein of the invention.

In other compositions of the invention, pilus polypeptides may be otherwise linked to carrier substances. Any method of creating such linkages known in the art may be used. Linkages can be formed with heterobifunctional agents that generate a disulfide link at one functional group end and a peptide link at the other, such as a disulfide amide forming agent, e.g., N-succidimidyl-3-(2-pyridyldithio) proprionate (SPDP) (See, e.g., Jansen et al., *Immun. Rev.* 62:185, 1982) and bifunctional coupling agents that form a thioether rather than a disulfide linkage such as reactive esters of 6-maleimidocaproic acid, 2-bromoacetic acid, 2-iodoacetic acid, 4-(N-maleimido-methyl) cyclohexane-1-carboxylic acid and the like, and coupling agent which activate carboxyl groups by combining them with succinimide or 1-hydroxy-2-nitro-4-sulfonic acid, for sodium salt such as succidimidyl 4-(N-maleimido-methyl) cyclohexane-1-carboxylate (SMCC).

The pilus polypeptides may be formulated as neutral or salt forms. Pharmaceutically acceptable salts, include the acid addition salts (formed with the free amino groups of the peptide) and which are formed with inorganic acids such as, e.g., hydrochloric or phosphoric acids, or such organic acids as acetic, oxalic, tartaric, mandelic. Salts formed with the free carboxyl groups may also be derived from inorganic bases such as, e.g., sodium, potassium, ammonium, calcium, or ferric hydroxides, and such organic bases as isopropylamine, trimethylamine, 2-ethylamino ethanol, histidine, and procaine.

Compositions of the invention may further comprise adjuvants. Known adjuvants include, for example, emulsions such as Freund's Adjuvants and other oil emulsions, *Bordetella pertussis*, MF59, purified saponin from *Quillaja saponaria* (QS21), aluminum salts such as hydroxide, phosphate and alum, calcium phosphate, (and other metal salts), gels such as aluminum hydroxide salts, mycobacterial products including muramyl dipeptides, solid materials, particles such as liposomes and virosomes. Examples of natural and bacterial products known to be used as adjuvants include monophosphoryl lipid A (MPL), RC-529 (synthetic MPL-like acylated monosaccharide), OM-174 which is a lipid A derivative from *E. coli*, holotoxins such as cholera toxin (CT) or one of its derivatives, pertussis toxin (PT) and heat-labile toxin (LT) of *E. coli* or one of its derivatives, and CpG oligonucleotides. Adjuvant activity can be affected by a number of factors, such as carrier effect, depot formation, altered lymphocyte recirculation, stimulation of T-lymphocytes, direct stimulation of B-lymphocytes and stimulation of macrophages.

Compositions of the invention are typically formulated as injectables, either as liquid solutions or suspensions; solid forms suitable for solution in, or suspension in, liquid prior to injection may also be prepared. The preparation may also be emulsified. The active immunogenic ingredient is often mixed with excipients, which are pharmaceutically acceptable and compatible with the active ingredient. Suitable excipients are, e.g., water, saline, dextrose, glycerol, ethanol, or the like and combinations thereof. In addition, if desired, the vaccine may contain minor amounts of auxiliary substances such as wetting or emulsifying agents, pH buffering agents, or adjuvants, which enhance the effectiveness of the vaccine. The vaccines are conventionally administered parenterally, by injection, for example, either subcutaneously or intramuscularly.

Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10%-95% of active ingredient, preferably 25-70%.

Compositions may also be administered through transdermal routes utilizing jet injectors, microneedles, electroporation, sonoporation, microencapsulation, polymers or liposomes, transmucosal routes and intranasal routes using nebulizers, aerosols and nasal sprays. Microencapsulation using natural or synthetic polymers such as starch, alginate and chitosan, D-poly L-lactate (PLA), D-poly DL-lactic-coglycolic microspheres, polycaprolactones, polyorthoesters, polyanhydrides and polyphosphazenes polyphosphatazanes are useful for both transdermal and transmucosal administration. Polymeric complexes comprising synthetic poly-ornithate, poly-lysine and poly-arginine or amphipathic peptides are useful for transdermal delivery systems. In addition, due to their amphipathic nature, liposomes are contemplated for transdermal, transmucosal and intranasal vaccine delivery systems. Common lipids used for vaccine delivery include N-(1)2,3-(dioleyl-dihydroxypropyl)-N,N,N,-trimethylammonium-methyl sulfate (DOTAP), dioleyloxy-propyl-trimethylammonium chloride DOTMA, dimystyloxypropyl-3-dimethyl-hydroxyethyl ammonium (DMRIE), dimethyldioctadecyl ammonium bromide (DDAB) and 9N(N',N-dimethylaminoethane)carbamoyl)cholesterol (DC-Chol). The combination of helper lipids and liposomes will enhance up-take of the liposomes through the skin. These helper lipids include, dioleoyl phosphatidylethanolamine (DOPE), dilauroylphosphatidylethanolamine (DLPE), dimyristoyl phosphatidylethanolamine (DMPE), dipalmitoylphosphatidylethanolamine (DPPE). In addition, triterpenoid glycosides or saponins derived from the Chilean soap tree bark (*Quillaja saponaria*) and chitosan (deacetylated chitan) have been contemplated as useful adjuvants for intranasal and transmucosal vaccine delivery.

Formulations may be presented in unit-dose or multi-dose containers, for example, sealed ampules and vials and may be stored in a freeze-dried condition requiring only the addition of the sterile liquid carrier immediately prior to use.

Methods of Inhibiting *H. influenzae*

Alternatively, the invention includes methods of inhibiting *H. influenzae* type IV pili function in an individual. The methods comprise administering to the individual, for example, one or more antibodies of the invention; one or more polypeptides of the invention; one or more antisense polynucleotides of the invention; one or more RNAi molecules; and/or one or more small molecules, in an amount that inhibits function of the pili. In vitro assays may be used to demonstrate the ability to inhibit pili function. Embodiments of these methods include, for example, methods using inhibitors of pilus polypeptide synthesis and/or pilus assembly, inhibitors of adherence mediated via type IV pili, inhibitors that disrupt existing biofilms mediated by type IV pili, and inhibitors of twitching.

Inhibition is contemplated for any pathological condition involving *H. influenzae*, for example, OM, pneumonia, sinusitis, septicemia, endocarditis, epiglottitis, septic arthritis, meningitis, postpartum and neonatal infections, postpartum and neonatal sepsis, acute and chromic salpingitis, epiglottis, pericardis, cellulitis, osteomyelitis, endocarditis, cholecystitis, intraabdominal infections, urinary tract infection, mastoiditis, aortic graft infection, conjunctivitis, Brazilian purpuric fever, occult bacteremia and exacerbation of underlying lung diseases such as chronic bronchitis, bronchietasis and cystic fibrosis.

Compositions comprising inhibitors of *H. influenzae* type IV pili function are provided. The compositions may consist of one of the foregoing active ingredients alone, may comprise combinations of the foregoing active ingredients or may comprise additional active ingredients used to treat bacterial infections. As discussed above, the compositions may comprise one or more additional ingredients such as pharmaceutically effective carriers. Also as discussed above, dosage and frequency of the administration of the compositions are determined by standard techniques and depend, for example, on the weight and age of the individual, the route of administration, and the severity of symptoms. Administration of the pharmaceutical compositions may be by routes standard in the art, for example, parenteral, intravenous, oral, buccal, nasal, pulmonary, rectal, intranasal, or vaginal.

Animal Model

Methods of the invention may be demonstrated in a chinchilla model widely accepted as an experimental model for OM. In particular, a chinchilla model of NTHi-induced OM has been well characterized (Bakaletz et al., *J. Infect. Dis.,* 168: 865-872, 1993; Bakaletz and Holmes, *Clin. Diagn. Lab. Immunol.,* 4: 223-225, 1997; Suzuki and Bakaletz, *Infect. Immun.,* 62: 1710-1718, 1994; Mason et al., *Infect. Immun.,* 71:3454-3462, 2003), and has been used to determine the protective efficacy of several NTHi outer membrane proteins, combinations of outer membrane proteins, chimeric synthetic peptide vaccine components, and adjuvant formulations against OM (Bakaletz et al., *Vaccine,* 15: 955-961, 1997; Bakaletz et al., *Infect. Immun.,* 67: 2746-2762, 1999; Kennedy et al., *Infect. Immun.,* 68: 2756-2765, 2000; Kyd et al., *Infect. Immun.,* 66:2272-2278, 2003; Novotny and Bakaletz, *J. Immunol.,* 171, 1978-1983, 2003).

In the model, adenovirus predisposes chinchillas to *H. influenzae*-induced OM media, which allowed for the establishment of relevant cell, tissue and organ culture systems for the biological assessment of NTHi (Bakaletz et al., *J. Infect. Dis.,* 168: 865-72, 1993; Suzuki et al., *Infect. Immunity* 62: 1710-8, 1994). Adenovirus infection alone has been used to assess the transudation of induced serum antibodies into the tympanum (Bakaletz et al., *Clin. Diagnostic Lab Immunol.,* 4(2): 223-5, 1997) and has been used as a co-pathogen with NTHi, to determine the protective efficacy of several active and passive immunization regimens targeting various NTHi outer membrane proteins, combinations of OMPs, chimeric synthetic peptide vaccine components, and adjuvant formulations as vaccinogens against otitis media (Bakaletz et al., *Infect Immunity,* 67(6): 2746-62, 1999; Kennedy et al., *Infect. Immun.,* 68(5): 2756-65, 2000; Novotny et al., *Infect Immunity* 68(4): 2119-28, 2000; Poolman et al., *Vaccine* 19 (Suppl. 1): S108-15, 2000).

Methods of Detecting *H. influenzae* Bacteria

Also provided by the invention are methods for detecting bacteria in an individual. In one embodiment, the methods comprise detecting pili polynucleotides of the invention in a biological sample using primers or probes that specifically bind to the polynucleotides. Detection of the polynucleotide may be accomplished by numerous techniques routine in the art involving, for example, hybridization and/or PCR. In another embodiment, the methods comprise detecting pili polypeptides of the invention in a biological sample using antibodies of the invention that specifically bind to the polypeptides. The antibodies may be used in any immunoassay system known in the art including, but not limited to, radioimmunoassays, ELISA assays, sandwich assays, precipitin reactions, gel diffusion precipitin reactions, immunodiffusion assays, agglutination assays, fluorescent immunoassays, protein A immunoassays and immunoelectrophoresis assays. Biological samples to be utilized in the methods include, but are not limited to, blood, serum, ear fluid, spinal fluid, sputum, urine, lymphatic fluid and cerebrospinal fluid.

BRIEF DESCRIPTION OF THE DRAWING

FIG. 1 is an alignment of amino acid sequences of the PilA polypeptides of NTHi Rd, 86-028NP (SEQ ID NO: 2), 1728MEE (SEQ ID NO: 26), 1729MEE (SEQ ID NO: 28), 3224A (SEQ ID NO: 30), 10548MEE (SEQ ID NO: 32), 1060MEE (SEQ ID NO: 34), 1885MEE (SEQ ID NO: 36), 1714MEE (SEQ ID NO: 38), 1236MEE (SEQ ID NO: 40), 1128MEE (SEQ ID NO: 42), 214NP (SEQ ID NO: 44).

DETAILED DESCRIPTION OF THE INVENTION

The following examples illustrate the invention wherein Example 1 describes sequences of NTHi strain 86-028NP type IV pilus genes of the invention and detection of the pilA gene in thirteen clinical *H. influenzae* isolates, Example 2 demonstrates classical type IV pilus-dependent aggregate formation by NTHi strain 86-028NP, Example 3 demonstrates twitching motility in NTHi strain 86-028NP, Example 4 describes observation of type IV pili on NTHi strain 86-928NP by negative staining and transmission electron microscopy, Example 5 describes the generation of a pilA mutant, Example 6 describes experiments in a chinchilla model of infection with NTHi and pilA mutant NTHi, Example 7 describes pilA genes from ten NTHi clinical isolates, Example 8 describes experiments demonstrating an immune response to NTHi pilli in children and Example 9 describes the identification of NTHi peptide fragments for use as immunogens.

Example 1

A type IV pilus regulon was identified in an OM isolate of NTHi.

Many strains of NTHi, including strain 86-028NP, do not possess the hif locus required for the expression of hemagglutinating LKP pili (Mhlanga-Mutangadura et al., *J. Bacteriol.,* 180(17), 4693-4703, 1988), yet most form biofilms. Because pili are important to biofilm formation in other bacterial systems, the contig set from the NTHi strain 86-028NP genomic sequencing effort (see http://www.microbial-pathogenesis.org or co-owned U.S. Ser. No. 60/453,134) was analyzed for genes potentially encoding another type of pilus. The dataset was BLASTed using the tblasn algorithm with default parameters using the *Pseudomonas aeruginosa* proteins annotated as related to the type IV pilus or twitching motility for *P. aeruginosa* including PilQ and PilT at www.Pseudomonas.com. The translated polypeptide for the *P. multocida* PilA protein was also used in this search (Doughty et al., *Vet. Microbial.,* 72, 79-90, 2000).

What initially appeared to be a cryptic type IV pilus gene locus was identified. Specifically, in strain 86-028NP, there are four genes that are highly homologous to those in *H. influenzae* strain Rd, *A. pleuropneumoniae* and *P. multocida* (Stevenson et al., *Vet. Microbiol.,* 92, 121-134, 2003; Doughty et al., supra; Zhang et al., *FEMS Microbiol Lett,* 189, 15-18, 2000; and Ruffolo et al., *Infect. Immun.,* 65, 339-343, 1997). These genes encode PilA, PilB, PilC and PilD in strain Rd (Dougherty and Smith, *Microbiology,* 145(2), 401-409, 1999).

The NTHi strain 86-028NP regulon includes a gene cluster of polynucleotides encoding pilin polypeptides PilA (major pilin subunit), PilD (leader peptidase), PilB and PilC (contemplated to be transcribed from the same mRNA and to be involved in the assembly/disassembly of the pilin structure); a gene cluster of polynucleotides encoding pilin polypeptides ComA, ComB, ComC, ComD, ComE, and ComF (involved in competence for transformation and pilus expression); and another gene encoding PilF (required for type IV pilus biogenesis). The amino acid sequences of the pilin polypeptides set out in the following SEQ ID NOs: PilA in SEQ ID NO: 2, PilB in SEQ ID NO: 4, PilC in SEQ ID NO: 6, PilD in SEQ ID NO: 8, ComA in SEQ ID NO: 10, ComB in SEQ ID NO: 12, ComC in SEQ ID NO: 14, ComD in SEQ ED NO: 16, ComE in SEQ ID NO: 18, ComF in SEQ ID NO: 20 and PilF in SEQ ID NO: 22. The gene sequences encoding the polypeptides are set out in the following SEQ ID NOs which respectively encode the foregoing polypeptides: pilA in SEQ ID NO: 1, pilB in SEQ ID NO: 3, pilC in SEQ ID NO: 5, pilD in SEQ ID NO: 7, comA in SEQ ID NO: 9, comB in SEQ ID NO: 11, comC in SEQ ID NO: 13, comD in SEQ ID NO: 15, comE in SEQ ID NO: 17, comF in SEQ ID NO: 19; and pilF in SEQ ID NO: 21. Each of the polynucleotides sequences includes a final three nucleotides representing a stop codon.

In gene expression profiling studies employing cDNA microarrays to characterize the regulation of NTHi genes during the development of competence (i.e., the natural ability of NTHi to take up foreign DNA potentially enhancing or expanding its genetic diversity), the corn genes as well as the pil genes are up-regulated during competence development.

In a Southern blot experiment using pilA sequences as a probe, thirteen low-passage clinical NTHi OM isolates recovered from patients undergoing tympanostomy and tube insertion for chronic otitis media and one clinical isolate recovered from a patient with cystic fibrosis had a single copy of pilA within their genome. These fourteen total isolates were designated by the following strain numbers, respectively: 86-028NP; 1728MEE; 1729MEE; 1714MEE; 214NP; 1236MEE; 165NP; 1060MEE; 1128MEE; 10548MEE; 3224A; 3185A, 1885MEE and 27W11679INI.

In the experiment, bacterial chromosomal DNA was isolated using a PUREGENE DNA isolation kit from Gentra Systems (Minneapolis, Minn.), digested with MfeI and the digests run on a 0.8% agarose gel. DNA was transferred to a Nytran SuPerCharge membrane using the Turbo Blotter kit (Schleicher & Schuell, Keene, N.H.). The probe was generated by PCR amplification of the coding sequence of the 86-028NP pilA gene using the primers 5'tgtgacacttccgcaaaaa (SEQ ID NO: 23) and 5'taataaaaggaaaatgaatga (SEQ ID NO: 24). The amplicon was purified using a QIAquick PCR purification kit (Qiagen Inc., Valencia, Calif.). Following the manufacturer's directions, 100 ng of purified PCR product was labeled with horseradish peroxidase using the ECL Direct Nucleic Acid Labeling and Detection System (Amersham Biosciences UK Ltd., Little Chalfont, Bucks, UK). Developed blots were exposed to Fuji Super Rx X-ray film (Fuji Photo Film Co., Tokyo, Japan).

The PilA polypeptide of NTHi strain 86-028NP has a predicted and apparent molecular mass of approximately 14 kDa, contains an N-terminal methylated phenylalanine.

Example 2

NTHi strain 86-028NP formed classic aggregates in a sub-agar surface translocation assay and a surface growth assay when grown under conditions of nutrient depletion.

NTHi strain 86-028NP was grown on chocolate agar for 18-20 hours (37° C., 5% $CO_2$, in a humidified atmosphere) prior to all experiments. Subsequently, this organism was inoculated onto either sBHI, a rich medium on which the NTHi grows very well, or a chemically defined medium which supports the growth of *H. influenzae* (Coleman et al. *J. Clin. Micro.*, 41:4408-4410, 2003) that comprised 83% RPMI1640 media (Gibco BRL, Rockville, Md.), sodium pyruvate (87.3 mM) (Gibco BRL), β-NAD (0.0087 mg/ml) (Sigma Chemical Co., St Louis, Mo.), HEME-histidine (0.0175 mg/ml) (Sigma), Uracil (0.087 mg/ml) (Sigma), and inosine (1.75 mg/ml) (Sigma).

Both agars were poured into one of two formats, in sterile 8-well chamber slides (Lab-tech, Naperville, Ill.) or into sterile 35 mm glass petri dishes (Fisher Scientific, location). When the glass slide was separated from the 8-well chamber slides, the agar remained within the chambers, thus enabling use of the "bottom" surface of the agar for inoculation, which is optimal for assay of twitching motility due to the relative smoothness of this surface (Semmler et al., *Microbiology,* 145, 2863-2873, 1999 and Mattick, *Ann. Rev. Microbiol.,* 56, 289-314, 2002). Whereas agars cast into 8-well chamber slides were used to demonstrate a surface growth phenotype, agars poured into the petri dishes were used for demonstration of subsurface agar translocation (Semmler et al., supra) whereas agars cast into 8-well chamber slides were used to demonstrate agar surface growth phenotype. All assays were repeated a minimum of three times, on separate days.

Agars that had been poured into sterile glass petri dishes were inoculated subsurface with 0.5 μl of a suspension of NTHi grown as described above, using a sterile micropipet tip. Plates were observed after 24 hours incubation (37° C., 5% $CO_2$) and were then held at room temperature (25° C.) for an additional 24 hours prior to re-reading for signs of bacterial translocation between the bottom surface of the agar and the glass petri dish.

On sBHI medium, 24 hours post-inoculation, NTHi was observed to have grown in a small area (~0.5 mm radius) surrounding the inoculation site between the agar and the glass petri dish bottom. After an additional 24 hours, the growth pattern remained similar to that observed at 24 hours. On the chemically defined medium after 24 hours of incubation, growth of NTHi was observed between the agar surface and the glass petri dish bottom, at a distance 2 to 5 mm from the inoculation site. The bacteria had also aggregated into small colonies in a halo-like pattern surrounding the inoculation site. After 48 hours, NTHi had formed a very distinct array of micro-colonies with many occurring at a distance >5 mm from the inoculation site. The formation of micro-satellites up to 5 mm distance from original site of inoculation was a hallmark finding of growth on chemically defined medium and was never seen when strain 86-028NP was grown on rich agar.

Chamber slides were either inoculated with 0.5 ul of a suspension of 18-20 hour chocolate agar-grown NTHi [suspended in sterile pyrogen free saline (American Pharmaceutical Partners Inc., Schaumburg, Ill.)], or a single colony was stabbed for transfer to the surface of the agar with a sterile toothpick.

On sBHI medium, thirty minutes post-inoculation, NTHi appeared in close association with the agar surface and was growing in a sheet-like pattern. At 2.5 hours, approximately 80-90% of the surface area was covered with a thin sheet of bacteria. Also at this time, micro-aggregates of NTHi began to appear. At 6-7 hours post-inoculation, these micro-aggregates were discernable with the naked eye and there were approximately 3-5 micro-aggregates per well. In addition, NTHi were still observed to be growing as a sheet that covered approximately 50-70% of the agar surface. Twenty-four hours after inoculation, NTHi appeared as large single colonies at each inoculation site.

On chemically defined medium, like that observed on sBHI, thirty minutes post-inoculation, NTHi appeared to be growing in sheet, however the density of the bacteria appeared much less than that observed on sBHI agar. At 2.5 hours after inoculation, numerous micro-aggregates were evident throughout the agar surface. In contrast to those noted when NTHi was inoculated onto sBHI agar, these micro-aggregates were larger and much more dense in appearance. Approximately 30-40 micro-aggregates could be seen on each well. There was still a large area of sheet like growth of NTHi at this time point, with approximately 80% of the surface area covered by bacteria. At 6-7 hours post inoculation, the micro-aggregates were larger, denser, and easily seen with the naked eye. Also, areas of radial growth or halos were seen radiating outward from large colonies, similar to the growth patterns described for *Neisseria* and *Pseudomonas* sp. (refs). By this time period, most of the bacteria appeared to be arranged in small clusters or microaggregates with a very small proportion seen covering the agar surface as a sheet or monolayer. After 24 hours, there were large single colonies at each inoculation site, however there were also many small satellite colonies present over the entire agar surface, including sites remote from the points of inoculation.

Thus, NTHi strain 86-028NP demonstrates classic aggregate formation, similar to that reported for type IV pilus-expressing *P. aeruginosa* (Semmler et al., *Microbiology,* 145(10), 2863-2873, 1999), when grown under conditions of nutrient depletion.

Example 3

The movement of individual NTHi cells between a glass coverslip and a smooth agar surface was traced by videomicroscopy. The cells moved at approximately 0.42 μm/sec, consistent with that reported for twitching *P. aeruginosa* (Skerker and Berg, *Proc. Natl. Acad., Sci. USA,* 98, 6901-6904, 2001) and *Neisseria gonorrhoeae* (Merz et al., *Nature,* 207, 98-102, 2000).

A loopful of NTHi stain 86-028NP, grown on chocolate agar at 37° C. and 5% $CO_2$ for 20 hours and then held at ambient temperature for an additional 24 hours, was suspended in sterile water and 0.5 μl of the resulting suspension was placed onto a sterile glass slide. To provide contrast and thus aid visualization, 0.5 μl of trypan blue (0.4%, Sigma, St. Louis Mo.) was added to the bacterial suspension. The droplet was then covered with a sterile coverslip and viewed via light microscope (Axioskope 40, Zeiss, Thornwood, N.Y.). Specimens were observed at room temperature over a period of approximately 15-20 minutes. The bacteria were readily observable and directional movement of several, although not all, cells or microaggregates of cells was noted. In order to stimulate activity, we added 0.5 μl of a heme solution (1 mg/ml) (Sigma, St. Louis, Mo.) to one side of the sterile coverslip. Twitching activity was documented by the capture of both video [video otoscopy system (MEDR$_x$ Inc, Seminole, Fla.) attached to a VCR] and still images in order to determine length and rate of excursions.

Individual cells, or microaggregates of cells, traveled a total linear distance of approximately 11.0 μm over a period of 51 seconds (rate approximately 0.22 μm/sec). However, over the entire period of observation, the rate of twitching motility observed ranged from 0.14 to 0.48 μm/sec.

Example 4

Type IV pili were visualized by negative staining and transmission electron microscopy.

Overnight cultures of NTHi strain 86-028NP were inoculated onto sBHI and defined agar plates and incubated for 2, 6 or 24 hours at 37° C., 5% $CO_2$. Additionally, cultures were inoculated into sBHI broth and defined broth and incubated for 2.5 or 5.5 hours. These latter time points represent entry into exponential and lag phases of growth, respectively. Bacteria were then negatively stained using a Whatman-filtered solution containing 2.0% ammonium acetate w/v (Sigma) and 2.0% ammonium molybdate w/v (Sigma) in sterile water (Bakaletz et al. *Infect Immun,* 1988 56:331-5). Formvar- and carbon-coated copper grids, 300 mesh, (Electron Microscopy Sciences) were touched to individual colonies grown on agar plates, and then floated on a droplet of the negative stain solution. Broth-grown cultures were pelleted, the bacteria resuspended in sterile water and grids were floated on equal volumes of bacterial suspension and negative stain. After 5 minutes, grids were blotted and allowed to air dry prior to viewing in an Hitachi Model H-600 transmission electron microscope with attached video monitor (Gatan, Inc., Pleasanton, Calif.) and digital imaging system (Gatan, Inc.).

When NTHi were grown on sBHI, no type IV pilus-like structures were observed. Conversely, when grown under defined nutrient conditions, NTHi was seen to express structures of approximately 6-7 nm diameter. Many of these structures were also found free on the grid surface. There were approximately 5 to 6 pili per bacterial cell and these were polar in location.

Example 5

A mutant deficient in the expression of PilA was generated to further characterize components of the structures observed when strain 86-028NP was grown in alkaline conditions on chemically defined media.

The pilA gene and approximately 1 kb 5' and 3' of the gene from strain 86-028NP was amplified by PCR, cloned into pGEM-T Easy (Promega) and the DNA sequence determined to verify that there were no changes in the sequence in the clone as a result of the PCR amplification. As there was no convenient restriction site in the pilA gene, a BamHI site was engineered into the gene using the Stratagene QuikChange Site-Directed Mutagenesis Kit. The resulting construct was linearized with BamHI and the gene was insertionally inactivated with the ΩKn-2 cassette (Perez-Casal et al., *J. Bacteriol.,* 173: 2617-2624, 1991). The resulting construct was linearized and transformed into strain 86-028NP using the MIV method (Poje and Redfield, p. 57-70 in Herbert et al. (Eds.), *Haemophilus influenzae* Protocols, Humana Press Inc., Toronto, 2003). Kanamycin-resistant clones were selected and insertional inactivation of the 86-028NP pilA gene was verified in selected clones by Southern hybridization.

When the pilA mutant was evaluated for expression of type IV pili after growth under conditions that induced the increased expression of type IV pili in the parental isolate (Example 4), no cell-associated or free type IV pili were observed confirming that the pilA gene product (and/or the pilBCD gene products since the mutation is pilA is likely to disrupt the downstream gene products) are required for pilus expression.

Example 6

To determine whether type IV pili are necessary for colonization of the nasopharynx, as well as survival in and/or ability to form a biofilm in the middle ear, we challenged fourteen adult chinchillas both intranasally and transbullarly with either the parent strain 86-028NP or with an isogenic pilA mutant (Example 5). On days 2, 5, 10, 15 and 20 post-challenge, nasopharyngeal lavages and epitympanic taps were performed, and both nasal and middle ear mucosae were retrieved from 1-2 chinchillas per cohort to determine cfu of NTHi in each of these anatomic sites. Both the parent and pilA mutant were able to survive in the chinchilla host for twenty days. However, whereas both strains were present in equivalent amounts in lavage and tap fluids, when assayed for an adherent subpopulation in tissue homogenates of nasal mucosae, the pilA mutant was absent from, or below our ability to detect, in 80% of the homogenates recovered after day 5 whereas 87% of similar nasal mucosae recovered from animals challenged with the parental isolate were culture positive.

Confocal microscopy was performed on snap-frozen tissue to determine whether a biofilm was present. The biomass formed by the pilA mutant in the middle ear was of a different character than the well-structured biofilm characteristic of the parental isolate. The data indicate that NTHi type IV pili play a key role in the disease course of OM.

Example 7

The pilA gene of ten clinical isolates of NTHi have been sequenced. The nucleotide and amino acid sequences from the isolates are respectively set out as follows: 1728MEE in SEQ ID NOs: 25 and 26, 1729MEE in SEQ ID NOs: 27 and 28, 3224A in SEQ ID NOs: 29 and 30, 10548MEE in SEQ ID NOs: 31 and 32, 1060MEE in SEQ ID NOs: 33 and 34, 1885MEE in SEQ ID NOs: 35 and 36, 1714MEE in SEQ ID NOs: 37 and 38, 1236MEE in SEQ ID NOs: 39 and 40, 1128MEE in SEQ ID NOs: 41 and 42, and 214NP in SEQ ID NOs: 43 and 44. An alignment of the amino acid sequences with those of the pilA polypeptides from Rd and 86-028NP is presented in FIG. 1.

The pilA genes of all isolates encode a 12-residue leader peptide that is largely invariant save a Q to L substitution at position 6 in two isolates as well as in strain Rd. Mature PilA contains 137 residues and is predicted to contain a characteristic methylated phenylalanine at position +1. Tyrosine residues at positions +24 and +27, and believed to be involved in subunit-subunit interactions, are highly conserved as are four Cys residues at positions +50, +60, +119 and +132. Interestingly, the NTHi PilA proteins appear to represent a new class of type IV pili. The leader peptide is larger than that characteristic for type IVa pilins (typically 5-6 residues in length), yet shorter than the typical IVb leader peptide (15-30 residues). At 137 residues, the mature NTHi pilin is shorter than either class IVa or IVb pilins (150 and 190 residues, respectively). Since the NTHi PilA proteins begin with an N-methylated phenylalanine, they are more like class IVa pilins however in electron micrographs, free NTHi type IV pili always appear in laterally associated bundles, a phenotype more classically associated with class IVb pilins due to their ability to self-associate through anti-parallel interactions.

In terms of NTHi PilA sequence diversity, overall these sequences are highly homologous. See FIG. 1. Two areas of potentially important diversity, if surface accessible and also targeted for vaccine development due to protective immunodominance or adhesion-binding function, exist at positions 55-64 and 79-87. Within the first region, amongst the clinical isolates, there appears to be two major variants, one representing the majority (seven of eleven isolates, 64%) and characterized by the following sequence: NET/ITNCT/MGGK and the other representing the minority (four of eleven isolates, 36%) and characterized by the sequence: GKP/LST/SCSGGS. There are however some additional minor variations at positions +57 and +61 in the majority grouping and at positions +57 and +59 for the minority grouping. The diversity noted at position +61 is only seen in one isolate to date (strain #1885), wherein there is a T to M substitution. Within the second focused region of diversity (position 79-87), there appears to be two equally distributed variants among the clinical NTHi isolates. The sequence ASVKTQSGG is present in five of eleven clinical isolates (~45%), whereas the sequence KSVTTSNGA is present in six of eleven clinical isolates (~55%).

Overall, of the seven isolates with the majority sequence at position 55-64, five isolates also have the KSVTTSNGA motif at region 79-87, with the remaining two isolates having the ASVKTQSGG motif in this region. Of the four remaining clinical isolates with the minority sequence at position 55-64, three of these also have the ASVKTQSGG motif at region 79-87, with only one isolate having the KSVTTSNGA sequence in this domain. Thereby, depending on whether or not these are conservative substitutions or not and if the sequences reside within surface accessible, hydrophilic areas of high antigenic index and thus are targets for vaccine development, they may or may not need to be included as type IV pili-based components for inducing an immune response to NTHi.

Example 8

To examine the role of type IV pili in NTHi-induced OM and determine if antibodies from children during natural disease recognize type IV pili, four sequential synthetic peptides were synthesized representing amino acids 21-137 of SEQ ID NO: 2 of the mature PilA of NTHi strain 86-028NP and assayed via biosensor versus a panel of pediatric sera and middle ear effusions obtained from children with OM. Serum from children at 2, 6-7, or 18-19 mos and 4-6 yrs of age with OM due to NTHi were segregated into low and high incidence groups, as determined by the number of episodes of OM.

To date, antibodies in sera obtained from children 2 and 6-7 mos of age of either high or low incidence of OM demonstrated limited reactivity with any of the type IV pili peptides, with values of 3-38 and 4-61 resonance units (RU), respectively. However, a striking difference between these groups was seen with serum obtained at 18-19 mos of age. Whereas values obtained with sera from the low incidence 18-19 mos group were 44-105 RU, sera from the high incidence panel recognized the type IV pili peptides up to five-fold greater (81-528 RU). At 4-6 yrs of age, as children naturally resolve OM, reactivity to the type IV pili peptides was again similar between the two incidence groups. To confirm that the reactivity observed here was specific for disease due to NTHi, sera from children with OM due to *S. pneumoniae* were also assayed. In all cases, RU values of 16-120 were obtained versus all type IV pili peptides. To assay for the presence of antibodies directed against type IV pili in effusions obtained from the middle ears, we also assayed these fluids via biosensor. Whereas effusions from children with OM due to *Streptococcus* were unreactive, those recovered from children with OM due to NTHi were highly reactive with type IV pili peptides. Collectively, the data strongly suggests that NTHi type IV pili are expressed in vivo, during the disease course of OM and that these structures are immunogenic.

Example 9

Identification of immunogens that confer broad cross-protective immune responses against NTHi may be carried out as follows.

Synthesis of NTHi Pilin Peptides

In order to map both immunodominant and adhesion-binding domains of PilA, a panel of overlapping sequential peptides as well as peptides derived from two focused areas of known diversity (see Example 6 above) are synthesized. For example, thirteen 15-mer peptides with a 5-residue overlap will be synthesized to map the entire 137 residue mature pilin protein. The final C-terminal peptide will actually be a 17-mer spanning residues 121-137 in order to incorporate the final two amino acids of mature PilA. To accommodate the two described regions of diversity, two variants of the peptide that spans residues 51-65 and two variants of the peptide that spans residues 79-95 will be synthesized. In order to fully accommodate this latter region of diversity, two peptides are made varying in length by one amino acid at the N-terminus since the region of diversity actually spans residues 79-87. Due to the additional residue, each of these latter two peptides will be 16-mers in length. Thus a total of fifteen peptides will be synthesized: twelve will be 15-mers, one will be a 17-mer and two will be 16-mer peptides. The peptides are set out in Table 2 below wherein amino acid residue numbers correspond to amino acids in SEQ ID No: 2.

TABLE 2

| Peptide | Sequence |
|---|---|
| OLP1 [Residues 1-15] | FTLIELMIVIAIIAI |
| OLP2 [Residues 11-25] | AIIAILATIAIPSYQ |
| OLP3 [Residues 21-35] | IPSYQNYTKKAAVSE |
| OLP4 [Residues 31-45] | AAVSELLQASAPYKA |
| OLP5 [Residues 41-55] | APYKADVELCVYSTN |
| OLP6vA [Residues 51-65] | VYSTNETTNCTGGKN |
| OLP6vB [Residues 51-65] | VYSTGKPSTCSGGSN |
| OLP7 [Residues 61-75] | TGGKNGIAADITTAK |
| OLP8 [Residues 71-85] | ITTAKGYVKSVTTSN |
| OLP9vA [Residues 79-094]77-95 | YVKSVTTSNGAITVKGDGT |
| OLP9vB [Residues 79-94]77-95 | YVASVKTQSGGITVKGNGT |
| OLP10 [Residues 91-105] | KGDGTLANMEYILQA |
| OLP11 [Residues 101-115] | YILQATGNAATGVTW |
| OLP12 [Residues 111-125] | TGVTWTTTCKGTDAS |
| OLP13 [Residues 121-137] | GTDASLFPANFCGSVTQ |

Generation of Recombinant NTHi Pilin (rPilA)

Recombinant PilA protein (rPilA) may be generated to serve as a more readily renewable product for use in assays to represent the entire pilin subunit protein. To do this, the published protocol of Keizer et al. (*J. Biol. Chem.,* 276: 24186-14193, 2001), who studied a pilin which also had four Cys residues as it will be critical that rPilA similarly be properly folded so as to possess functional qualities of the native pilin subunit, is utilized. Briefly, a truncated pilin is engineered wherein the first 28 residues are removed from the N-terminus to prevent aggregation, and this truncated pilin will be further engineered to be transported to the periplasm by means of the incorporation of an OmpA leader sequence in the construct. Using this strategy Keizer et al. generated a recombinant soluble monomeric *P. aeruginosa* pilin protein that was able to bind to its receptor (asialo GM1) in in vitro assays and decrease morbidity and mortality in mice when the peptide was delivered 15 mins. prior to heterologous challenge. This soluble, monomeric, truncated form of NTHi PilA will be useful in the studies described below.

Mapping Immunodominant Domains of PilA

The peptides and native and recombinant PilA proteins are used in concert with both acute and convalescent chinchilla and pediatric sera in addition to middle ear fluids from chinchillas and children experiencing either experimental or natural OM due to NTHi (all available within our current specimen collection or planned for collection as part of a separate initiative) to map immunodominant domains of PilA via ELISA and also biosensor assays. Briefly, PilA peptides, rPilA and native pili are bound to 96-well microtiter plates or to a biosensor chip surface, then assayed for the relative amount of antibody within serum or middle ear fluid samples that binds to each peptide.

These studies identify those regions of the pilin subunit that are relatively more immunodominant than others as recognized by both the chinchilla host and the human child. Due to the fact that the N-terminal-most synthetic peptide is comprised of highly non-polar (hydrophobic) amino acids and is thus likely buried within the pilus fiber and inaccessible to antibody, this 15-mer peptide is anticipated to serve as an internal negative control for the assays described here. Normal pediatric sera and naïve chinchilla sera will serve as negative serum controls and middle ear lavage fluids recovered from a naïve animal will be used as a negative control for effusions recovered during NTHi infection of the middle ear.

Mapping Adhesion Binding Domains of PilA

In order to map the eukaryotic cell binding domains of PilA, competitive ELISA assays are conducted as well as evaluations of the ability of the synthetic pilin peptides to inhibit NTHi binding to eukaryotic cells in cell culture via confocal microscopy. For initial screening assays, relevant eukaryotic target cells are grown within 96-well microtiter dishes. Cells will be washed, then pre-incubated with synthetic pilin peptides, rPilA or native NTHi pili [0.2 μg in PBS] to determine their relative ability to block binding of NTHi strain 86-028NP (grown under conditions known to promote pilin expression) to these eukaryotic cells. Relative adherence of NTHi will be determined using polyclonal antisera directed against a homologous whole NTHi OMP preparation and HRP-conjugated protein A with color developed with tetramethylbenzidine (TMB). For these assays relevant epithelial target cells [i.e. chinchilla middle ear epithelial cells (CMEEs), normal human bronchial/tracheal cells (NHuBr), human type II alveolar epithelial cell line (A549s)], a clinically irrelevant epithelial target cell to which NTHi do not adhere (CHOs) as well as an endothelial target cells [human umbilical vein endothelial cells (HUVECs)] will be used.

For those peptides that show inhibitory activity (typically the cut-off is at ≥15% inhibition of adherence relative to controls), any dose-dependence to the observed bacterial adherence blocking capability is determined. The interaction may be further evaluated by conducting adherence-blockade assays using a Transwell system wherein respiratory tract epithelial cells (CMEEs and NHuBrs) are grown at the air-fluid interface. These cells are incubated with first synthetic peptides of interest (or appropriate controls, i.e. isolated OMP P5 and P2 as positive and negative controls for NTHi surface proteins involved or not in adherence, respectively and rPilA) to attempt to block available Tfp receptors, then they will be washed 5× with fresh growth medium followed by inoculation with ~2-5×107 NTHi grown under conditions we know will promote expression of Tfp. Cultures will be washed to remove non-adherent bacteria, then fixed with methanol on ice for 5 min, air dried, rinsed with PBS and the membranes removed from the Transwell and placed on glass coverslips for imaging via confocal microscopy. To detect adherent NTHi, chinchilla hyperimmune anti-NTHi OMP serum and FITC-Protein A will be used to document the interaction of NTHi with its epithelial target cell, or conversely the blocking of this interaction by peptides that represent putative adhesion binding domains of PilA.

Choice of Immunogen

Based on the data acquired in above, immunogenic peptides are chosen based on both relative immunodominance as well as ability to inhibit adherence of NTHi to respiratory epithelial target cells. Depending on the biochemical and structural characteristics of the regions of interest, the peptides will be produced as either synthetic peptide(s) or recombinant peptide(s).

Immunogenicity and protective efficacy of the PilA immunogens is evaluated initially in the chinchilla animal model disclosed herein and in human trials.

Example Summary

The foregoing evidence indicates that NTHi express functional type IV pili on their surface. The proteins encoded by these genes are known to be important for transformation competence in typeable *H. influenzae* and are contemplated herein to be important for biofilm formation by NTHi as well. Collectively, these observations indicate that NTHi is likely to up-regulate expression of type IV pili in the nutrient restricted environment of the human host. Thus, type IV pili represent an excellent target for a vaccine and/or for an antimicrobial strategy for pathogenic conditions caused by NTHi as well as *H. influenzae* strains a, b, c, e and f.

We claim:

1. A composition comprising (A) a fusion protein comprising (i) a peptide fragment of amino acid of SEQ ID NO: 2 wherein the peptide fragment elicits an immune response to *H. influenzae* pilin polypeptide or wherein the peptide fragment inhibits *H. influenzae* cellular adherence and (ii) an immunogenic protein and (B) an adjuvant.

2. The composition of claim 1 further comprising a pharmaceutically acceptable carrier.

3. A composition comprising (A) a fusion protein comprising (i) a peptide fragment of the amino acid of SEQ ID NO: 2 wherein the peptide fragment comprises amino acids 69-102 of SEQ ID NO:2 wherein the peptide fragment elicits an immune response to *H. influenzae* pilin polypeptide or wherein the peptide fragment inhibits *H. influenzae* cellular adherence and (ii) an immunogenic protein and (B) an adjuvant.

4. The composition of claim 3 further comprising a pharmaceutically acceptable carrier.

5. A composition comprising (A) a fusion protein comprising (i) a peptide fragment of the amino acid of SEQ ID NO: 2 wherein the peptide fragment comprises amino acids 103-137 of SEQ ID NO:2 wherein the peptide fragment elicits an immune response to *H. influenzae* pilin polypeptide or wherein the peptide fragment inhibits *H. influenzae* cellular adherence and (ii) an immunogenic protein and (B) an adjuvant.

6. The composition of claim 5 further comprising a pharmaceutically acceptable carrier.

7. A method for eliciting an immune response to non-typeable *H. influenzae* comprising administering an immunogenic dose of a fusion protein comprising (i) a peptide fragment of amino acid of SEQ ID NO: 2 wherein the peptide fragment elicits an immune response to *H. influenzae* pilin polypeptide or wherein the peptide fragment inhibits *H. influenzae* cellular adherence and (ii) an immunogenic protein.

8. A method for eliciting an immune response to non-typeable *H. influenzae* comprising administering an immunogenic dose of a fusion protein comprising (i) a peptide fragment of the amino acid of SEQ ID NO: 2 wherein the peptide fragment comprises amino acids 69-102 of SEQ ID NO:2 wherein the peptide fragment elicits an immune response to *H. influenzae* pilin polypeptide or wherein the peptide fragment inhibits *H. influenzae* cellular adherence and (ii) an immunogenic protein.

9. A method for eliciting an immune response to non-typeable *H. influenzae* comprising administering an immunogenic dose of a fusion protein comprising (i) a peptide fragment of the amino acid of SEQ ID NO: 2 wherein the peptide fragment comprises amino acids 103-137 of SEQ ID NO:2 wherein the peptide fragment elicits an immune response to *H. influenzae* pilin polypeptide or wherein the peptide fragment inhibits *H. influenzae* cellular adherence and (ii) an immunogenic protein.

* * * * *

SEQUENCE LISTING

```
<160> NUMBER OF SEQ ID NOS: 59

<210> SEQ ID NO 1
<211> LENGTH: 4345
<212> TYPE: DNA
<213> ORGANISM: H. influenzae
<220> FEATURE:
<221> NAME/KEY: CDS
<222> LOCATION: (403)..(852)

<400> SEQUENCE: 1

gcgatcatta aaattgacat attgcgtaat tcgcccattt cgttcgatca aacaatgtgc      60

tgaaacacgc atttgataaa tttctgcaaa ataaggatga atcttaggat ctaattttcc     120

ttgaaaaaaa tcatccacat atccgccgcc aaattgttct ggcggcagac taatataatg     180

aataaccaat aaggaaatat cctgtggatt tgggcgttta tcgaagtgag gtgactgaat     240

ttgccgacaa tccaatatac cttgttcaat atcttttagt ttttgcatac ttttttcctt     300

tttttgcgat caggatcgca gaaaaagtgc ggtcaatttt acaaacaaat ttttcctttt     360

cacaatgtcg tcgctaacaa aggcttaata aaaggaaaat ga atg aaa cta aca        414
                                               Met Lys Leu Thr
                                               1

aca cag caa acc ttg aaa aaa ggg ttt aca tta ata gag cta atg att       462
Thr Gln Gln Thr Leu Lys Lys Gly Phe Thr Leu Ile Glu Leu Met Ile
5                   10                  15                  20

gtg att gca att att gct att tta gcc act atc gca att ccc tct tat       510
Val Ile Ala Ile Ile Ala Ile Leu Ala Thr Ile Ala Ile Pro Ser Tyr
                25                  30                  35

caa aat tat act aaa aaa gca gcg gta tct gaa tta ctg caa gcg tca       558
Gln Asn Tyr Thr Lys Lys Ala Ala Val Ser Glu Leu Leu Gln Ala Ser
            40                  45                  50

gcg cct tat aag gct gat gtg gaa tta tgt gta tat agc aca aat gaa       606
Ala Pro Tyr Lys Ala Asp Val Glu Leu Cys Val Tyr Ser Thr Asn Glu
        55                  60                  65

aca aca aac tgt acg ggt gga aaa aat ggt att gca gca gat ata acc       654
Thr Thr Asn Cys Thr Gly Gly Lys Asn Gly Ile Ala Ala Asp Ile Thr
    70                  75                  80

aca gca aaa ggc tat gta aaa tca gtg aca aca agc aac ggt gca ata       702
Thr Ala Lys Gly Tyr Val Lys Ser Val Thr Thr Ser Asn Gly Ala Ile
85                  90                  95                  100

aca gta aaa ggg gat ggc aca ttg gca aat atg gaa tat att ttg caa       750
Thr Val Lys Gly Asp Gly Thr Leu Ala Asn Met Glu Tyr Ile Leu Gln
                105                 110                 115

gct aca ggt aat gct gca aca ggt gta act tgg aca aca act tgc aaa       798
Ala Thr Gly Asn Ala Ala Thr Gly Val Thr Trp Thr Thr Thr Cys Lys
```

```
          120                 125                 130

gga acg gat gcc tct tta ttt cca gca aat ttt tgc gga agt gtc aca      846
Gly Thr Asp Ala Ser Leu Phe Pro Ala Asn Phe Cys Gly Ser Val Thr
        135                 140                 145

caa tga cgagctatgc tttacttcat actcagcgtg taaccgctca aaatggcgag       902
Gln

atctttacga tctcgccaga tttatgggaa cgcaatcagc agcaacaatc cttgctcttg    962

cggtattttg ctttgccact taaagaagaa aataatcgtc tttggctagg ggttgattct   1022

ctctccaatc tttcagcttg tgaaaccatt gcgtttataa caggaaaacc tgtcgaacca   1082

attttgttag aaagcagcca actcaaagaa ctgttacaac aacttactcc gcaccaaatg   1142

caagtggaag agcaagttaa attctatcaa catcaagaaa cccattttga acaagaagat   1202

gatgaacctg ttatccgctt acttaatcag atttttgaat ctgccttaca aaaaaatgcc   1262

tctgatattc atttagaaac cttggctgat cagtttcaag tgcggtttag aattgatggt   1322

gttttacaac cacaaccctt aataagcaaa atattcgcca atcgtattat ttcacgctta   1382

aaattactgg ctaaattaga tattagtgaa aatcgacttc cacaagatgg acgatttcaa   1442

tttaaaacca ctttttccga tattcttgat tttcgccttt caaccttacc aacccattgg   1502

ggcgaaaaaa tcgtgttgcg agcgcaacaa aataaacctg tagaacttag ctttgctgaa   1562

ctgggtatga ccgaaaatca gcaacaagca tttcaacgct cacttagcca gccacaagga   1622

ttaattttag taaccggccc cacaggaagt gggaaaagta tctcgcttta caccgcactt   1682

cagtggctaa atacgcctga taaacatatt atgaccgctg aagatcccat tgaaattgaa   1742

cttgatggta ttattcaaag ccaaattaat ccgcagattg gattagattt tagccgtcta   1802

ttgcgtgctt ttttacgtca agatcccgac atcattatgc taggtgaaat tcgagatgaa   1862

gaaagtgcaa ggattgcact acgtgccgct caaacgggac atttggtgct ttcaacttta   1922

cataccaatg atgcaatatc tgccatttct cgcttacaac aactcggtat tcaacaacat   1982

gaaattgaaa acagtttact actcgtcatt gcacagcgtc ttgtacgaaa aatctgtcca   2042

aagtgcggtg gaaatttaat aaattcttgt gattgccatc aaggttatcg agggcgaatc   2102

ggcgtgtatc aatttctaca ttggcaacag aatggctatc aaacggattt tgagaattta   2162

cgagagagtg gtttggaaaa agttagccaa ggcataacag atgagaaaga aattgaacgt   2222

gtgttaggta aaaactcatg actaaaaaac tcttttatta tcaaggtagt aacgcattaa   2282

atcagaaaca aaaaggctca attattgcgg atacgaaaca acaagcgcac tttcagttaa   2342

taagccgcgg gcttactcac atcaaattac aacaaaactg gcaatttggg gcaaaaccca   2402

aaaattcaga aatcagtgaa ttactcaatc aattagcgac attgctacag tccgtaattc   2462

cgttaaaaaa cagcctacaa attttgcaac aaaattgtac tcaaattatg ctcaacaaat   2522

ggcttgaacg actgcttcaa tccattgaat ctggcttagc attctcacaa gccattgaac   2582

aacaaggaaa atatctcaca caacaagaaa ttcaactgat tcaagtggga gaaatgacag   2642

gaaaacttgc cgtagtttgt aaaaaaatag ccacgcaccg tagtcaatct ttggctttac   2702

aacgcaaatt acagaaaatt atgttatatc cctcaatggt attgggaatt tctctattat   2762

tgacactcgc attactgctt tttatcgcgc ctcaatttgc tgaaatgtac agtggcaata   2822

atgcggagtt accaacaata accgcaatat tgctctcaat atctaatttc cttaagcaaa   2882

atattggcat tttgctattt ttcgttttga gtttttttct attttattat ttctatctaa   2942

aacgccagac ttggtttcat caaaagaaaa atcaacttat ttctatcacg cctatttttg   3002
```

```
gcacaattca aaagctttca cgtttagtga actttagtca aagtttacaa attatgttgc   3062
aggccggcgt accgcttaat caggcactag acagttttct tcctcgcaca caaacttggc   3122
aaaccaagaa aacgcttgta aacgatatgg tattagataa agaagtgcgg tcaattttgc   3182
aatgggtttc tcaaggctat gcgttttcta atagcgtaag tagcgatctt ttcccgatgg   3242
aagcacaaca aatgctacaa attggcgaac aaagcggaaa actcgctttg atgctagagc   3302
atatcgcaga taattaccaa gaaaaactta atcatcaaat tgacttactc tcacaaatgc   3362
tagaaccatt aatgatggta atcatcggca gtctgattgg gattattatg atgggaatgt   3422
atttacctat ctttaatatg ggatcagtta ttcaatgatt tacttcacaa tgtttttatt   3482
aggcggcatc ttagggatcg cattgtggtt ctacctatct ggttttatta cgcatttgca   3542
gcaagagatt tatgcgactt acgttgaatt atttccacaa aacagttctc catttcaacc   3602
gcactttgcc tctattcaac aaaaaaagtg cggtcatatt ttgaggtatt tttttagtat   3662
tggggttgga tttatatttt tacaaattgc cttcaaagat tctattttta ctgtatggat   3722
cggactcaca cttattattc tttggacaat cagttatctt gattggcact atcaacttat   3782
ttctacgaca ccctgtttat ggttacttac tctcggttta tttggcgcag acaataactt   3842
ttcattgcta acgttatctg aaagcataaa aagtgcggct agttttttta ttgttttcta   3902
cgcaatctat tggattgcaa aatgttatta tagaaaagaa gcctttggac ggggagatta   3962
ttggctagca atggcattag gaagttttat tcatttagaa accttaccgc actttttatt   4022
attagcctca gtgcttggaa tatgtttttc gcttattcat aaaaagaaaa aagaatttat   4082
acctttttgcc ccttttatga acttatcggc tatcattatt tatctcgtca aatattacgg   4142
atattaaaaa ggggaaaaca taatattttt cccttgttct tcatagaagt gcggttgttt   4202
ttacgaacgt ttcatcactt caaaaaactc ttcgttggtt ttcgccatca tcagcttatc   4262
aatcaagaat tccattgcat ccacttcatc cattggatta agaatcttac gaagaatcca   4322
catttttgt aattcgtccg ctg                                             4345
```

```
<210> SEQ ID NO 2
<211> LENGTH: 149
<212> TYPE: PRT
<213> ORGANISM: H. influenzae

<400> SEQUENCE: 2

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
```

```
    130                 135                 140

Gly Ser Val Thr Gln
145


<210> SEQ ID NO 3
<211> LENGTH: 4345
<212> TYPE: DNA
<213> ORGANISM: H. influenzae
<220> FEATURE:
<221> NAME/KEY: CDS
<222> LOCATION: (849)..(2243)

<400> SEQUENCE: 3

gcgatcatta aaattgacat attgcgtaat tcgcccattt cgttcgatca aacaatgtgc      60

tgaaacacgc atttgataaa tttctgcaaa ataaggatga atcttaggat ctaattttcc     120

ttgaaaaaaa tcatccacat atccgccgcc aaattgttct ggcggcagac taatataatg     180

aataaccaat aaggaaatat cctgtggatt tgggcgttta tcgaagtgag gtgactgaat     240

ttgccgacaa tccaatatac cttgttcaat atcttttagt tttgcatac ttttttcctt     300

tttttgcgat caggatcgca gaaaaagtgc ggtcaatttt acaaacaaat ttttcctttt     360

cacaatgtcg tcgctaacaa aggcttaata aaaggaaaat gaatgaaact aacaacacag     420

caaaccttga aaaaagggtt tacattaata gagctaatga ttgtgattgc aattattgct     480

attttagcca ctatcgcaat tccctcttat caaaattata ctaaaaaagc agcggtatct     540

gaattactgc aagcgtcagc gccttataag gctgatgtgg aattatgtgt atatagcaca     600

aatgaaacaa caaactgtac gggtggaaaa aatggtattg cagcagatat aaccacagca     660

aaaggctatg taaaatcagt gacaacaagc aacggtgcaa taacagtaaa aggggatggc     720

acattggcaa atatggaata tattttgcaa gctacaggta atgctgcaac aggtgtaact     780

tggacaacaa cttgcaaagg aacggatgcc tctttatttc cagcaaattt ttgcggaagt     840

gtcacaca atg acg agc tat gct tta ctt cat act cag cgt gta acc gct      890
         Met Thr Ser Tyr Ala Leu Leu His Thr Gln Arg Val Thr Ala
         1               5                   10

caa aat ggc gag atc ttt acg atc tcg cca gat tta tgg gaa cgc aat      938
Gln Asn Gly Glu Ile Phe Thr Ile Ser Pro Asp Leu Trp Glu Arg Asn
15                  20                  25                  30

cag cag caa caa tcc ttg ctc ttg cgg tat ttt gct ttg cca ctt aaa      986
Gln Gln Gln Gln Ser Leu Leu Leu Arg Tyr Phe Ala Leu Pro Leu Lys
                35                  40                  45

gaa gaa aat aat cgt ctt tgg cta ggg gtt gat tct ctc tcc aat ctt     1034
Glu Glu Asn Asn Arg Leu Trp Leu Gly Val Asp Ser Leu Ser Asn Leu
            50                  55                  60

tca gct tgt gaa acc att gcg ttt ata aca gga aaa cct gtc gaa cca     1082
Ser Ala Cys Glu Thr Ile Ala Phe Ile Thr Gly Lys Pro Val Glu Pro
        65                  70                  75

att ttg tta gaa agc agc caa ctc aaa gaa ctg tta caa caa ctt act     1130
Ile Leu Leu Glu Ser Ser Gln Leu Lys Glu Leu Leu Gln Gln Leu Thr
    80                  85                  90

ccg cac caa atg caa gtg gaa gag caa gtt aaa ttc tat caa cat caa     1178
Pro His Gln Met Gln Val Glu Glu Gln Val Lys Phe Tyr Gln His Gln
95                  100                 105                 110

gaa acc cat ttt gaa caa gaa gat gat gaa cct gtt atc cgc tta ctt     1226
Glu Thr His Phe Glu Gln Glu Asp Asp Glu Pro Val Ile Arg Leu Leu
                115                 120                 125

aat cag att ttt gaa tct gcc tta caa aaa aat gcc tct gat att cat     1274
Asn Gln Ile Phe Glu Ser Ala Leu Gln Lys Asn Ala Ser Asp Ile His
            130                 135                 140
```

```
tta gaa acc ttg gct gat cag ttt caa gtg cgg ttt aga att gat ggt      1322
Leu Glu Thr Leu Ala Asp Gln Phe Gln Val Arg Phe Arg Ile Asp Gly
        145                 150                 155

gtt tta caa cca caa ccc tta ata agc aaa ata ttc gcc aat cgt att      1370
Val Leu Gln Pro Gln Pro Leu Ile Ser Lys Ile Phe Ala Asn Arg Ile
    160                 165                 170

att tca cgc tta aaa tta ctg gct aaa tta gat att agt gaa aat cga      1418
Ile Ser Arg Leu Lys Leu Leu Ala Lys Leu Asp Ile Ser Glu Asn Arg
175                 180                 185                 190

ctt cca caa gat gga cga ttt caa ttt aaa acc act ttt tcc gat att      1466
Leu Pro Gln Asp Gly Arg Phe Gln Phe Lys Thr Thr Phe Ser Asp Ile
                195                 200                 205

ctt gat ttt cgc ctt tca acc tta cca acc cat tgg ggc gaa aaa atc      1514
Leu Asp Phe Arg Leu Ser Thr Leu Pro Thr His Trp Gly Glu Lys Ile
            210                 215                 220

gtg ttg cga gcg caa caa aat aaa cct gta gaa ctt agc ttt gct gaa      1562
Val Leu Arg Ala Gln Gln Asn Lys Pro Val Glu Leu Ser Phe Ala Glu
        225                 230                 235

ctg ggt atg acc gaa aat cag caa caa gca ttt caa cgc tca ctt agc      1610
Leu Gly Met Thr Glu Asn Gln Gln Gln Ala Phe Gln Arg Ser Leu Ser
    240                 245                 250

cag cca caa gga tta att tta gta acc ggc ccc aca gga agt ggg aaa      1658
Gln Pro Gln Gly Leu Ile Leu Val Thr Gly Pro Thr Gly Ser Gly Lys
255                 260                 265                 270

agt atc tcg ctt tac acc gca ctt cag tgg cta aat acg cct gat aaa      1706
Ser Ile Ser Leu Tyr Thr Ala Leu Gln Trp Leu Asn Thr Pro Asp Lys
                275                 280                 285

cat att atg acc gct gaa gat ccc att gaa att gaa ctt gat ggt att      1754
His Ile Met Thr Ala Glu Asp Pro Ile Glu Ile Glu Leu Asp Gly Ile
            290                 295                 300

att caa agc caa att aat ccg cag att gga tta gat ttt agc cgt cta      1802
Ile Gln Ser Gln Ile Asn Pro Gln Ile Gly Leu Asp Phe Ser Arg Leu
        305                 310                 315

ttg cgt gct ttt tta cgt caa gat ccc gac atc att atg cta ggt gaa      1850
Leu Arg Ala Phe Leu Arg Gln Asp Pro Asp Ile Ile Met Leu Gly Glu
    320                 325                 330

att cga gat gaa gaa agt gca agg att gca cta cgt gcc gct caa acg      1898
Ile Arg Asp Glu Glu Ser Ala Arg Ile Ala Leu Arg Ala Ala Gln Thr
335                 340                 345                 350

gga cat ttg gtg ctt tca act tta cat acc aat gat gca ata tct gcc      1946
Gly His Leu Val Leu Ser Thr Leu His Thr Asn Asp Ala Ile Ser Ala
                355                 360                 365

att tct cgc tta caa caa ctc ggt att caa caa cat gaa att gaa aac      1994
Ile Ser Arg Leu Gln Gln Leu Gly Ile Gln Gln His Glu Ile Glu Asn
            370                 375                 380

agt tta cta ctc gtc att gca cag cgt ctt gta cga aaa atc tgt cca      2042
Ser Leu Leu Leu Val Ile Ala Gln Arg Leu Val Arg Lys Ile Cys Pro
        385                 390                 395

aag tgc ggt gga aat tta ata aat tct tgt gat tgc cat caa ggt tat      2090
Lys Cys Gly Gly Asn Leu Ile Asn Ser Cys Asp Cys His Gln Gly Tyr
    400                 405                 410

cga ggg cga atc ggc gtg tat caa ttt cta cat tgg caa cag aat ggc      2138
Arg Gly Arg Ile Gly Val Tyr Gln Phe Leu His Trp Gln Gln Asn Gly
415                 420                 425                 430

tat caa acg gat ttt gag aat tta cga gag agt ggt ttg gaa aaa gtt      2186
Tyr Gln Thr Asp Phe Glu Asn Leu Arg Glu Ser Gly Leu Glu Lys Val
                435                 440                 445

agc caa ggc ata aca gat gag aaa gaa att gaa cgt gtg tta ggt aaa      2234
Ser Gln Gly Ile Thr Asp Glu Lys Glu Ile Glu Arg Val Leu Gly Lys
```

-continued

```
        450                 455                 460

aac tca tga ctaaaaaact cttttattat caaggtagta acgcattaaa           2283
Asn Ser

tcagaaacaa aaaggctcaa ttattgcgga tacgaaacaa caagcgcact ttcagttaat   2343

aagccgcggg cttactcaca tcaaattaca acaaaactgg caatttgggg caaaacccaa   2403

aaattcagaa atcagtgaat tactcaatca attagcgaca ttgctacagt ccgtaattcc   2463

gttaaaaaac agcctacaaa ttttgcaaca aaattgtact caaattatgc tcaacaaatg   2523

gcttgaacga ctgcttcaat ccattgaatc tggcttagca ttctcacaag ccattgaaca   2583

acaaggaaaa tatctcacac aacaagaaat tcaactgatt caagtgggag aaatgacagg   2643

aaaacttgcc gtagtttgta aaaaaatagc cacgcaccgt agtcaatctt tggctttaca   2703

acgcaaatta cagaaaatta tgttatatcc ctcaatggta ttgggaattt ctctattatt   2763

gacactcgca ttactgcttt ttatcgcgcc tcaatttgct gaaatgtaca gtggcaataa   2823

tgcggagtta ccaacaataa ccgcaatatt gctctcaata tctaatttcc ttaagcaaaa   2883

tattggcatt ttgctatttt tcgttttgag ttttttttcta ttttattatt tctatctaaa   2943

acgccagact tggtttcatc aaaagaaaaa tcaacttatt tctatcacgc ctatttttgg   3003

cacaattcaa aagctttcac gtttagtgaa ctttagtcaa agtttacaaa ttatgttgca   3063

ggccggcgta ccgcttaatc aggcactaga cagttttctt cctcgcacac aaacttggca   3123

aaccaagaaa acgcttgtaa acgatatggt attagataaa gaagtgcggt caattttgca   3183

atgggtttct caaggctatg cgttttctaa tagcgtaagt agcgatcttt tcccgatgga   3243

agcacaacaa atgctacaaa ttggcgaaca aagcggaaaa ctcgctttga tgctagagca   3303

tatcgcagat aattaccaag aaaaacttaa tcatcaaatt gacttactct cacaaatgct   3363

agaaccatta atgatggtaa tcatcggcag tctgattggg attattatga tgggaatgta   3423

tttacctatc tttaatatgg gatcagttat tcaatgattt acttcacaat gtttttatta   3483

ggcggcatct tagggatcgc attgtggttc tacctatctg gttttattac gcatttgcag   3543

caagagattt atgcgactta cgttgaatta tttccacaaa acagttctcc atttcaaccg   3603

cactttgcct ctattcaaca aaaaaagtgc ggtcatattt tgaggtattt ttttagtatt   3663

ggggttggat ttatattttt acaaattgcc ttcaaagatt ctatttttac tgtatggatc   3723

ggactcacac ttattattct ttggacaatc agttatcttg attggcacta tcaacttatt   3783

tctacgacac cctgtttatg gttacttact ctcggtttat ttggcgcaga caataacttt   3843

tcattgctaa cgttatctga aagcataaaa agtgcggcta gtttttttat tgttttctac   3903

gcaatctatt ggattgcaaa atgttattat agaaaagaag cctttggacg gggagattat   3963

tggctagcaa tggcattagg aagttttatt catttagaaa ccttaccgca ctttttatta   4023

ttagcctcag tgcttggaat atgtttttcg cttattcata aaaagaaaaa agaatttata   4083

ccttttgccc cttttatgaa cttatcggct atcattattt atctcgtcaa atattacgga   4143

tattaaaaag gggaaaacat aatatttttc ccttgttctt catagaagtg cggttgtttt   4203

tacgaacgtt tcatcacttc aaaaaactct tcgttggttt tcgccatcat cagcttatca   4263

atcaagaatt ccattgcatc cacttcatcc attggattaa gaatcttacg aagaatccac   4323

atttttgta attcgtccgc tg                                           4345
```

<210> SEQ ID NO 4
<211> LENGTH: 464
<212> TYPE: PRT

<213> ORGANISM: H. influenzae

<400> SEQUENCE: 4

```
Met Thr Ser Tyr Ala Leu Leu His Thr Gln Arg Val Thr Ala Gln Asn
1               5                   10                  15

Gly Glu Ile Phe Thr Ile Ser Pro Asp Leu Trp Glu Arg Asn Gln Gln
            20                  25                  30

Gln Gln Ser Leu Leu Leu Arg Tyr Phe Ala Leu Pro Leu Lys Glu Glu
        35                  40                  45

Asn Asn Arg Leu Trp Leu Gly Val Asp Ser Leu Ser Asn Leu Ser Ala
    50                  55                  60

Cys Glu Thr Ile Ala Phe Ile Thr Gly Lys Pro Val Glu Pro Ile Leu
65                  70                  75                  80

Leu Glu Ser Ser Gln Leu Lys Glu Leu Leu Gln Gln Leu Thr Pro His
                85                  90                  95

Gln Met Gln Val Glu Glu Gln Val Lys Phe Tyr Gln His Gln Glu Thr
            100                 105                 110

His Phe Glu Gln Glu Asp Asp Glu Pro Val Ile Arg Leu Leu Asn Gln
        115                 120                 125

Ile Phe Glu Ser Ala Leu Gln Lys Asn Ala Ser Asp Ile His Leu Glu
    130                 135                 140

Thr Leu Ala Asp Gln Phe Gln Val Arg Phe Arg Ile Asp Gly Val Leu
145                 150                 155                 160

Gln Pro Gln Pro Leu Ile Ser Lys Ile Phe Ala Asn Arg Ile Ile Ser
                165                 170                 175

Arg Leu Lys Leu Leu Ala Lys Leu Asp Ile Ser Glu Asn Arg Leu Pro
            180                 185                 190

Gln Asp Gly Arg Phe Gln Phe Lys Thr Thr Phe Ser Asp Ile Leu Asp
        195                 200                 205

Phe Arg Leu Ser Thr Leu Pro Thr His Trp Gly Glu Lys Ile Val Leu
    210                 215                 220

Arg Ala Gln Gln Asn Lys Pro Val Glu Leu Ser Phe Ala Glu Leu Gly
225                 230                 235                 240

Met Thr Glu Asn Gln Gln Gln Ala Phe Gln Arg Ser Leu Ser Gln Pro
                245                 250                 255

Gln Gly Leu Ile Leu Val Thr Gly Pro Thr Gly Ser Gly Lys Ser Ile
            260                 265                 270

Ser Leu Tyr Thr Ala Leu Gln Trp Leu Asn Thr Pro Asp Lys His Ile
        275                 280                 285

Met Thr Ala Glu Asp Pro Ile Glu Ile Glu Leu Asp Gly Ile Ile Gln
    290                 295                 300

Ser Gln Ile Asn Pro Gln Ile Gly Leu Asp Phe Ser Arg Leu Leu Arg
305                 310                 315                 320

Ala Phe Leu Arg Gln Asp Pro Asp Ile Ile Met Leu Gly Glu Ile Arg
                325                 330                 335

Asp Glu Glu Ser Ala Arg Ile Ala Leu Arg Ala Ala Gln Thr Gly His
            340                 345                 350

Leu Val Leu Ser Thr Leu His Thr Asn Asp Ala Ile Ser Ala Ile Ser
        355                 360                 365

Arg Leu Gln Gln Leu Gly Ile Gln Gln His Glu Ile Glu Asn Ser Leu
    370                 375                 380

Leu Leu Val Ile Ala Gln Arg Leu Val Arg Lys Ile Cys Pro Lys Cys
385                 390                 395                 400
```

```
Gly Gly Asn Leu Ile Asn Ser Cys Asp Cys His Gln Gly Tyr Arg Gly
                405                 410                 415

Arg Ile Gly Val Tyr Gln Phe Leu His Trp Gln Gln Asn Gly Tyr Gln
            420                 425                 430

Thr Asp Phe Glu Asn Leu Arg Glu Ser Gly Leu Glu Lys Val Ser Gln
        435                 440                 445

Gly Ile Thr Asp Glu Lys Glu Ile Glu Arg Val Leu Gly Lys Asn Ser
    450                 455                 460


<210> SEQ ID NO 5
<211> LENGTH: 4345
<212> TYPE: DNA
<213> ORGANISM: H. influenzae
<220> FEATURE:
<221> NAME/KEY: CDS
<222> LOCATION: (2240)..(3460)

<400> SEQUENCE: 5

gcgatcatta aaattgacat attgcgtaat tcgcccattt cgttcgatca aacaatgtgc     60

tgaaacacgc atttgataaa tttctgcaaa ataaggatga atcttaggat ctaattttcc    120

ttgaaaaaaa tcatccacat atccgccgcc aaattgttct ggcggcagac taatataatg    180

aataaccaat aaggaaatat cctgtggatt tgggcgttta tcgaagtgag gtgactgaat    240

ttgccgacaa tccaatatac cttgttcaat atcttttagt tttgcatac ttttttcctt    300

tttttgcgat caggatcgca gaaaaagtgc ggtcaatttt acaaacaaat ttttcctttt    360

cacaatgtcg tcgctaacaa aggcttaata aaaggaaaat gaatgaaact aacaacacag    420

caaaccttga aaaaagggtt tacattaata gagctaatga ttgtgattgc aattattgct    480

attttagcca ctatcgcaat tccctcttat caaaattata ctaaaaaagc agcggtatct    540

gaattactgc aagcgtcagc gccttataag gctgatgtgg aattatgtgt atatagcaca    600

aatgaaacaa caaactgtac gggtggaaaa aatggtattg cagcagatat aaccacagca    660

aaaggctatg taaaatcagt gacaacaagc aacggtgcaa taacagtaaa aggggatggc    720

acattggcaa atatggaata tattttgcaa gctacaggta atgctgcaac aggtgtaact    780

tggacaacaa cttgcaaagg aacggatgcc tctttatttc cagcaaattt ttgcggaagt    840

gtcacacaat gacgagctat gctttacttc atactcagcg tgtaaccgct caaaatggcg    900

agatctttac gatctcgcca gatttatggg aacgcaatca gcagcaacaa tccttgctct    960

tgcggtattt tgctttgcca cttaaagaag aaaataatcg tctttggcta ggggttgatt   1020

ctctctccaa tctttcagct tgtgaaacca ttgcgtttat aacaggaaaa cctgtcgaac   1080

caattttgtt agaaagcagc caactcaaag aactgttaca acaacttact ccgcaccaaa   1140

tgcaagtgga agagcaagtt aaattctatc aacatcaaga aacccatttt gaacaagaag   1200

atgatgaacc tgttatccgc ttacttaatc agatttttga atctgcctta caaaaaaatg   1260

cctctgatat tcatttagaa accttggctg atcagtttca agtgcggttt agaattgatg   1320

gtgttttaca accacaaccc ttaataagca aaatattcgc caatcgtatt atttcacgct   1380

taaaattact ggctaaatta gatattagtg aaaatcgact tccacaagat ggacgatttc   1440

aatttaaaac cactttttcc gatattcttg attttcgcct ttcaacctta ccaacccatt   1500

ggggcgaaaa aatcgtgttg cgagcgcaac aaaataaacc tgtagaactt agctttgctg   1560

aactgggtat gaccgaaaat cagcaacaag catttcaacg ctcacttagc cagccacaag   1620

gattaatttt agtaaccggc cccacaggaa gtgggaaaag tatctcgctt tacaccgcac   1680
```

-continued

```
ttcagtggct aaatacgcct gataaacata ttatgaccgc tgaagatccc attgaaattg   1740

aacttgatgg tattattcaa agccaaatta atccgcagat tggattagat tttagccgtc   1800

tattgcgtgc ttttttacgt caagatcccg acatcattat gctaggtgaa attcgagatg   1860

aagaaagtgc aaggattgca ctacgtgccg ctcaaacggg acatttggtg ctttcaactt   1920

tacataccaa tgatgcaata tctgccattt ctcgcttaca acaactcggt attcaacaac   1980

atgaaattga aaacagttta ctactcgtca ttgcacagcg tcttgtacga aaaatctgtc   2040

caaagtgcgg tggaaattta ataaattctt gtgattgcca tcaaggttat cgagggcgaa   2100

tcggcgtgta tcaatttcta cattggcaac agaatggcta tcaaacggat tttgagaatt   2160

tacgagagag tggtttggaa aaagttagcc aaggcataac agatgagaaa gaaattgaac   2220

gtgtgttagg taaaaactc atg act aaa aaa ctc ttt tat tat caa ggt agt    2272
                     Met Thr Lys Lys Leu Phe Tyr Tyr Gln Gly Ser
                     1               5                   10

aac gca tta aat cag aaa caa aaa ggc tca att att gcg gat acg aaa     2320
Asn Ala Leu Asn Gln Lys Gln Lys Gly Ser Ile Ile Ala Asp Thr Lys
            15                  20                  25

caa caa gcg cac ttt cag tta ata agc cgc ggg ctt act cac atc aaa     2368
Gln Gln Ala His Phe Gln Leu Ile Ser Arg Gly Leu Thr His Ile Lys
        30                  35                  40

tta caa caa aac tgg caa ttt ggg gca aaa ccc aaa aat tca gaa atc     2416
Leu Gln Gln Asn Trp Gln Phe Gly Ala Lys Pro Lys Asn Ser Glu Ile
    45                  50                  55

agt gaa tta ctc aat caa tta gcg aca ttg cta cag tcc gta att ccg     2464
Ser Glu Leu Leu Asn Gln Leu Ala Thr Leu Leu Gln Ser Val Ile Pro
60                  65                  70                  75

tta aaa aac agc cta caa att ttg caa caa aat tgt act caa att atg     2512
Leu Lys Asn Ser Leu Gln Ile Leu Gln Gln Asn Cys Thr Gln Ile Met
            80                  85                  90

ctc aac aaa tgg ctt gaa cga ctg ctt caa tcc att gaa tct ggc tta     2560
Leu Asn Lys Trp Leu Glu Arg Leu Leu Gln Ser Ile Glu Ser Gly Leu
            95                  100                 105

gca ttc tca caa gcc att gaa caa caa gga aaa tat ctc aca caa caa     2608
Ala Phe Ser Gln Ala Ile Glu Gln Gln Gly Lys Tyr Leu Thr Gln Gln
        110                 115                 120

gaa att caa ctg att caa gtg gga gaa atg aca gga aaa ctt gcc gta     2656
Glu Ile Gln Leu Ile Gln Val Gly Glu Met Thr Gly Lys Leu Ala Val
    125                 130                 135

gtt tgt aaa aaa ata gcc acg cac cgt agt caa tct ttg gct tta caa     2704
Val Cys Lys Lys Ile Ala Thr His Arg Ser Gln Ser Leu Ala Leu Gln
140                 145                 150                 155

cgc aaa tta cag aaa att atg tta tat ccc tca atg gta ttg gga att     2752
Arg Lys Leu Gln Lys Ile Met Leu Tyr Pro Ser Met Val Leu Gly Ile
            160                 165                 170

tct cta tta ttg aca ctc gca tta ctg ctt ttt atc gcg cct caa ttt     2800
Ser Leu Leu Leu Thr Leu Ala Leu Leu Leu Phe Ile Ala Pro Gln Phe
            175                 180                 185

gct gaa atg tac agt ggc aat aat gcg gag tta cca aca ata acc gca     2848
Ala Glu Met Tyr Ser Gly Asn Asn Ala Glu Leu Pro Thr Ile Thr Ala
        190                 195                 200

ata ttg ctc tca ata tct aat ttc ctt aag caa aat att ggc att ttg     2896
Ile Leu Leu Ser Ile Ser Asn Phe Leu Lys Gln Asn Ile Gly Ile Leu
    205                 210                 215

cta ttt ttc gtt ttg agt ttt ttt cta ttt tat tat ttc tat cta aaa     2944
Leu Phe Phe Val Leu Ser Phe Phe Leu Phe Tyr Tyr Phe Tyr Leu Lys
220                 225                 230                 235

cgc cag act tgg ttt cat caa aag aaa aat caa ctt att tct atc acg     2992
```

```
Arg Gln Thr Trp Phe His Gln Lys Lys Asn Gln Leu Ile Ser Ile Thr
                240                 245                 250

cct att ttt ggc aca att caa aag ctt tca cgt tta gtg aac ttt agt      3040
Pro Ile Phe Gly Thr Ile Gln Lys Leu Ser Arg Leu Val Asn Phe Ser
            255                 260                 265

caa agt tta caa att atg ttg cag gcc ggc gta ccg ctt aat cag gca      3088
Gln Ser Leu Gln Ile Met Leu Gln Ala Gly Val Pro Leu Asn Gln Ala
        270                 275                 280

cta gac agt ttt ctt cct cgc aca caa act tgg caa acc aag aaa acg      3136
Leu Asp Ser Phe Leu Pro Arg Thr Gln Thr Trp Gln Thr Lys Lys Thr
    285                 290                 295

ctt gta aac gat atg gta tta gat aaa gaa gtg cgg tca att ttg caa      3184
Leu Val Asn Asp Met Val Leu Asp Lys Glu Val Arg Ser Ile Leu Gln
300                 305                 310                 315

tgg gtt tct caa ggc tat gcg ttt tct aat agc gta agt agc gat ctt      3232
Trp Val Ser Gln Gly Tyr Ala Phe Ser Asn Ser Val Ser Ser Asp Leu
                320                 325                 330

ttc ccg atg gaa gca caa caa atg cta caa att ggc gaa caa agc gga      3280
Phe Pro Met Glu Ala Gln Gln Met Leu Gln Ile Gly Glu Gln Ser Gly
            335                 340                 345

aaa ctc gct ttg atg cta gag cat atc gca gat aat tac caa gaa aaa      3328
Lys Leu Ala Leu Met Leu Glu His Ile Ala Asp Asn Tyr Gln Glu Lys
        350                 355                 360

ctt aat cat caa att gac tta ctc tca caa atg cta gaa cca tta atg      3376
Leu Asn His Gln Ile Asp Leu Leu Ser Gln Met Leu Glu Pro Leu Met
    365                 370                 375

atg gta atc atc ggc agt ctg att ggg att att atg atg gga atg tat      3424
Met Val Ile Ile Gly Ser Leu Ile Gly Ile Ile Met Met Gly Met Tyr
380                 385                 390                 395

tta cct atc ttt aat atg gga tca gtt att caa tga tttacttcac           3470
Leu Pro Ile Phe Asn Met Gly Ser Val Ile Gln
                400                 405

aatgttttta ttaggcggca tcttagggat cgcattgtgg ttctacctat ctggttttat    3530

tacgcatttg cagcaagaga tttatgcgac ttacgttgaa ttatttccac aaaacagttc    3590

tccatttcaa ccgcactttg cctctattca acaaaaaaag tgcggtcata ttttgaggta    3650

ttttttagt attggggttg gatttatatt tttacaaatt gccttcaaag attctatttt     3710

tactgtatgg atcggactca cacttattat tctttggaca atcagttatc ttgattggca    3770

ctatcaactt atttctacga caccctgttt atggttactt actctcggtt tatttggcgc    3830

agacaataac ttttcattgc taacgttatc tgaaagcata aaaagtgcgg ctagtttttt    3890

tattgttttc tacgcaatct attggattgc aaaatgttat tatagaaaag aagcctttgg    3950

acggggagat tattggctag caatggcatt aggaagtttt attcatttag aaaccttacc    4010

gcacttttta ttattagcct cagtgcttgg aatatgtttt tcgcttattc ataaaaagaa    4070

aaaagaattt ataccttttg ccccttttat gaacttatcg gctatcatta tttatctcgt    4130

caaatattac ggatattaaa aaggggaaaa cataatattt ttcccttgtt cttcatagaa    4190

gtgcggttgt ttttacgaac gtttcatcac ttcaaaaaac tcttcgttgg ttttcgccat    4250

catcagctta tcaatcaaga attccattgc atccacttca tccattggat taagaatctt    4310

acgaagaatc cacatttttt gtaattcgtc cgctg                               4345
```

<210> SEQ ID NO 6
<211> LENGTH: 406
<212> TYPE: PRT
<213> ORGANISM: H. influenzae

<400> SEQUENCE: 6

```
Met Thr Lys Lys Leu Phe Tyr Tyr Gln Gly Ser Asn Ala Leu Asn Gln
1               5                   10                  15

Lys Gln Lys Gly Ser Ile Ile Ala Asp Thr Lys Gln Gln Ala His Phe
            20                  25                  30

Gln Leu Ile Ser Arg Gly Leu Thr His Ile Lys Leu Gln Gln Asn Trp
        35                  40                  45

Gln Phe Gly Ala Lys Pro Lys Asn Ser Glu Ile Ser Glu Leu Leu Asn
    50                  55                  60

Gln Leu Ala Thr Leu Leu Gln Ser Val Ile Pro Leu Lys Asn Ser Leu
65                  70                  75                  80

Gln Ile Leu Gln Gln Asn Cys Thr Gln Ile Met Leu Asn Lys Trp Leu
                85                  90                  95

Glu Arg Leu Leu Gln Ser Ile Glu Ser Gly Leu Ala Phe Ser Gln Ala
            100                 105                 110

Ile Glu Gln Gln Gly Lys Tyr Leu Thr Gln Gln Glu Ile Gln Leu Ile
        115                 120                 125

Gln Val Gly Glu Met Thr Gly Lys Leu Ala Val Val Cys Lys Lys Ile
    130                 135                 140

Ala Thr His Arg Ser Gln Ser Leu Ala Leu Gln Arg Lys Leu Gln Lys
145                 150                 155                 160

Ile Met Leu Tyr Pro Ser Met Val Leu Gly Ile Ser Leu Leu Leu Thr
                165                 170                 175

Leu Ala Leu Leu Leu Phe Ile Ala Pro Gln Phe Ala Glu Met Tyr Ser
            180                 185                 190

Gly Asn Asn Ala Glu Leu Pro Thr Ile Thr Ala Ile Leu Leu Ser Ile
        195                 200                 205

Ser Asn Phe Leu Lys Gln Asn Ile Gly Ile Leu Leu Phe Phe Val Leu
    210                 215                 220

Ser Phe Phe Leu Phe Tyr Tyr Phe Tyr Leu Lys Arg Gln Thr Trp Phe
225                 230                 235                 240

His Gln Lys Lys Asn Gln Leu Ile Ser Ile Thr Pro Ile Phe Gly Thr
                245                 250                 255

Ile Gln Lys Leu Ser Arg Leu Val Asn Phe Ser Gln Ser Leu Gln Ile
            260                 265                 270

Met Leu Gln Ala Gly Val Pro Leu Asn Gln Ala Leu Asp Ser Phe Leu
        275                 280                 285

Pro Arg Thr Gln Thr Trp Gln Thr Lys Lys Thr Leu Val Asn Asp Met
    290                 295                 300

Val Leu Asp Lys Glu Val Arg Ser Ile Leu Gln Trp Val Ser Gln Gly
305                 310                 315                 320

Tyr Ala Phe Ser Asn Ser Val Ser Ser Asp Leu Phe Pro Met Glu Ala
                325                 330                 335

Gln Gln Met Leu Gln Ile Gly Glu Gln Ser Gly Lys Leu Ala Leu Met
            340                 345                 350

Leu Glu His Ile Ala Asp Asn Tyr Gln Glu Lys Leu Asn His Gln Ile
        355                 360                 365

Asp Leu Leu Ser Gln Met Leu Glu Pro Leu Met Met Val Ile Ile Gly
    370                 375                 380

Ser Leu Ile Gly Ile Ile Met Met Gly Met Tyr Leu Pro Ile Phe Asn
385                 390                 395                 400

Met Gly Ser Val Ile Gln
                405
```

<210> SEQ ID NO 7
<211> LENGTH: 4345
<212> TYPE: DNA
<213> ORGANISM: H. influenzae
<220> FEATURE:
<221> NAME/KEY: CDS
<222> LOCATION: (3457)..(4149)

<400> SEQUENCE: 7

```
gcgatcatta aaattgacat attgcgtaat tcgcccattt cgttcgatca aacaatgtgc     60
tgaaacacgc atttgataaa tttctgcaaa ataaggatga atcttaggat ctaattttcc    120
ttgaaaaaaa tcatccacat atccgccgcc aaattgttct ggcggcagac taatataatg    180
aataaccaat aaggaaatat cctgtggatt tgggcgttta tcgaagtgag gtgactgaat    240
ttgccgacaa tccaatatac cttgttcaat atcttttagt tttgcatac ttttttcctt     300
tttttgcgat caggatcgca gaaaaagtgc ggtcaatttt acaaacaaat ttttcctttt    360
cacaatgtcg tcgctaacaa aggcttaata aaaggaaaat gaatgaaact aacaacacag    420
caaaccttga aaaaagggtt tacattaata gagctaatga ttgtgattgc aattattgct    480
attttagcca ctatcgcaat tccctcttat caaaattata ctaaaaaagc agcggtatct    540
gaattactgc aagcgtcagc gccttataag gctgatgtgg aattatgtgt atatagcaca    600
aatgaaacaa caaactgtac gggtggaaaa aatggtattg cagcagatat aaccacagca    660
aaaggctatg taaaatcagt gacaacaagc aacggtgcaa taacagtaaa aggggatggc    720
acattggcaa atatggaata tattttgcaa gctacaggta atgctgcaac aggtgtaact    780
tggacaacaa cttgcaaagg aacggatgcc tctttatttc cagcaaattt ttgcggaagt    840
gtcacacaat gacgagctat gctttacttc atactcagcg tgtaaccgct caaaatggcg    900
agatctttac gatctcgcca gatttatggg aacgcaatca gcagcaacaa tccttgctct    960
tgcggtattt tgctttgcca cttaaagaag aaaataatcg tctttggcta ggggttgatt   1020
ctctctccaa tctttcagct tgtgaaacca ttgcgtttat aacaggaaaa cctgtcgaac   1080
caattttgtt agaaagcagc caactcaaag aactgttaca acaacttact ccgcaccaaa   1140
tgcaagtgga agagcaagtt aaattctatc aacatcaaga aacccatttt gaacaagaag   1200
atgatgaacc tgttatccgc ttacttaatc agatttttga atctgcctta caaaaaaatg   1260
cctctgatat tcatttagaa accttggctg atcagtttca agtgcggttt agaattgatg   1320
gtgttttaca accacaaccc ttaataagca aaatattcgc caatcgtatt atttcacgct   1380
taaaattact ggctaaatta gatattagtg aaaatcgact tccacaagat ggacgatttc   1440
aatttaaaac cactttttcc gatattcttg attttcgcct ttcaacctta ccaacccatt   1500
ggggcgaaaa aatcgtgttg cgagcgcaac aaaataaacc tgtagaactt agctttgctg   1560
aactgggtat gaccgaaaat cagcaacaag catttcaacg ctcacttagc cagccacaag   1620
gattaatttt agtaaccggc cccacaggaa gtgggaaaag tatctcgctt tacaccgcac   1680
ttcagtggct aaatacgcct gataaacata ttatgaccgc tgaagatccc attgaaattg   1740
aacttgatgg tattattcaa agccaaatta atccgcagat tggattagat tttagccgtc   1800
tattgcgtgc ttttttacgt caagatcccg acatcattat gctaggtgaa attcgagatg   1860
aagaaagtgc aaggattgca ctacgtgccg ctcaaacggg acatttggtg ctttcaactt   1920
tacataccaa tgatgcaata tctgccattt ctcgcttaca acaactcggt attcaacaac   1980
atgaaattga aaacagttta ctactcgtca ttgcacagcg tcttgtacga aaaatctgtc   2040
```

```
caaagtgcgg tggaaattta ataaattctt gtgattgcca tcaaggttat cgagggcgaa   2100

tcggcgtgta tcaatttcta cattggcaac agaatggcta tcaaacggat tttgagaatt   2160

tacgagagag tggtttggaa aaagttagcc aaggcataac agatgagaaa gaaattgaac   2220

gtgtgttagg taaaaactca tgactaaaaa actcttttat tatcaaggta gtaacgcatt   2280

aaatcagaaa caaaaaggct caattattgc ggatacgaaa caacaagcgc actttcagtt   2340

aataagccgc gggcttactc acatcaaatt acaacaaaac tggcaatttg gggcaaaacc   2400

caaaaattca gaaatcagtg aattactcaa tcaattagcg acattgctac agtccgtaat   2460

tccgttaaaa aacagcctac aaattttgca acaaaattgt actcaaatta tgctcaacaa   2520

atggcttgaa cgactgcttc aatccattga atctggctta gcattctcac aagccattga   2580

acaacaagga aaatatctca cacaacaaga aattcaactg attcaagtgg gagaaatgac   2640

aggaaaactt gccgtagttt gtaaaaaaat agccacgcac cgtagtcaat ctttggcttt   2700

acaacgcaaa ttacagaaaa ttatgttata tccctcaatg gtattgggaa tttctctatt   2760

attgacactc gcattactgc tttttatcgc gcctcaattt gctgaaatgt acagtggcaa   2820

taatgcggag ttaccaacaa taaccgcaat attgctctca atatctaatt tccttaagca   2880

aaatattggc attttgctat ttttcgtttt gagttttttt ctattttatt atttctatct   2940

aaaacgccag acttggtttc atcaaaagaa aaatcaactt atttctatca cgcctatttt   3000

tggcacaatt caaaagcttt cacgtttagt gaactttagt caaagtttac aaattatgtt   3060

gcaggccggc gtaccgctta atcaggcact agacagtttt cttcctcgca cacaaacttg   3120

gcaaaccaag aaaacgcttg taaacgatat ggtattagat aaagaagtgc ggtcaatttt   3180

gcaatgggtt tctcaaggct atgcgttttc taatagcgta agtagcgatc ttttcccgat   3240

ggaagcacaa caaatgctac aaattggcga acaaagcgga aaactcgctt tgatgctaga   3300

gcatatcgca gataattacc aagaaaaact taatcatcaa attgacttac tctcacaaat   3360

gctagaacca ttaatgatgg taatcatcgg cagtctgatt gggattatta tgatgggaat   3420

gtatttacct atctttaata tgggatcagt tattca atg att tac ttc aca atg     3474
                                        Met Ile Tyr Phe Thr Met
                                        1               5

ttt tta tta ggc ggc atc tta ggg atc gca ttg tgg ttc tac cta tct     3522
Phe Leu Leu Gly Gly Ile Leu Gly Ile Ala Leu Trp Phe Tyr Leu Ser
            10                  15                  20

ggt ttt att acg cat ttg cag caa gag att tat gcg act tac gtt gaa     3570
Gly Phe Ile Thr His Leu Gln Gln Glu Ile Tyr Ala Thr Tyr Val Glu
        25                  30                  35

tta ttt cca caa aac agt tct cca ttt caa ccg cac ttt gcc tct att     3618
Leu Phe Pro Gln Asn Ser Ser Pro Phe Gln Pro His Phe Ala Ser Ile
    40                  45                  50

caa caa aaa aag tgc ggt cat att ttg agg tat ttt ttt agt att ggg     3666
Gln Gln Lys Lys Cys Gly His Ile Leu Arg Tyr Phe Phe Ser Ile Gly
55                  60                  65                  70

gtt gga ttt ata ttt tta caa att gcc ttc aaa gat tct att ttt act     3714
Val Gly Phe Ile Phe Leu Gln Ile Ala Phe Lys Asp Ser Ile Phe Thr
                75                  80                  85

gta tgg atc gga ctc aca ctt att att ctt tgg aca atc agt tat ctt     3762
Val Trp Ile Gly Leu Thr Leu Ile Ile Leu Trp Thr Ile Ser Tyr Leu
            90                  95                  100

gat tgg cac tat caa ctt att tct acg aca ccc tgt tta tgg tta ctt     3810
Asp Trp His Tyr Gln Leu Ile Ser Thr Thr Pro Cys Leu Trp Leu Leu
        105                 110                 115
```

```
act ctc ggt tta ttt ggc gca gac aat aac ttt tca ttg cta acg tta     3858
Thr Leu Gly Leu Phe Gly Ala Asp Asn Asn Phe Ser Leu Leu Thr Leu
    120                 125                 130

tct gaa agc ata aaa agt gcg gct agt ttt ttt att gtt ttc tac gca     3906
Ser Glu Ser Ile Lys Ser Ala Ala Ser Phe Phe Ile Val Phe Tyr Ala
135                 140                 145                 150

atc tat tgg att gca aaa tgt tat tat aga aaa gaa gcc ttt gga cgg     3954
Ile Tyr Trp Ile Ala Lys Cys Tyr Tyr Arg Lys Glu Ala Phe Gly Arg
                155                 160                 165

gga gat tat tgg cta gca atg gca tta gga agt ttt att cat tta gaa     4002
Gly Asp Tyr Trp Leu Ala Met Ala Leu Gly Ser Phe Ile His Leu Glu
            170                 175                 180

acc tta ccg cac ttt tta tta tta gcc tca gtg ctt gga ata tgt ttt     4050
Thr Leu Pro His Phe Leu Leu Leu Ala Ser Val Leu Gly Ile Cys Phe
        185                 190                 195

tcg ctt att cat aaa aag aaa aaa gaa ttt ata cct ttt gcc cct ttt     4098
Ser Leu Ile His Lys Lys Lys Lys Glu Phe Ile Pro Phe Ala Pro Phe
    200                 205                 210

atg aac tta tcg gct atc att att tat ctc gtc aaa tat tac gga tat     4146
Met Asn Leu Ser Ala Ile Ile Ile Tyr Leu Val Lys Tyr Tyr Gly Tyr
215                 220                 225                 230

taa aaaggggaaa acataatatt tttcccttgt tcttcataga agtgcggttg         4199

tttttacgaa cgtttcatca cttcaaaaaa ctcttcgttg gttttcgcca tcatcagctt   4259

atcaatcaag aattccattg catccacttc atccattgga ttaagaatct tacgaagaat   4319

ccacattttt tgtaattcgt ccgctg                                        4345


<210> SEQ ID NO 8
<211> LENGTH: 230
<212> TYPE: PRT
<213> ORGANISM: H. influenzae

<400> SEQUENCE: 8

Met Ile Tyr Phe Thr Met Phe Leu Leu Gly Gly Ile Leu Gly Ile Ala
1               5                   10                  15

Leu Trp Phe Tyr Leu Ser Gly Phe Ile Thr His Leu Gln Gln Glu Ile
            20                  25                  30

Tyr Ala Thr Tyr Val Glu Leu Phe Pro Gln Asn Ser Ser Pro Phe Gln
        35                  40                  45

Pro His Phe Ala Ser Ile Gln Gln Lys Lys Cys Gly His Ile Leu Arg
    50                  55                  60

Tyr Phe Phe Ser Ile Gly Val Gly Phe Ile Phe Leu Gln Ile Ala Phe
65                  70                  75                  80

Lys Asp Ser Ile Phe Thr Val Trp Ile Gly Leu Thr Leu Ile Ile Leu
                85                  90                  95

Trp Thr Ile Ser Tyr Leu Asp Trp His Tyr Gln Leu Ile Ser Thr Thr
            100                 105                 110

Pro Cys Leu Trp Leu Leu Thr Leu Gly Leu Phe Gly Ala Asp Asn Asn
        115                 120                 125

Phe Ser Leu Leu Thr Leu Ser Glu Ser Ile Lys Ser Ala Ala Ser Phe
    130                 135                 140

Phe Ile Val Phe Tyr Ala Ile Tyr Trp Ile Ala Lys Cys Tyr Tyr Arg
145                 150                 155                 160

Lys Glu Ala Phe Gly Arg Gly Asp Tyr Trp Leu Ala Met Ala Leu Gly
                165                 170                 175

Ser Phe Ile His Leu Glu Thr Leu Pro His Phe Leu Leu Leu Ala Ser
            180                 185                 190
```

```
Val Leu Gly Ile Cys Phe Ser Leu Ile His Lys Lys Lys Lys Glu Phe
        195                 200                 205

Ile Pro Phe Ala Pro Phe Met Asn Leu Ser Ala Ile Ile Ile Tyr Leu
    210                 215                 220

Val Lys Tyr Tyr Gly Tyr
225                 230


<210> SEQ ID NO 9
<211> LENGTH: 4864
<212> TYPE: DNA
<213> ORGANISM: H. influenzae
<220> FEATURE:
<221> NAME/KEY: CDS
<222> LOCATION: (517)..(1314)

<400> SEQUENCE: 9

tacgaataat ggtttttct ggggttaaga aaaagttacg cgctaattgt tgagtaatcg      60

tacttgcacc ttgtgatgca ccgccattac tcactgcgac aaacaatgca cgagcaatgc     120

cgatagggtc taatccgtga tgatcgtaaa aacgattgtc ttccgttgct aaaaatgcgt     180

caattaagcg ttgtggcaca tcggctaatt tcactggaat acggcgttgc tcgcccactt     240

cgccaattaa tttaccgtca gccgtataaa tctgcattgg ttgttgtaat tcaacggttc     300

ttaatgtttc tactgagggc aattccgatt ttaggtggaa atacaacatt ccgccagcca     360

ctaaacctaa aatacataaa gttaataggg tgtttaatat taattttgcg atccgcatcg     420

taaaattctc gcttggttaa tgaatattct tgtcaagaga cctatgattt agttgttaag     480

tataaaagat tcagccttta aagaatagga aagaat atg caa ttc tcc ctg aaa       534
                                        Met Gln Phe Ser Leu Lys
                                        1               5

aat tac cgc act tta caa atc ggc att cat cgt aag cag ggt tat ttt       582
Asn Tyr Arg Thr Leu Gln Ile Gly Ile His Arg Lys Gln Gly Tyr Phe
            10                  15                  20

gat ttt gtg tgg ttt gat gat ctt gaa cag cca caa agt tat caa att       630
Asp Phe Val Trp Phe Asp Asp Leu Glu Gln Pro Gln Ser Tyr Gln Ile
        25                  30                  35

ttt gtt aat gat cgt gat ttt aaa aat cgt ttt tta caa cag cta aaa       678
Phe Val Asn Asp Arg Asp Phe Lys Asn Arg Phe Leu Gln Gln Leu Lys
    40                  45                  50

aca caa tat caa ggg aaa acc ttt cct tta cag ttt gtg gca agc att       726
Thr Gln Tyr Gln Gly Lys Thr Phe Pro Leu Gln Phe Val Ala Ser Ile
55                  60                  65                  70

ccc gct cac tta act tgg tcg aaa gta tta atg ttg cca caa gtg tta       774
Pro Ala His Leu Thr Trp Ser Lys Val Leu Met Leu Pro Gln Val Leu
                75                  80                  85

aat gcg caa gaa tgt cat caa caa tgt aaa ttt gtg att gaa aaa gag       822
Asn Ala Gln Glu Cys His Gln Gln Cys Lys Phe Val Ile Glu Lys Glu
            90                  95                  100

ctg cct att tct tta aat gaa tta tgg ttt gat tat cgt tct acc tcg       870
Leu Pro Ile Ser Leu Asn Glu Leu Trp Phe Asp Tyr Arg Ser Thr Ser
        105                 110                 115

tta aag caa ggt ttt cga tta gac gtt act gca att cgt aaa agt act       918
Leu Lys Gln Gly Phe Arg Leu Asp Val Thr Ala Ile Arg Lys Ser Thr
    120                 125                 130

gct caa act tat ttg caa gat ttt cag cca ttt aaa att aat gta ttg       966
Ala Gln Thr Tyr Leu Gln Asp Phe Gln Pro Phe Lys Ile Asn Val Leu
135                 140                 145                 150

gat gtt gcg tca aat gct att ttg cgt gca ttt cag tat ttg ttg aat      1014
Asp Val Ala Ser Asn Ala Ile Leu Arg Ala Phe Gln Tyr Leu Leu Asn
```

```
            155                 160                 165

gaa caa gtg cgg tca gaa aat acc tta ttt tta ttt caa gaa gat gac     1062
Glu Gln Val Arg Ser Glu Asn Thr Leu Phe Leu Phe Gln Glu Asp Asp
        170                 175                 180

tat tgt ttg gcg atc tgt gaa aga tcg cag caa tcg caa att tta caa     1110
Tyr Cys Leu Ala Ile Cys Glu Arg Ser Gln Gln Ser Gln Ile Leu Gln
    185                 190                 195

tct cac gaa aat ttg acc gca ctt tat gaa caa ttt acc gaa cgt ttt     1158
Ser His Glu Asn Leu Thr Ala Leu Tyr Glu Gln Phe Thr Glu Arg Phe
200                 205                 210

gaa gga caa ctt gaa caa gtt ttt gtt tat caa att ccc tca agt cat     1206
Glu Gly Gln Leu Glu Gln Val Phe Val Tyr Gln Ile Pro Ser Ser His
215                 220                 225                 230

aca cca tta ccc gaa aac tgg cag cga gta gaa aca gaa ctc cct ttt     1254
Thr Pro Leu Pro Glu Asn Trp Gln Arg Val Glu Thr Glu Leu Pro Phe
                235                 240                 245

att gcg ctt ggc aac gcg cta tgg caa aaa gat tta cat caa caa aaa     1302
Ile Ala Leu Gly Asn Ala Leu Trp Gln Lys Asp Leu His Gln Gln Lys
        250                 255                 260

gtg ggt ggt taa atgtcgatga atttattgcc ttggcgtact tatcaacatc         1354
Val Gly Gly
    265

aaaagcgttt acgtcgttta gctttttata tcgctttatt tatcttgctt gctattaatt   1414

taatgttggc ttttagcaat ttgattgaac aacagaaaca aaatttgcaa gcgcagcaaa   1474

catcttttga acaacttaat cagcaacttc acaaaactac catgcaaatt gatcagttac   1534

gcagtgcggt gaaagttggt gaagttttga catctattcc caacgagcaa gtaaaaaaga   1594

gtttacaaca gctaagtgaa ttaccttttc aacaaggaga actgaataaa tttaaacaag   1654

atgccaataa cttaagtttg gaaggtaacg cgcaagatca aacagaattt gaactgattc   1714

atcaattttt aaagaaacat tttcccaatg tgaaattaag tcaggttcaa cctgaacaag   1774

atacattgtt ttttcacttt gatgtggaac aaggggcgga aaaatgaaag ctttttttaa   1834

cgatcctttt actccttttg gaaaatggct aagtcagcct tttatgtgc acggtttaac    1894

ctttttattg ctattaagtg cggtgatttt tcgccccgtt ttagattata tcgaggggag   1954

ttcacgtttc catgaaattg aaaatgagtt agcggtgaaa cgttcagaat tgttgcatca   2014

acagaaaatt ttaacttctt tacagcagca gtcggaaagt cgaaaacttt ctccagaact   2074

ggctgcacaa attattcctt tgaataaaca aattcaacgt ttagctgcgc gtaacggttt   2134

atctcagcat ttacgttggg aaatggggca aaagcctatt ttgcatttac agcttacagg   2194

tcattttgag aaaacgaaga catttttaac cgcacttttg gctaattcgt cacagctttc   2254

agtgagtcgc ttgcagttta tcaaacccga agacaaccca ttgcaaaccg agatcatttt   2314

tcagctagat aaggaaacaa aatgaaacat tggtttttcc tgattatatt attttttatg   2374

aattgcagtt ggggacaaga tcctttcgat aaaacacagc gtaaccgttc tcagtttgat   2434

aacgcacaaa cagtaatgga gcagacagaa ataatttcct cagatgtacc taataatcta   2494

tgcggagcgg atgaaaatcg ccaagcggct gaaattcctt tgaacgcttt aaaattggtg   2554

ggcgtagtga tttctaaaga taaagccttt gccttgttgc aagatcaagg tttgcaaatt   2614

tacagcgttt tagagggcgt tgatgtggct caagagggct atattgtaga aaaaatcaac   2674

caaaacaatg ttcaatttat gcgtaagctc ggagagcaat gtgatagtag tgaatggaaa   2734

aaattaagtt tttaaaggaa gattatgaag aaatattttt taaagtgcgg ttattttta    2794

gtgtgttttt gtttgccatt aatcgttttt gctaatccta aaacagataa cgaatgtttt   2854
```

```
tttattcgtt tatcgcaagc acctttagct caaacactgg agcaattagc ttttcaacaa   2914

gatgtgaatt tagtgatggg tgagaggtta gaaggcaata tttctttgaa attaaacaat   2974

attgatatgc cacgtttgct aaaaataatc gcaaaaagta agcatcttac tttgaataaa   3034

gatgatgggg tttattattt aaacggcagt caatctggca aaggtcaagt tgcaggaaat   3094

cttacgacaa atgaaccgca cttagtcagc cacacggtaa aacttcattt tgctaaagcc   3154

tctgaattaa tgaaatcctt aacaacagga agtggatctt tgctttcttc tgcggggagc   3214

attacctttg atgatcgcag taatttgctg gttattcagg atgaacctcg ttttgtgcaa   3274

aatatcaaaa aactgattgc tgaaatggat aagcctattg aacagatcgc tattgaagcg   3334

cgaattgtga caattacgga tgagagtttg aaagaacttg gcgttcggtg ggggattttt   3394

aatccaactg aaaatgcaag acgagttgcg ggcagcctta caggcaatag ctttgaaaat   3454

attgcggata atcttaatgt aaattttgcg acaacgacga cacctgctgg ctctatagca   3514

ttacaagtcg cgaaaattaa tgggcgattg cttgatttag aattgagtgc gttggagcgt   3574

gaaaataatg tagaaattat tgcaagtcct cgcttactca ctaccaataa gaaaagtgcg   3634

agcattaaac aggggacaga aattccttac atcgtgagta atactcgtaa cgatacgcaa   3694

tctgtggaat ttcgtgaggc agtacttggt ttggaagtga cgccacatat ttctaaagat   3754

aacaatatct tacttgattt attggtaagt caaaattccc ctggttctcg tgtcgcttat   3814

ggacaaaatg aggtggtttc tattgataag caagaaatta atactcaggt ttttgccaaa   3874

gatggggaaa ccattgtgct tggcggcgta tttcacgaca caatcacgaa aagcgaagat   3934

aaagtgccat tgcttggcga tatacccgtt attaaacgat tatttagcaa agaaagtgaa   3994

cgacatcaaa aacgtgagct cgtgattttc gtcacgccgc atattttaaa agcaggagaa   4054

acgttagagg cgttgaaaca aaaaagtgcg gggaaaaaat aactttttta gacgatgaat   4114

ttttttaatt ttcgctgtat ccactgtcgt ggcaatcttc atattgcaaa aaatgggcta   4174

tgttcaggtt gccaaaaaca aattaaatct tttccttatt gcggtcattg tggtgcggaa   4234

ttgcaatatt atgcgcagca ttgtggtaat tgtcttaaac aagaaccaag ttgggataag   4294

atggtcatta ttgggcatta tattgaacct ctttcgatat tgattcaccg ttttaaattt   4354

caaaatcaat tttggattga ccgcacttta gctcggcttt tatatcttgc ggtgcgtgat   4414

gctaaacgaa cgcatcaact taaattgcca gaagcaatca ttccagtgcc tttatatcat   4474

tttcgtcagt ggcgacgggg ttataatcag gcagatttat tatctcggca attaagtcgc   4534

tggctggata ttcctaattt gagcaatatc gtaaagcgtg tgaaacacac ctatactcaa   4594

cgtggtttga gtgcaaaaga tcgtcgtcag aatttaaaaa atgccttttc tcttgttgtt   4654

tcgaaaaatg aatttcctta tcgccgtgtt gcgttggtgg atgatgtgat tactactggt   4714

tctacactca atgaaatctc aaaattgttg cgaaaattag gtgtggagga gattcaagtg   4774

tgggggctgg cacgagctta atataaagca ctggaaaaaa aagcgcgata agcgtattat   4834

tcccgatact ttctctcaag tatttaggac                                    4864
```

<210> SEQ ID NO 10
<211> LENGTH: 265
<212> TYPE: PRT
<213> ORGANISM: H. influenzae

<400> SEQUENCE: 10

```
Met Gln Phe Ser Leu Lys Asn Tyr Arg Thr Leu Gln Ile Gly Ile His
1               5                   10                  15
```

```
Arg Lys Gln Gly Tyr Phe Asp Phe Val Trp Phe Asp Asp Leu Glu Gln
            20                  25                  30

Pro Gln Ser Tyr Gln Ile Phe Val Asn Asp Arg Asp Phe Lys Asn Arg
        35                  40                  45

Phe Leu Gln Gln Leu Lys Thr Gln Tyr Gln Gly Lys Thr Phe Pro Leu
    50                  55                  60

Gln Phe Val Ala Ser Ile Pro Ala His Leu Thr Trp Ser Lys Val Leu
65                  70                  75                  80

Met Leu Pro Gln Val Leu Asn Ala Gln Glu Cys His Gln Gln Cys Lys
                85                  90                  95

Phe Val Ile Glu Lys Glu Leu Pro Ile Ser Leu Asn Glu Leu Trp Phe
            100                 105                 110

Asp Tyr Arg Ser Thr Ser Leu Lys Gln Gly Phe Arg Leu Asp Val Thr
        115                 120                 125

Ala Ile Arg Lys Ser Thr Ala Gln Thr Tyr Leu Gln Asp Phe Gln Pro
    130                 135                 140

Phe Lys Ile Asn Val Leu Asp Val Ala Ser Asn Ala Ile Leu Arg Ala
145                 150                 155                 160

Phe Gln Tyr Leu Leu Asn Glu Gln Val Arg Ser Glu Asn Thr Leu Phe
                165                 170                 175

Leu Phe Gln Glu Asp Asp Tyr Cys Leu Ala Ile Cys Glu Arg Ser Gln
            180                 185                 190

Gln Ser Gln Ile Leu Gln Ser His Glu Asn Leu Thr Ala Leu Tyr Glu
        195                 200                 205

Gln Phe Thr Glu Arg Phe Glu Gly Gln Leu Glu Gln Val Phe Val Tyr
    210                 215                 220

Gln Ile Pro Ser Ser His Thr Pro Leu Pro Glu Asn Trp Gln Arg Val
225                 230                 235                 240

Glu Thr Glu Leu Pro Phe Ile Ala Leu Gly Asn Ala Leu Trp Gln Lys
                245                 250                 255

Asp Leu His Gln Gln Lys Val Gly Gly
            260                 265
```

<210> SEQ ID NO 11
<211> LENGTH: 4864
<212> TYPE: DNA
<213> ORGANISM: H. influenzae
<220> FEATURE:
<221> NAME/KEY: CDS
<222> LOCATION: (1321)..(1821)

<400> SEQUENCE: 11

```
tacgaataat ggtttttct ggggttaaga aaaagttacg cgctaattgt tgagtaatcg     60

tacttgcacc ttgtgatgca ccgccattac tcactgcgac aaacaatgca cgagcaatgc    120

cgatagggtc taatccgtga tgatcgtaaa aacgattgtc ttccgttgct aaaaatgcgt    180

caattaagcg ttgtggcaca tcggctaatt tcactggaat acggcgttgc tcgcccactt    240

cgccaattaa tttaccgtca gccgtataaa tctgcattgg ttgttgtaat tcaacggttc    300

ttaatgtttc tactgagggc aattccgatt ttaggtggaa atacaacatt ccgccagcca    360

ctaaacctaa aatacataaa gttaataggg tgtttaatat taattttgcg atccgcatcg    420

taaaattctc gcttggttaa tgaatattct tgtcaagaga cctatgattt agttgttaag    480

tataaaagat tcagccttta aagaatagga aagaatatgc aattctccct gaaaaattac    540

cgcactttac aaatcggcat tcatcgtaag cagggttatt ttgattttgt gtggtttgat    600
```

```
gatcttgaac agccacaaag ttatcaaatt tttgttaatg atcgtgattt taaaaatcgt    660

tttttacaac agctaaaaac acaatatcaa gggaaaacct ttcctttaca gtttgtggca    720

agcattcccg ctcacttaac ttggtcgaaa gtattaatgt tgccacaagt gttaaatgcg    780

caagaatgtc atcaacaatg taaatttgtg attgaaaaag agctgcctat ttctttaaat    840

gaattatggt ttgattatcg ttctacctcg ttaaagcaag gttttcgatt agacgttact    900

gcaattcgta aaagtactgc tcaaacttat ttgcaagatt ttcagccatt taaaattaat    960

gtattggatg ttgcgtcaaa tgctattttg cgtgcatttc agtatttgtt gaatgaacaa   1020

gtgcggtcag aaaatacctt atttttattt caagaagatg actattgttt ggcgatctgt   1080

gaaagatcgc agcaatcgca aattttacaa tctcacgaaa atttgaccgc actttatgaa   1140

caatttaccg aacgttttga aggacaactt gaacaagttt ttgtttatca aattccctca   1200

agtcatacac cattacccga aaactggcag cgagtagaaa cagaactccc ttttattgcg   1260

cttggcaacg cgctatggca aaaagattta catcaacaaa aagtgggtgg ttaaatgtcg   1320

atg aat tta ttg cct tgg cgt act tat caa cat caa aag cgt tta cgt     1368
Met Asn Leu Leu Pro Trp Arg Thr Tyr Gln His Gln Lys Arg Leu Arg
1               5                   10                  15

cgt tta gct ttt tat atc gct tta ttt atc ttg ctt gct att aat tta     1416
Arg Leu Ala Phe Tyr Ile Ala Leu Phe Ile Leu Leu Ala Ile Asn Leu
            20                  25                  30

atg ttg gct ttt agc aat ttg att gaa caa cag aaa caa aat ttg caa     1464
Met Leu Ala Phe Ser Asn Leu Ile Glu Gln Gln Lys Gln Asn Leu Gln
        35                  40                  45

gcg cag caa aca tct ttt gaa caa ctt aat cag caa ctt cac aaa act     1512
Ala Gln Gln Thr Ser Phe Glu Gln Leu Asn Gln Gln Leu His Lys Thr
    50                  55                  60

acc atg caa att gat cag tta cgc agt gcg gtg aaa gtt ggt gaa gtt     1560
Thr Met Gln Ile Asp Gln Leu Arg Ser Ala Val Lys Val Gly Glu Val
65                  70                  75                  80

ttg aca tct att ccc aac gag caa gta aaa aag agt tta caa cag cta     1608
Leu Thr Ser Ile Pro Asn Glu Gln Val Lys Lys Ser Leu Gln Gln Leu
                85                  90                  95

agt gaa tta cct ttt caa caa gga gaa ctg aat aaa ttt aaa caa gat     1656
Ser Glu Leu Pro Phe Gln Gln Gly Glu Leu Asn Lys Phe Lys Gln Asp
            100                 105                 110

gcc aat aac tta agt ttg gaa ggt aac gcg caa gat caa aca gaa ttt     1704
Ala Asn Asn Leu Ser Leu Glu Gly Asn Ala Gln Asp Gln Thr Glu Phe
        115                 120                 125

gaa ctg att cat caa ttt tta aag aaa cat ttt ccc aat gtg aaa tta     1752
Glu Leu Ile His Gln Phe Leu Lys Lys His Phe Pro Asn Val Lys Leu
    130                 135                 140

agt cag gtt caa cct gaa caa gat aca ttg ttt ttt cac ttt gat gtg     1800
Ser Gln Val Gln Pro Glu Gln Asp Thr Leu Phe Phe His Phe Asp Val
145                 150                 155                 160

gaa caa ggg gcg gaa aaa tga aagctttttt taacgatcct tttactcctt        1851
Glu Gln Gly Ala Glu Lys
                165

ttggaaaatg gctaagtcag ccttttttatg tgcacggttt aacctttta ttgctattaa   1911

gtgcggtgat ttttcgcccc gttttagatt atatcgaggg gagttcacgt ttccatgaaa   1971

ttgaaaatga gttagcggtg aaacgttcag aattgttgca tcaacagaaa attttaactt   2031

ctttacagca gcagtcggaa agtcgaaaac tttctccaga actggctgca caaattattc   2091

ctttgaataa acaaattcaa cgtttagctg cgcgtaacgg tttatctcag catttacgtt   2151
```

```
gggaaatggg gcaaaagcct attttgcatt tacagcttac aggtcatttt gagaaaacga   2211
agacattttt aaccgcactt ttggctaatt cgtcacagct ttcagtgagt cgcttgcagt   2271
ttatcaaacc cgaagacaac ccattgcaaa ccgagatcat ttttcagcta gataaggaaa   2331
caaaatgaaa cattggtttt tcctgattat attatttttt atgaattgca gttggggaca   2391
agatcctttc gataaaacac agcgtaaccg ttctcagttt gataacgcac aaacagtaat   2451
ggagcagaca gaaataattt cctcagatgt acctaataat ctatgcggag cggatgaaaa   2511
tcgccaagcg gctgaaattc ctttgaacgc tttaaaattg gtgggcgtag tgatttctaa   2571
agataaagcc tttgccttgt tgcaagatca aggtttgcaa atttacagcg ttttagaggg   2631
cgttgatgtg gctcaagagg gctatattgt agaaaaaatc aaccaaaaca atgttcaatt   2691
tatgcgtaag ctcggagagc aatgtgatag tagtgaatgg aaaaaattaa gtttttaaag   2751
gaagattatg aagaaatatt ttttaaagtg cggttatttt ttagtgtgtt tttgtttgcc   2811
attaatcgtt tttgctaatc ctaaaacaga taacgaatgt ttttttattc gtttatcgca   2871
agcaccttta gctcaaacac tggagcaatt agcttttcaa caagatgtga atttagtgat   2931
gggtgagagg ttagaaggca atatttcttt gaaattaaac aatattgata tgccacgttt   2991
gctaaaaata atcgcaaaaa gtaagcatct tactttgaat aaagatgatg gggtttatta   3051
tttaaacggc agtcaatctg gcaaaggtca agttgcagga aatcttacga caaatgaacc   3111
gcacttagtc agccacacgg taaaacttca ttttgctaaa gcctctgaat taatgaaatc   3171
cttaacaaca ggaagtggat ctttgctttc ttctgcgggg agcattacct ttgatgatcg   3231
cagtaatttg ctggttattc aggatgaacc tcgttttgtg caaaatatca aaaaactgat   3291
tgctgaaatg gataagccta ttgaacagat cgctattgaa gcgcgaattg tgacaattac   3351
ggatgagagt ttgaaagaac ttggcgttcg gtgggggatt tttaatccaa ctgaaaatgc   3411
aagacgagtt gcgggcagcc ttacaggcaa tagctttgaa aatattgcgg ataatcttaa   3471
tgtaaatttt gcgacaacga cgacacctgc tggctctata gcattacaag tcgcgaaaat   3531
taatgggcga ttgcttgatt tagaattgag tgcgttggag cgtgaaaata atgtagaaat   3591
tattgcaagt cctcgcttac tcactaccaa taagaaaagt gcgagcatta aacaggggac   3651
agaaattcct tacatcgtga gtaatactcg taacgatacg caatctgtgg aatttcgtga   3711
ggcagtactt ggtttggaag tgacgccaca tatttctaaa gataacaata tcttacttga   3771
tttattggta agtcaaaatt cccctggttc tcgtgtcgct tatggacaaa atgaggtggt   3831
ttctattgat aagcaagaaa ttaatactca ggtttttgcc aaagatgggg aaaccattgt   3891
gcttggcggc gtatttcacg acacaatcac gaaaagcgaa gataaagtgc cattgcttgg   3951
cgatataccc gttattaaac gattatttag caaagaaagt gaacgacatc aaaaacgtga   4011
gctcgtgatt ttcgtcacgc cgcatatttt aaaagcagga gaaacgttag aggcgttgaa   4071
acaaaaaagt gcggggaaaa aataactttt ttagacgatg aatttttta attttcgctg   4131
tatccactgt cgtggcaatc ttcatattgc aaaaaatggg ctatgttcag gttgccaaaa   4191
acaaattaaa tcttttcctt attgcggtca ttgtggtgcg gaattgcaat attatgcgca   4251
gcattgtggt aattgtctta aacaagaacc aagttgggat aagatggtca ttattgggca   4311
ttatattgaa cctctttcga tattgattca ccgttttaaa tttcaaaatc aattttggat   4371
tgaccgcact ttagctcggc ttttatatct tgcggtgcgt gatgctaaac gaacgcatca   4431
acttaaattg ccagaagcaa tcattccagt gcctttatat cattttcgtc agtggcgacg   4491
gggttataat caggcagatt tattatctcg gcaattaagt cgctggctgg atattcctaa   4551
```

```
tttgagcaat atcgtaaagc gtgtgaaaca cacctatact caacgtggtt tgagtgcaaa   4611

agatcgtcgt cagaatttaa aaaatgcctt ttctcttgtt gtttcgaaaa atgaatttcc   4671

ttatcgccgt gttgcgttgg tggatgatgt gattactact ggttctacac tcaatgaaat   4731

ctcaaaattg ttgcgaaaat taggtgtgga ggagattcaa gtgtgggggc tggcacgagc   4791

ttaatataaa gcactggaaa aaaaagcgcg ataagcgtat tattcccgat actttctctc   4851

aagtatttag gac                                                      4864
```

```
<210> SEQ ID NO 12
<211> LENGTH: 166
<212> TYPE: PRT
<213> ORGANISM: H. influenzae

<400> SEQUENCE: 12

Met Asn Leu Leu Pro Trp Arg Thr Tyr Gln His Gln Lys Arg Leu Arg
1               5                   10                  15

Arg Leu Ala Phe Tyr Ile Ala Leu Phe Ile Leu Leu Ala Ile Asn Leu
            20                  25                  30

Met Leu Ala Phe Ser Asn Leu Ile Glu Gln Gln Lys Gln Asn Leu Gln
        35                  40                  45

Ala Gln Gln Thr Ser Phe Glu Gln Leu Asn Gln Gln Leu His Lys Thr
    50                  55                  60

Thr Met Gln Ile Asp Gln Leu Arg Ser Ala Val Lys Val Gly Glu Val
65                  70                  75                  80

Leu Thr Ser Ile Pro Asn Glu Gln Val Lys Lys Ser Leu Gln Gln Leu
                85                  90                  95

Ser Glu Leu Pro Phe Gln Gln Gly Glu Leu Asn Lys Phe Lys Gln Asp
            100                 105                 110

Ala Asn Asn Leu Ser Leu Glu Gly Asn Ala Gln Asp Gln Thr Glu Phe
        115                 120                 125

Glu Leu Ile His Gln Phe Leu Lys Lys His Phe Pro Asn Val Lys Leu
    130                 135                 140

Ser Gln Val Gln Pro Glu Gln Asp Thr Leu Phe Phe His Phe Asp Val
145                 150                 155                 160

Glu Gln Gly Ala Glu Lys
                165
```

```
<210> SEQ ID NO 13
<211> LENGTH: 4864
<212> TYPE: DNA
<213> ORGANISM: H. influenzae
<220> FEATURE:
<221> NAME/KEY: CDS
<222> LOCATION: (1818)..(2339)

<400> SEQUENCE: 13

tacgaataat ggtttttttct ggggttaaga aaaagttacg cgctaattgt tgagtaatcg     60

tacttgcacc ttgtgatgca ccgccattac tcactgcgac aaacaatgca cgagcaatgc    120

cgatagggtc taatccgtga tgatcgtaaa aacgattgtc ttccgttgct aaaaatgcgt    180

caattaagcg ttgtggcaca tcggctaatt tcactggaat acggcgttgc tcgcccactt    240

cgccaattaa tttaccgtca gccgtataaa tctgcattgg ttgttgtaat tcaacggttc    300

ttaatgtttc tactgagggc aattccgatt ttaggtggaa atacaacatt ccgccagcca    360

ctaaacctaa aatacataaa gttaataggg tgtttaatat taattttgcg atccgcatcg    420
```

```
taaaattctc gcttggttaa tgaatattct tgtcaagaga cctatgattt agttgttaag    480

tataaaagat tcagccttta aagaatagga aagaatatgc aattctccct gaaaaattac    540

cgcactttac aaatcggcat tcatcgtaag cagggttatt ttgattttgt gtggtttgat    600

gatcttgaac agccacaaag ttatcaaatt tttgttaatg atcgtgattt taaaaatcgt    660

tttttacaac agctaaaaac acaatatcaa gggaaaacct ttcctttaca gtttgtggca    720

agcattcccg ctcacttaac ttggtcgaaa gtattaatgt tgccacaagt gttaaatgcg    780

caagaatgtc atcaacaatg taaatttgtg attgaaaaag agctgcctat ttctttaaat    840

gaattatggt ttgattatcg ttctacctcg ttaaagcaag gttttcgatt agacgttact    900

gcaattcgta aaagtactgc tcaaacttat ttgcaagatt ttcagccatt taaaattaat    960

gtattggatg ttgcgtcaaa tgctattttg cgtgcatttc agtatttgtt gaatgaacaa   1020

gtgcggtcag aaaatacctt atttttattt caagaagatg actattgttt ggcgatctgt   1080

gaaagatcgc agcaatcgca aattttacaa tctcacgaaa atttgaccgc actttatgaa   1140

caatttaccg aacgttttga aggacaactt gaacaagttt ttgtttatca aattccctca   1200

agtcatacac cattacccga aaactggcag cgagtagaaa cagaactccc ttttattgcg   1260

cttggcaacg cgctatggca aaaagattta catcaacaaa aagtgggtgg ttaaatgtcg   1320

atgaatttat tgccttggcg tacttatcaa catcaaaagc gtttacgtcg tttagctttt   1380

tatatcgctt tatttatctt gcttgctatt aatttaatgt tggcttttag caatttgatt   1440

gaacaacaga aacaaaattt gcaagcgcag caaacatctt ttgaacaact taatcagcaa   1500

cttcacaaaa ctaccatgca aattgatcag ttacgcagtg cggtgaaagt tggtgaagtt   1560

ttgacatcta ttcccaacga gcaagtaaaa aagagtttac aacagctaag tgaattacct   1620

tttcaacaag gagaactgaa taaatttaaa caagatgcca ataacttaag tttggaaggt   1680

aacgcgcaag atcaaacaga atttgaactg attcatcaat tttaaagaa acattttccc    1740

aatgtgaaat taagtcaggt tcaacctgaa caagatacat tgttttttca ctttgatgtg   1800

gaacaagggg cggaaaa atg aaa gct ttt ttt aac gat cct ttt act cct      1850
                   Met Lys Ala Phe Phe Asn Asp Pro Phe Thr Pro
                   1               5                   10

ttt gga aaa tgg cta agt cag cct ttt tat gtg cac ggt tta acc ttt     1898
Phe Gly Lys Trp Leu Ser Gln Pro Phe Tyr Val His Gly Leu Thr Phe
            15                  20                  25

tta ttg cta tta agt gcg gtg att ttt cgc ccc gtt tta gat tat atc     1946
Leu Leu Leu Leu Ser Ala Val Ile Phe Arg Pro Val Leu Asp Tyr Ile
        30                  35                  40

gag ggg agt tca cgt ttc cat gaa att gaa aat gag tta gcg gtg aaa     1994
Glu Gly Ser Ser Arg Phe His Glu Ile Glu Asn Glu Leu Ala Val Lys
    45                  50                  55

cgt tca gaa ttg ttg cat caa cag aaa att tta act tct tta cag cag     2042
Arg Ser Glu Leu Leu His Gln Gln Lys Ile Leu Thr Ser Leu Gln Gln
60                  65                  70                  75

cag tcg gaa agt cga aaa ctt tct cca gaa ctg gct gca caa att att     2090
Gln Ser Glu Ser Arg Lys Leu Ser Pro Glu Leu Ala Ala Gln Ile Ile
                80                  85                  90

cct ttg aat aaa caa att caa cgt tta gct gcg cgt aac ggt tta tct     2138
Pro Leu Asn Lys Gln Ile Gln Arg Leu Ala Ala Arg Asn Gly Leu Ser
            95                  100                 105

cag cat tta cgt tgg gaa atg ggg caa aag cct att ttg cat tta cag     2186
Gln His Leu Arg Trp Glu Met Gly Gln Lys Pro Ile Leu His Leu Gln
        110                 115                 120

ctt aca ggt cat ttt gag aaa acg aag aca ttt tta acc gca ctt ttg     2234
```

-continued

```
Leu Thr Gly His Phe Glu Lys Thr Lys Thr Phe Leu Thr Ala Leu Leu
    125                 130                 135

gct aat tcg tca cag ctt tca gtg agt cgc ttg cag ttt atc aaa ccc     2282
Ala Asn Ser Ser Gln Leu Ser Val Ser Arg Leu Gln Phe Ile Lys Pro
140                 145                 150                 155

gaa gac aac cca ttg caa acc gag atc att ttt cag cta gat aag gaa     2330
Glu Asp Asn Pro Leu Gln Thr Glu Ile Ile Phe Gln Leu Asp Lys Glu
                160                 165                 170

aca aaa tga aacattggtt tttcctgatt atattatttt ttatgaattg             2379
Thr Lys

cagttgggga caagatcctt tcgataaaac acagcgtaac cgttctcagt ttgataacgc   2439

acaaacagta atggagcaga cagaaataat ttcctcagat gtacctaata atctatgcgg   2499

agcggatgaa aatcgccaag cggctgaaat tcctttgaac gctttaaaat tggtgggcgt   2559

agtgatttct aaagataaag cctttgcctt gttgcaagat caaggtttgc aaatttacag   2619

cgttttagag ggcgttgatg tggctcaaga gggctatatt gtagaaaaaa tcaaccaaaa   2679

caatgttcaa tttatgcgta agctcggaga gcaatgtgat agtagtgaat ggaaaaaatt   2739

aagtttttaa aggaagatta tgaagaaata tttttaaag tgcggttatt ttttagtgtg    2799

tttttgtttg ccattaatcg tttttgctaa tcctaaaaca gataacgaat gttttttat    2859

tcgtttatcg caagcacctt tagctcaaac actggagcaa ttagcttttc aacaagatgt   2919

gaatttagtg atgggtgaga ggttagaagg caatatttct ttgaaattaa acaatattga   2979

tatgccacgt ttgctaaaaa taatcgcaaa aagtaagcat cttactttga ataaagatga   3039

tggggtttat tatttaaacg gcagtcaatc tggcaaaggt caagttgcag gaaatcttac   3099

gacaaatgaa ccgcacttag tcagccacac ggtaaaactt cattttgcta aagcctctga   3159

attaatgaaa tccttaacaa caggaagtgg atctttgctt tcttctgcgg ggagcattac   3219

ctttgatgat cgcagtaatt tgctggttat tcaggatgaa cctcgttttg tgcaaaatat   3279

caaaaaactg attgctgaaa tggataagcc tattgaacag atcgctattg aagcgcgaat   3339

tgtgacaatt acggatgaga gtttgaaaga acttggcgtt cggtggggga tttttaatcc   3399

aactgaaaat gcaagacgag ttgcgggcag ccttacaggc aatagctttg aaaatattgc   3459

ggataatctt aatgtaaatt ttgcgacaac gacgacacct gctggctcta tagcattaca   3519

agtcgcgaaa attaatgggc gattgcttga tttagaattg agtgcgttgg agcgtgaaaa   3579

taatgtagaa attattgcaa gtcctcgctt actcactacc aataagaaaa gtgcgagcat   3639

taaacagggg acagaaattc cttacatcgt gagtaatact cgtaacgata cgcaatctgt   3699

ggaatttcgt gaggcagtac ttggtttgga agtgacgcca catatttcta aagataacaa   3759

tatcttactt gatttattgg taagtcaaaa ttcccctggt tctcgtgtcg cttatggaca   3819

aaatgaggtg gtttctattg ataagcaaga aattaatact caggtttttg ccaaagatgg   3879

ggaaaccatt gtgcttggcg gcgtatttca cgacacaatc acgaaaagcg aagataaagt   3939

gccattgctt ggcgatatac ccgttattaa acgattattt agcaaagaaa gtgaacgaca   3999

tcaaaaacgt gagctcgtga ttttcgtcac gccgcatatt ttaaaagcag gagaaacgtt   4059

agaggcgttg aaacaaaaaa gtgcggggaa aaaataactt ttttagacga tgaatttttt   4119

taattttcgc tgtatccact gtcgtggcaa tcttcatatt gcaaaaaatg ggctatgttc   4179

aggttgccaa aaacaaatta aatcttttcc ttattgcggt cattgtggtg cggaattgca   4239

atattatgcg cagcattgtg gtaattgtct taaacaagaa ccaagttggg ataagatggt   4299

cattattggg cattatattg aacctctttc gatattgatt caccgtttta aatttcaaaa   4359
```

```
tcaattttgg attgaccgca ctttagctcg gcttttatat cttgcggtgc gtgatgctaa   4419

acgaacgcat caacttaaat tgccagaagc aatcattcca gtgcctttat atcattttcg   4479

tcagtggcga cggggttata atcaggcaga tttattatct cggcaattaa gtcgctggct   4539

ggatattcct aatttgagca atatcgtaaa gcgtgtgaaa cacacctata ctcaacgtgg   4599

tttgagtgca aaagatcgtc gtcagaattt aaaaaatgcc ttttctcttg ttgtttcgaa   4659

aaatgaattt ccttatcgcc gtgttgcgtt ggtggatgat gtgattacta ctggttctac   4719

actcaatgaa atctcaaaat tgttgcgaaa attaggtgtg gaggagattc aagtgtgggg   4779

gctggcacga gcttaatata aagcactgga aaaaaaagcg cgataagcgt attattcccg   4839

atactttctc tcaagtattt aggac                                         4864
```

```
<210> SEQ ID NO 14
<211> LENGTH: 173
<212> TYPE: PRT
<213> ORGANISM: H. influenzae

<400> SEQUENCE: 14

Met Lys Ala Phe Phe Asn Asp Pro Phe Thr Pro Phe Gly Lys Trp Leu
1               5                   10                  15

Ser Gln Pro Phe Tyr Val His Gly Leu Thr Phe Leu Leu Leu Leu Ser
            20                  25                  30

Ala Val Ile Phe Arg Pro Val Leu Asp Tyr Ile Glu Gly Ser Ser Arg
        35                  40                  45

Phe His Glu Ile Glu Asn Glu Leu Ala Val Lys Arg Ser Glu Leu Leu
    50                  55                  60

His Gln Gln Lys Ile Leu Thr Ser Leu Gln Gln Gln Ser Glu Ser Arg
65                  70                  75                  80

Lys Leu Ser Pro Glu Leu Ala Ala Gln Ile Ile Pro Leu Asn Lys Gln
                85                  90                  95

Ile Gln Arg Leu Ala Ala Arg Asn Gly Leu Ser Gln His Leu Arg Trp
            100                 105                 110

Glu Met Gly Gln Lys Pro Ile Leu His Leu Gln Leu Thr Gly His Phe
        115                 120                 125

Glu Lys Thr Lys Thr Phe Leu Thr Ala Leu Leu Ala Asn Ser Ser Gln
    130                 135                 140

Leu Ser Val Ser Arg Leu Gln Phe Ile Lys Pro Glu Asp Asn Pro Leu
145                 150                 155                 160

Gln Thr Glu Ile Ile Phe Gln Leu Asp Lys Glu Thr Lys
                165                 170
```

```
<210> SEQ ID NO 15
<211> LENGTH: 4864
<212> TYPE: DNA
<213> ORGANISM: H. influenzae
<220> FEATURE:
<221> NAME/KEY: CDS
<222> LOCATION: (2336)..(2749)

<400> SEQUENCE: 15

tacgaataat ggtttttttct ggggttaaga aaaagttacg cgctaattgt tgagtaatcg     60

tacttgcacc ttgtgatgca ccgccattac tcactgcgac aaacaatgca cgagcaatgc    120

cgatagggtc taatccgtga tgatcgtaaa aacgattgtc ttccgttgct aaaaaatgcgt   180

caattaagcg ttgtggcaca tcggctaatt tcactggaat acggcgttgc tcgcccactt    240
```

```
cgccaattaa tttaccgtca gccgtataaa tctgcattgg ttgttgtaat tcaacggttc    300

ttaatgtttc tactgagggc aattccgatt ttaggtggaa atacaacatt ccgccagcca    360

ctaaacctaa aatacataaa gttaataggg tgtttaatat taattttgcg atccgcatcg    420

taaaattctc gcttggttaa tgaatattct tgtcaagaga cctatgattt agttgttaag    480

tataaaagat tcagccttta aagaatagga aagaatatgc aattctccct gaaaaattac    540

cgcactttac aaatcggcat tcatcgtaag cagggttatt ttgattttgt gtggtttgat    600

gatcttgaac agccacaaag ttatcaaatt tttgttaatg atcgtgattt taaaaatcgt    660

tttttacaac agctaaaaac acaatatcaa gggaaaacct ttcctttaca gtttgtggca    720

agcattcccg ctcacttaac ttggtcgaaa gtattaatgt tgccacaagt gttaaatgcg    780

caagaatgtc atcaacaatg taaatttgtg attgaaaaag agctgcctat ttctttaaat    840

gaattatggt ttgattatcg ttctacctcg ttaaagcaag gttttcgatt agacgttact    900

gcaattcgta aaagtactgc tcaaacttat ttgcaagatt ttcagccatt taaaattaat    960

gtattggatg ttgcgtcaaa tgctattttg cgtgcatttc agtatttgtt gaatgaacaa   1020

gtgcggtcag aaaatacctt atttttattt caagaagatg actattgttt ggcgatctgt   1080

gaaagatcgc agcaatcgca aattttacaa tctcacgaaa atttgaccgc actttatgaa   1140

caatttaccg aacgttttga aggacaactt gaacaagttt ttgtttatca aattccctca   1200

agtcatacac cattacccga aaactggcag cgagtagaaa cagaactccc ttttattgcg   1260

cttggcaacg cgctatggca aaaagattta catcaacaaa aagtgggtgg ttaaatgtcg   1320

atgaatttat tgccttggcg tacttatcaa catcaaaagc gtttacgtcg tttagctttt   1380

tatatcgctt tatttatctt gcttgctatt aatttaatgt tggcttttag caatttgatt   1440

gaacaacaga aacaaaattt gcaagcgcag caaacatctt ttgaacaact taatcagcaa   1500

cttcacaaaa ctaccatgca aattgatcag ttacgcagtg cggtgaaagt tggtgaagtt   1560

ttgacatcta ttcccaacga gcaagtaaaa aagagtttac aacagctaag tgaattacct   1620

tttcaacaag gagaactgaa taaatttaaa caagatgcca ataacttaag tttggaaggt   1680

aacgcgcaag atcaaacaga atttgaactg attcatcaat ttttaaagaa acattttccc   1740

aatgtgaaat taagtcaggt tcaacctgaa caagatacat tgttttttca ctttgatgtg   1800

gaacaagggg cggaaaaatg aaagcttttt ttaacgatcc ttttactcct tttggaaaat   1860

ggctaagtca gcctttttat gtgcacggtt taaccttttt attgctatta agtgcggtga   1920

tttttcgccc cgttttagat tatatcgagg ggagttcacg tttccatgaa attgaaaatg   1980

agttagcggt gaaacgttca gaattgttgc atcaacagaa aattttaact tctttacagc   2040

agcagtcgga aagtcgaaaa ctttctccag aactggctgc acaaattatt cctttgaata   2100

aacaaattca acgtttagct gcgcgtaacg gtttatctca gcatttacgt tgggaaatgg   2160

ggcaaaagcc tattttgcat ttacagctta caggtcattt tgagaaaacg aagacatttt   2220

taaccgcact tttggctaat tcgtcacagc tttcagtgag tcgcttgcag tttatcaaac   2280

ccgaagacaa cccattgcaa accgagatca tttttcagct agataaggaa acaaa atg    2338
                                                             Met
                                                             1

aaa cat tgg ttt ttc ctg att ata tta ttt ttt atg aat tgc agt tgg      2386
Lys His Trp Phe Phe Leu Ile Ile Leu Phe Phe Met Asn Cys Ser Trp
            5                   10                  15

gga caa gat cct ttc gat aaa aca cag cgt aac cgt tct cag ttt gat      2434
Gly Gln Asp Pro Phe Asp Lys Thr Gln Arg Asn Arg Ser Gln Phe Asp
        20                  25                  30
```

```
aac gca caa aca gta atg gag cag aca gaa ata att tcc tca gat gta     2482
Asn Ala Gln Thr Val Met Glu Gln Thr Glu Ile Ile Ser Ser Asp Val
    35                  40                  45

cct aat aat cta tgc gga gcg gat gaa aat cgc caa gcg gct gaa att     2530
Pro Asn Asn Leu Cys Gly Ala Asp Glu Asn Arg Gln Ala Ala Glu Ile
50                  55                  60                  65

cct ttg aac gct tta aaa ttg gtg ggc gta gtg att tct aaa gat aaa     2578
Pro Leu Asn Ala Leu Lys Leu Val Gly Val Val Ile Ser Lys Asp Lys
                70                  75                  80

gcc ttt gcc ttg ttg caa gat caa ggt ttg caa att tac agc gtt tta     2626
Ala Phe Ala Leu Leu Gln Asp Gln Gly Leu Gln Ile Tyr Ser Val Leu
            85                  90                  95

gag ggc gtt gat gtg gct caa gag ggc tat att gta gaa aaa atc aac     2674
Glu Gly Val Asp Val Ala Gln Glu Gly Tyr Ile Val Glu Lys Ile Asn
        100                 105                 110

caa aac aat gtt caa ttt atg cgt aag ctc gga gag caa tgt gat agt     2722
Gln Asn Asn Val Gln Phe Met Arg Lys Leu Gly Glu Gln Cys Asp Ser
    115                 120                 125

agt gaa tgg aaa aaa tta agt ttt taa aggaagatta tgaagaaata           2769
Ser Glu Trp Lys Lys Leu Ser Phe
130                 135

tttttaaag tgcggttatt ttttagtgtg tttttgtttg ccattaatcg tttttgctaa   2829

tcctaaaaca gataacgaat gtttttttat tcgtttatcg caagcacctt tagctcaaac   2889

actggagcaa ttagcttttc aacaagatgt gaatttagtg atgggtgaga ggttagaagg   2949

caatatttct ttgaaattaa acaatattga tatgccacgt ttgctaaaaa taatcgcaaa   3009

aagtaagcat cttactttga ataaagatga tggggtttat tatttaaacg gcagtcaatc   3069

tggcaaaggt caagttgcag gaaatcttac gacaaatgaa ccgcacttag tcagccacac   3129

ggtaaaactt cattttgcta aagcctctga attaatgaaa tccttaacaa caggaagtgg   3189

atctttgctt tcttctgcgg ggagcattac ctttgatgat cgcagtaatt tgctggttat   3249

tcaggatgaa cctcgttttg tgcaaaatat caaaaaactg attgctgaaa tggataagcc   3309

tattgaacag atcgctattg aagcgcgaat tgtgacaatt acggatgaga gtttgaaaga   3369

acttggcgtt cggtgggga tttttaatcc aactgaaaat gcaagacgag ttgcgggcag   3429

ccttacaggc aatagctttg aaaatattgc ggataatctt aatgtaaatt ttgcgacaac   3489

gacgacacct gctggctcta tagcattaca agtcgcgaaa attaatgggc gattgcttga   3549

tttagaattg agtgcgttgg agcgtgaaaa taatgtagaa attattgcaa gtcctcgctt   3609

actcactacc aataagaaaa gtgcgagcat taaacagggg acagaaattc cttacatcgt   3669

gagtaatact cgtaacgata cgcaatctgt ggaatttcgt gaggcagtac ttggtttgga   3729

agtgacgcca catatttcta aagataacaa tatcttactt gatttattgg taagtcaaaa   3789

ttcccctggt tctcgtgtcg cttatggaca aaatgaggtg gtttctattg ataagcaaga   3849

aattaatact caggttttg ccaaagatgg ggaaaccatt gtgcttggcg gcgtatttca   3909

cgacacaatc acgaaaagcg aagataaagt gccattgctt ggcgatatac ccgttattaa   3969

acgattattt agcaaagaaa gtgaacgaca tcaaaaacgt gagctcgtga ttttcgtcac   4029

gccgcatatt ttaaaagcag gagaaacgtt agaggcgttg aaacaaaaaa gtgcggggaa   4089

aaaataactt ttttagacga tgaatttttt taattttcgc tgtatccact gtcgtggcaa   4149

tcttcatatt gcaaaaaatg ggctatgttc aggttgccaa aaacaaatta aatcttttcc   4209

ttattgcggt cattgtggtg cggaattgca atattatgcg cagcattgtg gtaattgtct   4269
```

```
taaacaagaa ccaagttggg ataagatggt cattattggg cattatattg aacctctttc   4329

gatattgatt caccgtttta aatttcaaaa tcaattttgg attgaccgca ctttagctcg   4389

gcttttatat cttgcggtgc gtgatgctaa acgaacgcat caacttaaat tgccagaagc   4449

aatcattcca gtgcctttat atcattttcg tcagtggcga cggggttata atcaggcaga   4509

tttattatct cggcaattaa gtcgctggct ggatattcct aatttgagca atatcgtaaa   4569

gcgtgtgaaa cacacctata ctcaacgtgg tttgagtgca aaagatcgtc gtcagaattt   4629

aaaaaatgcc ttttctcttg ttgtttcgaa aaatgaattt ccttatcgcc gtgttgcgtt   4689

ggtggatgat gtgattacta ctggttctac actcaatgaa atctcaaaat tgttgcgaaa   4749

attaggtgtg gaggagattc aagtgtgggg gctggcacga gcttaatata aagcactgga   4809

aaaaaaagcg cgataagcgt attattcccg atactttctc tcaagtattt aggac        4864


<210> SEQ ID NO 16
<211> LENGTH: 137
<212> TYPE: PRT
<213> ORGANISM: H. influenzae

<400> SEQUENCE: 16

Met Lys His Trp Phe Phe Leu Ile Ile Leu Phe Phe Met Asn Cys Ser
1               5                   10                  15

Trp Gly Gln Asp Pro Phe Asp Lys Thr Gln Arg Asn Arg Ser Gln Phe
            20                  25                  30

Asp Asn Ala Gln Thr Val Met Glu Gln Thr Glu Ile Ile Ser Ser Asp
        35                  40                  45

Val Pro Asn Asn Leu Cys Gly Ala Asp Glu Asn Arg Gln Ala Ala Glu
    50                  55                  60

Ile Pro Leu Asn Ala Leu Lys Leu Val Gly Val Val Ile Ser Lys Asp
65                  70                  75                  80

Lys Ala Phe Ala Leu Leu Gln Asp Gln Gly Leu Gln Ile Tyr Ser Val
                85                  90                  95

Leu Glu Gly Val Asp Val Ala Gln Glu Gly Tyr Ile Val Glu Lys Ile
            100                 105                 110

Asn Gln Asn Asn Val Gln Phe Met Arg Lys Leu Gly Glu Gln Cys Asp
        115                 120                 125

Ser Ser Glu Trp Lys Lys Leu Ser Phe
    130                 135


<210> SEQ ID NO 17
<211> LENGTH: 4864
<212> TYPE: DNA
<213> ORGANISM: H. influenzae
<220> FEATURE:
<221> NAME/KEY: CDS
<222> LOCATION: (2759)..(4096)

<400> SEQUENCE: 17

tacgaataat ggtttttttct ggggttaaga aaaagttacg cgctaattgt tgagtaatcg     60

tacttgcacc ttgtgatgca ccgccattac tcactgcgac aaacaatgca cgagcaatgc    120

cgatagggtc taatccgtga tgatcgtaaa aacgattgtc ttccgttgct aaaaatgcgt    180

caattaagcg ttgtggcaca tcggctaatt tcactggaat acggcgttgc tcgcccactt    240

cgccaattaa tttaccgtca gccgtataaa tctgcattgg ttgttgtaat tcaacggttc    300

ttaatgtttc tactgagggc aattccgatt ttaggtggaa atacaacatt ccgccagcca    360

ctaaacctaa aatacataaa gttaataggg tgtttaatat taattttgcg atccgcatcg    420
```

```
taaaattctc gcttggttaa tgaatattct tgtcaagaga cctatgattt agttgttaag    480
tataaaagat tcagccttta aagaatagga aagaatatgc aattctccct gaaaaattac    540
cgcactttac aaatcggcat tcatcgtaag cagggttatt ttgattttgt gtggtttgat    600
gatcttgaac agccacaaag ttatcaaatt tttgttaatg atcgtgattt taaaaatcgt    660
tttttacaac agctaaaaac acaatatcaa gggaaaacct ttcctttaca gtttgtggca    720
agcattcccg ctcacttaac ttggtcgaaa gtattaatgt tgccacaagt gttaaatgcg    780
caagaatgtc atcaacaatg taaatttgtg attgaaaaag agctgcctat ttctttaaat    840
gaattatggt ttgattatcg ttctacctcg ttaaagcaag gttttcgatt agacgttact    900
gcaattcgta aaagtactgc tcaaacttat ttgcaagatt ttcagccatt taaaattaat    960
gtattggatg ttgcgtcaaa tgctattttg cgtgcatttc agtatttgtt gaatgaacaa   1020
gtgcggtcag aaaatacctt atttttattt caagaagatg actattgttt ggcgatctgt   1080
gaaagatcgc agcaatcgca aattttacaa tctcacgaaa atttgaccgc actttatgaa   1140
caatttaccg aacgttttga aggacaactt gaacaagttt ttgtttatca aattccctca   1200
agtcatacac cattacccga aaactggcag cgagtagaaa cagaactccc ttttattgcg   1260
cttggcaacg cgctatggca aaaagattta catcaacaaa aagtgggtgg ttaaatgtcg   1320
atgaatttat tgccttggcg tacttatcaa catcaaaagc gtttacgtcg tttagctttt   1380
tatatcgctt tatttatctt gcttgctatt aatttaatgt tggcttttag caatttgatt   1440
gaacaacaga aacaaaattt gcaagcgcag caaacatctt ttgaacaact taatcagcaa   1500
cttcacaaaa ctaccatgca aattgatcag ttacgcagtg cggtgaaagt tggtgaagtt   1560
ttgacatcta ttcccaacga gcaagtaaaa aagagtttac aacagctaag tgaattacct   1620
tttcaacaag gagaactgaa taaatttaaa caagatgcca ataacttaag tttggaaggt   1680
aacgcgcaag atcaaacaga atttgaactg attcatcaat ttttaaagaa acattttccc   1740
aatgtgaaat taagtcaggt tcaacctgaa caagatacat tgtttttttca ctttgatgtg   1800
gaacaagggg cggaaaaatg aaagcttttt ttaacgatcc ttttactcct tttggaaaat   1860
ggctaagtca gcctttttat gtgcacggtt taaccttttt attgctatta agtgcggtga   1920
tttttcgccc cgttttagat tatatcgagg ggagttcacg tttccatgaa attgaaaatg   1980
agttagcggt gaaacgttca gaattgttgc atcaacagaa aattttaact tctttacagc   2040
agcagtcgga aagtcgaaaa ctttctccag aactggctgc acaaattatt cctttgaata   2100
aacaaattca acgtttagct gcgcgtaacg gtttatctca gcatttacgt tgggaaatgg   2160
ggcaaaagcc tattttgcat ttacagctta caggtcattt tgagaaaacg aagacatttt   2220
taaccgcact tttggctaat tcgtcacagc tttcagtgag tcgcttgcag tttatcaaac   2280
ccgaagacaa cccattgcaa accgagatca tttttcagct agataaggaa acaaaatgaa   2340
acattggttt ttcctgatta tattattttt tatgaattgc agttggggac aagatccttt   2400
cgataaaaca cagcgtaacc gttctcagtt tgataacgca caaacagtaa tggagcagac   2460
agaaataatt tcctcagatg tacctaataa tctatgcgga gcggatgaaa atcgccaagc   2520
ggctgaaatt cctttgaacg ctttaaaatt ggtgggcgta gtgatttcta aagataaagc   2580
ctttgccttg ttgcaagatc aaggtttgca aatttacagc gttttagagg gcgttgatgt   2640
ggctcaagag ggctatattg tagaaaaaat caaccaaaac aatgttcaat ttatgcgtaa   2700
gctcggagag caatgtgata gtagtgaatg gaaaaaatta agtttttaaa ggaagatt     2758
```

```
atg aag aaa tat ttt tta aag tgc ggt tat ttt tta gtg tgt ttt tgt      2806
Met Lys Lys Tyr Phe Leu Lys Cys Gly Tyr Phe Leu Val Cys Phe Cys
1               5                   10                  15

ttg cca tta atc gtt ttt gct aat cct aaa aca gat aac gaa tgt ttt      2854
Leu Pro Leu Ile Val Phe Ala Asn Pro Lys Thr Asp Asn Glu Cys Phe
            20                  25                  30

ttt att cgt tta tcg caa gca cct tta gct caa aca ctg gag caa tta      2902
Phe Ile Arg Leu Ser Gln Ala Pro Leu Ala Gln Thr Leu Glu Gln Leu
        35                  40                  45

gct ttt caa caa gat gtg aat tta gtg atg ggt gag agg tta gaa ggc      2950
Ala Phe Gln Gln Asp Val Asn Leu Val Met Gly Glu Arg Leu Glu Gly
    50                  55                  60

aat att tct ttg aaa tta aac aat att gat atg cca cgt ttg cta aaa      2998
Asn Ile Ser Leu Lys Leu Asn Asn Ile Asp Met Pro Arg Leu Leu Lys
65                  70                  75                  80

ata atc gca aaa agt aag cat ctt act ttg aat aaa gat gat ggg gtt      3046
Ile Ile Ala Lys Ser Lys His Leu Thr Leu Asn Lys Asp Asp Gly Val
                85                  90                  95

tat tat tta aac ggc agt caa tct ggc aaa ggt caa gtt gca gga aat      3094
Tyr Tyr Leu Asn Gly Ser Gln Ser Gly Lys Gly Gln Val Ala Gly Asn
            100                 105                 110

ctt acg aca aat gaa ccg cac tta gtc agc cac acg gta aaa ctt cat      3142
Leu Thr Thr Asn Glu Pro His Leu Val Ser His Thr Val Lys Leu His
        115                 120                 125

ttt gct aaa gcc tct gaa tta atg aaa tcc tta aca aca gga agt gga      3190
Phe Ala Lys Ala Ser Glu Leu Met Lys Ser Leu Thr Thr Gly Ser Gly
    130                 135                 140

tct ttg ctt tct tct gcg ggg agc att acc ttt gat gat cgc agt aat      3238
Ser Leu Leu Ser Ser Ala Gly Ser Ile Thr Phe Asp Asp Arg Ser Asn
145                 150                 155                 160

ttg ctg gtt att cag gat gaa cct cgt ttt gtg caa aat atc aaa aaa      3286
Leu Leu Val Ile Gln Asp Glu Pro Arg Phe Val Gln Asn Ile Lys Lys
                165                 170                 175

ctg att gct gaa atg gat aag cct att gaa cag atc gct att gaa gcg      3334
Leu Ile Ala Glu Met Asp Lys Pro Ile Glu Gln Ile Ala Ile Glu Ala
            180                 185                 190

cga att gtg aca att acg gat gag agt ttg aaa gaa ctt ggc gtt cgg      3382
Arg Ile Val Thr Ile Thr Asp Glu Ser Leu Lys Glu Leu Gly Val Arg
        195                 200                 205

tgg ggg att ttt aat cca act gaa aat gca aga cga gtt gcg ggc agc      3430
Trp Gly Ile Phe Asn Pro Thr Glu Asn Ala Arg Arg Val Ala Gly Ser
    210                 215                 220

ctt aca ggc aat agc ttt gaa aat att gcg gat aat ctt aat gta aat      3478
Leu Thr Gly Asn Ser Phe Glu Asn Ile Ala Asp Asn Leu Asn Val Asn
225                 230                 235                 240

ttt gcg aca acg acg aca cct gct ggc tct ata gca tta caa gtc gcg      3526
Phe Ala Thr Thr Thr Thr Pro Ala Gly Ser Ile Ala Leu Gln Val Ala
                245                 250                 255

aaa att aat ggg cga ttg ctt gat tta gaa ttg agt gcg ttg gag cgt      3574
Lys Ile Asn Gly Arg Leu Leu Asp Leu Glu Leu Ser Ala Leu Glu Arg
            260                 265                 270

gaa aat aat gta gaa att att gca agt cct cgc tta ctc act acc aat      3622
Glu Asn Asn Val Glu Ile Ile Ala Ser Pro Arg Leu Leu Thr Thr Asn
        275                 280                 285

aag aaa agt gcg agc att aaa cag ggg aca gaa att cct tac atc gtg      3670
Lys Lys Ser Ala Ser Ile Lys Gln Gly Thr Glu Ile Pro Tyr Ile Val
    290                 295                 300

agt aat act cgt aac gat acg caa tct gtg gaa ttt cgt gag gca gta      3718
Ser Asn Thr Arg Asn Asp Thr Gln Ser Val Glu Phe Arg Glu Ala Val
305                 310                 315                 320
```

```
ctt ggt ttg gaa gtg acg cca cat att tct aaa gat aac aat atc tta     3766
Leu Gly Leu Glu Val Thr Pro His Ile Ser Lys Asp Asn Asn Ile Leu
                325                 330                 335

ctt gat tta ttg gta agt caa aat tcc cct ggt tct cgt gtc gct tat     3814
Leu Asp Leu Leu Val Ser Gln Asn Ser Pro Gly Ser Arg Val Ala Tyr
            340                 345                 350

gga caa aat gag gtg gtt tct att gat aag caa gaa att aat act cag     3862
Gly Gln Asn Glu Val Val Ser Ile Asp Lys Gln Glu Ile Asn Thr Gln
        355                 360                 365

gtt ttt gcc aaa gat ggg gaa acc att gtg ctt ggc ggc gta ttt cac     3910
Val Phe Ala Lys Asp Gly Glu Thr Ile Val Leu Gly Gly Val Phe His
    370                 375                 380

gac aca atc acg aaa agc gaa gat aaa gtg cca ttg ctt ggc gat ata     3958
Asp Thr Ile Thr Lys Ser Glu Asp Lys Val Pro Leu Leu Gly Asp Ile
385                 390                 395                 400

ccc gtt att aaa cga tta ttt agc aaa gaa agt gaa cga cat caa aaa     4006
Pro Val Ile Lys Arg Leu Phe Ser Lys Glu Ser Glu Arg His Gln Lys
                405                 410                 415

cgt gag ctc gtg att ttc gtc acg ccg cat att tta aaa gca gga gaa     4054
Arg Glu Leu Val Ile Phe Val Thr Pro His Ile Leu Lys Ala Gly Glu
            420                 425                 430

acg tta gag gcg ttg aaa caa aaa agt gcg ggg aaa aaa taa             4096
Thr Leu Glu Ala Leu Lys Gln Lys Ser Ala Gly Lys Lys
        435                 440                 445

ctttttaga cgatgaattt ttttaatttt cgctgtatcc actgtcgtgg caatcttcat   4156

attgcaaaaa atgggctatg ttcaggttgc caaaaacaaa ttaaatcttt tccttattgc   4216

ggtcattgtg gtgcggaatt gcaatattat gcgcagcatt gtggtaattg tcttaaacaa   4276

gaaccaagtt gggataagat ggtcattatt gggcattata ttgaacctct ttcgatattg   4336

attcaccgtt ttaaatttca aaatcaattt tggattgacc gcactttagc tcggctttta   4396

tatcttgcgg tgcgtgatgc taaacgaacg catcaactta aattgccaga agcaatcatt   4456

ccagtgcctt tatatcattt tcgtcagtgg cgacggggtt ataatcaggc agatttatta   4516

tctcggcaat taagtcgctg gctggatatt cctaatttga gcaatatcgt aaagcgtgtg   4576

aaacacacct atactcaacg tggtttgagt gcaaaagatc gtcgtcagaa tttaaaaaat   4636

gcctttctc ttgttgtttc gaaaaatgaa tttccttatc gccgtgttgc gttggtggat    4696

gatgtgatta ctactggttc tacactcaat gaaatctcaa aattgttgcg aaaattaggt   4756

gtggaggaga ttcaagtgtg ggggctggca cgagcttaat ataaagcact ggaaaaaaaa   4816

gcgcgataag cgtattattc ccgatacttt ctctcaagta tttaggac                4864


<210> SEQ ID NO 18
<211> LENGTH: 445
<212> TYPE: PRT
<213> ORGANISM: H. influenzae

<400> SEQUENCE: 18

Met Lys Lys Tyr Phe Leu Lys Cys Gly Tyr Phe Leu Val Cys Phe Cys
1               5                   10                  15

Leu Pro Leu Ile Val Phe Ala Asn Pro Lys Thr Asp Asn Glu Cys Phe
            20                  25                  30

Phe Ile Arg Leu Ser Gln Ala Pro Leu Ala Gln Thr Leu Glu Gln Leu
        35                  40                  45

Ala Phe Gln Gln Asp Val Asn Leu Val Met Gly Glu Arg Leu Glu Gly
    50                  55                  60
```

```
Asn Ile Ser Leu Lys Leu Asn Asn Ile Asp Met Pro Arg Leu Leu Lys
65                  70                  75                  80

Ile Ile Ala Lys Ser Lys His Leu Thr Leu Asn Lys Asp Asp Gly Val
                85                  90                  95

Tyr Tyr Leu Asn Gly Ser Gln Ser Gly Lys Gly Gln Val Ala Gly Asn
            100                 105                 110

Leu Thr Thr Asn Glu Pro His Leu Val Ser His Thr Val Lys Leu His
        115                 120                 125

Phe Ala Lys Ala Ser Glu Leu Met Lys Ser Leu Thr Thr Gly Ser Gly
    130                 135                 140

Ser Leu Leu Ser Ser Ala Gly Ser Ile Thr Phe Asp Asp Arg Ser Asn
145                 150                 155                 160

Leu Leu Val Ile Gln Asp Glu Pro Arg Phe Val Gln Asn Ile Lys Lys
                165                 170                 175

Leu Ile Ala Glu Met Asp Lys Pro Ile Glu Gln Ile Ala Ile Glu Ala
            180                 185                 190

Arg Ile Val Thr Ile Thr Asp Glu Ser Leu Lys Glu Leu Gly Val Arg
        195                 200                 205

Trp Gly Ile Phe Asn Pro Thr Glu Asn Ala Arg Arg Val Ala Gly Ser
    210                 215                 220

Leu Thr Gly Asn Ser Phe Glu Asn Ile Ala Asp Asn Leu Asn Val Asn
225                 230                 235                 240

Phe Ala Thr Thr Thr Thr Pro Ala Gly Ser Ile Ala Leu Gln Val Ala
                245                 250                 255

Lys Ile Asn Gly Arg Leu Leu Asp Leu Glu Leu Ser Ala Leu Glu Arg
            260                 265                 270

Glu Asn Asn Val Glu Ile Ile Ala Ser Pro Arg Leu Leu Thr Thr Asn
        275                 280                 285

Lys Lys Ser Ala Ser Ile Lys Gln Gly Thr Glu Ile Pro Tyr Ile Val
    290                 295                 300

Ser Asn Thr Arg Asn Asp Thr Gln Ser Val Glu Phe Arg Glu Ala Val
305                 310                 315                 320

Leu Gly Leu Glu Val Thr Pro His Ile Ser Lys Asp Asn Asn Ile Leu
                325                 330                 335

Leu Asp Leu Leu Val Ser Gln Asn Ser Pro Gly Ser Arg Val Ala Tyr
            340                 345                 350

Gly Gln Asn Glu Val Val Ser Ile Asp Lys Gln Glu Ile Asn Thr Gln
        355                 360                 365

Val Phe Ala Lys Asp Gly Glu Thr Ile Val Leu Gly Gly Val Phe His
    370                 375                 380

Asp Thr Ile Thr Lys Ser Glu Asp Lys Val Pro Leu Leu Gly Asp Ile
385                 390                 395                 400

Pro Val Ile Lys Arg Leu Phe Ser Lys Glu Ser Glu Arg His Gln Lys
                405                 410                 415

Arg Glu Leu Val Ile Phe Val Thr Pro His Ile Leu Lys Ala Gly Glu
            420                 425                 430

Thr Leu Glu Ala Leu Lys Gln Lys Ser Ala Gly Lys Lys
        435                 440                 445
```

<210> SEQ ID NO 19
<211> LENGTH: 4864
<212> TYPE: DNA
<213> ORGANISM: H. influenzae
<220> FEATURE:
<221> NAME/KEY: CDS

<222> LOCATION: (4109)..(4795)

<400> SEQUENCE: 19

```
tacgaataat ggttttttct ggggttaaga aaaagttacg cgctaattgt tgagtaatcg     60
tacttgcacc ttgtgatgca ccgccattac tcactgcgac aaacaatgca cgagcaatgc    120
cgatagggtc taatccgtga tgatcgtaaa aacgattgtc ttccgttgct aaaaatgcgt    180
caattaagcg ttgtggcaca tcggctaatt tcactggaat acggcgttgc tcgcccactt    240
cgccaattaa tttaccgtca gccgtataaa tctgcattgg ttgttgtaat tcaacggttc    300
ttaatgtttc tactgagggc aattccgatt ttaggtggaa atacaacatt ccgccagcca    360
ctaaacctaa aatacataaa gttaataggg tgtttaatat taattttgcg atccgcatcg    420
taaaattctc gcttggttaa tgaatattct tgtcaagaga cctatgattt agttgttaag    480
tataaaagat tcagccttta aagaatagga aagaatatgc aattctccct gaaaaattac    540
cgcactttac aaatcggcat tcatcgtaag cagggttatt ttgattttgt gtggtttgat    600
gatcttgaac agccacaaag ttatcaaatt tttgttaatg atcgtgattt taaaaatcgt    660
tttttacaac agctaaaaac acaatatcaa gggaaaacct ttcctttaca gtttgtggca    720
agcattcccg ctcacttaac ttggtcgaaa gtattaatgt tgccacaagt gttaaatgcg    780
caagaatgtc atcaacaatg taaatttgtg attgaaaaag agctgcctat ttctttaaat    840
gaattatggt ttgattatcg ttctacctcg ttaaagcaag gttttcgatt agacgttact    900
gcaattcgta aaagtactgc tcaaacttat ttgcaagatt ttcagccatt taaaattaat    960
gtattggatg ttgcgtcaaa tgctattttg cgtgcatttc agtatttgtt gaatgaacaa   1020
gtgcggtcag aaaatacctt atttttattt caagaagatg actattgttt ggcgatctgt   1080
gaaagatcgc agcaatcgca aattttacaa tctcacgaaa atttgaccgc actttatgaa   1140
caatttaccg aacgttttga aggacaactt gaacaagttt ttgtttatca aattccctca   1200
agtcatacac cattacccga aaactggcag cgagtagaaa cagaactccc ttttattgcg   1260
cttggcaacg cgctatggca aaaagattta catcaacaaa aagtgggtgg ttaaatgtcg   1320
atgaatttat tgccttggcg tacttatcaa catcaaaagc gtttacgtcg tttagctttt   1380
tatatcgctt tatttatctt gcttgctatt aatttaatgt tggcttttag caatttgatt   1440
gaacaacaga aacaaaattt gcaagcgcag caaacatctt ttgaacaact taatcagcaa   1500
cttcacaaaa ctaccatgca aattgatcag ttacgcagtg cggtgaaagt tggtgaagtt   1560
ttgacatcta ttcccaacga gcaagtaaaa aagagtttac aacagctaag tgaattacct   1620
tttcaacaag gagaactgaa taaatttaaa caagatgcca ataacttaag tttggaaggt   1680
aacgcgcaag atcaaacaga atttgaactg attcatcaat ttttaaagaa acattttccc   1740
aatgtgaaat taagtcaggt tcaacctgaa caagatacat tgttttttca ctttgatgtg   1800
gaacaagggg cggaaaaatg aaagcttttt ttaacgatcc ttttactcct tttggaaaat   1860
ggctaagtca gccttttat gtgcacggtt taaccttttt attgctatta agtgcggtga    1920
tttttcgccc cgttttagat tatatcgagg ggagttcacg tttccatgaa attgaaaatg   1980
agttagcggt gaaacgttca gaattgttgc atcaacagaa aattttaact tctttacagc   2040
agcagtcgga aagtcgaaaa ctttctccag aactggctgc acaaattatt cctttgaata   2100
aacaaattca acgtttagct gcgcgtaacg gtttatctca gcatttacgt tgggaaatgg   2160
ggcaaaagcc tattttgcat ttacagctta caggtcattt tgagaaaacg aagacatttt   2220
taaccgcact tttggctaat tcgtcacagc tttcagtgag tcgcttgcag tttatcaaac   2280
```

-continued

```
ccgaagacaa cccattgcaa accgagatca tttttcagct agataaggaa acaaaatgaa   2340

acattggttt ttcctgatta tattattttt tatgaattgc agttggggac aagatccttt   2400

cgataaaaca cagcgtaacc gttctcagtt tgataacgca caaacagtaa tggagcagac   2460

agaaataatt tcctcagatg tacctaataa tctatgcgga gcggatgaaa atcgccaagc   2520

ggctgaaatt cctttgaacg ctttaaaatt ggtgggcgta gtgatttcta aagataaagc   2580

ctttgccttg ttgcaagatc aaggtttgca aatttacagc gttttagagg gcgttgatgt   2640

ggctcaagag ggctatattg tagaaaaaat caaccaaaac aatgttcaat ttatgcgtaa   2700

gctcggagag caatgtgata gtagtgaatg gaaaaaatta agtttttaaa ggaagattat   2760

gaagaaatat tttttaaagt gcggttattt tttagtgtgt ttttgtttgc cattaatcgt   2820

ttttgctaat cctaaaacag ataacgaatg tttttttatt cgtttatcgc aagcaccttt   2880

agctcaaaca ctggagcaat tagcttttca acaagatgtg aatttagtga tgggtgagag   2940

gttagaaggc aatatttctt tgaaattaaa caatattgat atgccacgtt tgctaaaaat   3000

aatcgcaaaa agtaagcatc ttactttgaa taaagatgat ggggtttatt atttaaacgg   3060

cagtcaatct ggcaaaggtc aagttgcagg aaatcttacg acaaatgaac cgcacttagt   3120

cagccacacg gtaaaacttc attttgctaa agcctctgaa ttaatgaaat ccttaacaac   3180

aggaagtgga tctttgcttt cttctgcggg gagcattacc tttgatgatc gcagtaattt   3240

gctggttatt caggatgaac ctcgttttgt gcaaaatatc aaaaaactga ttgctgaaat   3300

ggataagcct attgaacaga tcgctattga agcgcgaatt gtgacaatta cggatgagag   3360

tttgaaagaa cttggcgttc ggtgggggat tttaatccaa actgaaaatg caagacgagt   3420

tgcgggcagc cttacaggca atagctttga aaatattgcg gataatctta atgtaaattt   3480

tgcgacaacg acgacacctg ctggctctat agcattacaa gtcgcgaaaa ttaatgggcg   3540

attgcttgat ttagaattga gtgcgttgga gcgtgaaaat aatgtagaaa ttattgcaag   3600

tcctcgctta ctcactacca ataagaaaag tgcgagcatt aaacagggga cagaaattcc   3660

ttacatcgtg agtaatactc gtaacgatac gcaatctgtg gaatttcgtg aggcagtact   3720

tggtttggaa gtgacgccac atatttctaa agataacaat atcttacttg atttattggt   3780

aagtcaaaat tcccctggtt ctcgtgtcgc ttatggacaa aatgaggtgg tttctattga   3840

taagcaagaa attaatactc aggtttttgc caaagatggg gaaaccattg tgcttggcgg   3900

cgtatttcac gacacaatca cgaaaagcga agataaagtg ccattgcttg gcgatatacc   3960

cgttattaaa cgattattta gcaaagaaag tgaacgacat caaaaacgtg agctcgtgat   4020

tttcgtcacg ccgcatattt taaaagcagg agaaacgtta gaggcgttga aacaaaaaag   4080

tgcggggaaa aaataacttt tttagacg atg aat ttt ttt aat ttt cgc tgt      4132
                               Met Asn Phe Phe Asn Phe Arg Cys
                               1               5

atc cac tgt cgt ggc aat ctt cat att gca aaa aat ggg cta tgt tca     4180
Ile His Cys Arg Gly Asn Leu His Ile Ala Lys Asn Gly Leu Cys Ser
    10                  15                  20

ggt tgc caa aaa caa att aaa tct ttt cct tat tgc ggt cat tgt ggt     4228
Gly Cys Gln Lys Gln Ile Lys Ser Phe Pro Tyr Cys Gly His Cys Gly
25                  30                  35                  40

gcg gaa ttg caa tat tat gcg cag cat tgt ggt aat tgt ctt aaa caa     4276
Ala Glu Leu Gln Tyr Tyr Ala Gln His Cys Gly Asn Cys Leu Lys Gln
                45                  50                  55

gaa cca agt tgg gat aag atg gtc att att ggg cat tat att gaa cct     4324
Glu Pro Ser Trp Asp Lys Met Val Ile Ile Gly His Tyr Ile Glu Pro
```

```
            60                  65                  70

ctt tcg ata ttg att cac cgt ttt aaa ttt caa aat caa ttt tgg att      4372
Leu Ser Ile Leu Ile His Arg Phe Lys Phe Gln Asn Gln Phe Trp Ile
        75                  80                  85

gac cgc act tta gct cgg ctt tta tat ctt gcg gtg cgt gat gct aaa      4420
Asp Arg Thr Leu Ala Arg Leu Leu Tyr Leu Ala Val Arg Asp Ala Lys
    90                  95                  100

cga acg cat caa ctt aaa ttg cca gaa gca atc att cca gtg cct tta      4468
Arg Thr His Gln Leu Lys Leu Pro Glu Ala Ile Ile Pro Val Pro Leu
105                 110                 115                 120

tat cat ttt cgt cag tgg cga cgg ggt tat aat cag gca gat tta tta      4516
Tyr His Phe Arg Gln Trp Arg Arg Gly Tyr Asn Gln Ala Asp Leu Leu
                125                 130                 135

tct cgg caa tta agt cgc tgg ctg gat att cct aat ttg agc aat atc      4564
Ser Arg Gln Leu Ser Arg Trp Leu Asp Ile Pro Asn Leu Ser Asn Ile
            140                 145                 150

gta aag cgt gtg aaa cac acc tat act caa cgt ggt ttg agt gca aaa      4612
Val Lys Arg Val Lys His Thr Tyr Thr Gln Arg Gly Leu Ser Ala Lys
        155                 160                 165

gat cgt cgt cag aat tta aaa aat gcc ttt tct ctt gtt gtt tcg aaa      4660
Asp Arg Arg Gln Asn Leu Lys Asn Ala Phe Ser Leu Val Val Ser Lys
    170                 175                 180

aat gaa ttt cct tat cgc cgt gtt gcg ttg gtg gat gat gtg att act      4708
Asn Glu Phe Pro Tyr Arg Arg Val Ala Leu Val Asp Asp Val Ile Thr
185                 190                 195                 200

act ggt tct aca ctc aat gaa atc tca aaa ttg ttg cga aaa tta ggt      4756
Thr Gly Ser Thr Leu Asn Glu Ile Ser Lys Leu Leu Arg Lys Leu Gly
                205                 210                 215

gtg gag gag att caa gtg tgg ggg ctg gca cga gct taa tataaagcac       4805
Val Glu Glu Ile Gln Val Trp Gly Leu Ala Arg Ala
            220                 225

tggaaaaaaa agcgcgataa gcgtattatt cccgatactt tctctcaagt atttaggac     4864


<210> SEQ ID NO 20
<211> LENGTH: 228
<212> TYPE: PRT
<213> ORGANISM: H. influenzae

<400> SEQUENCE: 20

Met Asn Phe Phe Asn Phe Arg Cys Ile His Cys Arg Gly Asn Leu His
1               5                   10                  15

Ile Ala Lys Asn Gly Leu Cys Ser Gly Cys Gln Lys Gln Ile Lys Ser
            20                  25                  30

Phe Pro Tyr Cys Gly His Cys Gly Ala Glu Leu Gln Tyr Tyr Ala Gln
        35                  40                  45

His Cys Gly Asn Cys Leu Lys Gln Glu Pro Ser Trp Asp Lys Met Val
    50                  55                  60

Ile Ile Gly His Tyr Ile Glu Pro Leu Ser Ile Leu Ile His Arg Phe
65                  70                  75                  80

Lys Phe Gln Asn Gln Phe Trp Ile Asp Arg Thr Leu Ala Arg Leu Leu
                85                  90                  95

Tyr Leu Ala Val Arg Asp Ala Lys Arg Thr His Gln Leu Lys Leu Pro
            100                 105                 110

Glu Ala Ile Ile Pro Val Pro Leu Tyr His Phe Arg Gln Trp Arg Arg
        115                 120                 125

Gly Tyr Asn Gln Ala Asp Leu Leu Ser Arg Gln Leu Ser Arg Trp Leu
    130                 135                 140
```

```
Asp Ile Pro Asn Leu Ser Asn Ile Val Lys Arg Val Lys His Thr Tyr
145                 150                 155                 160

Thr Gln Arg Gly Leu Ser Ala Lys Asp Arg Arg Gln Asn Leu Lys Asn
                165                 170                 175

Ala Phe Ser Leu Val Val Ser Lys Asn Glu Phe Pro Tyr Arg Arg Val
            180                 185                 190

Ala Leu Val Asp Asp Val Ile Thr Thr Gly Ser Thr Leu Asn Glu Ile
        195                 200                 205

Ser Lys Leu Leu Arg Lys Leu Gly Val Glu Glu Ile Gln Val Trp Gly
    210                 215                 220

Leu Ala Arg Ala
225


<210> SEQ ID NO 21
<211> LENGTH: 677
<212> TYPE: DNA
<213> ORGANISM: H. influenzae
<220> FEATURE:
<221> NAME/KEY: CDS
<222> LOCATION: (73)..(612)

<400> SEQUENCE: 21

tcacatgccc tatgttttca tacaaattaa agcatattaa atatttcgac tgcccctgtt      60

aaaaggagaa aa atg caa aca ata agt aaa caa cta agt gcg gtt att ttc     111
              Met Gln Thr Ile Ser Lys Gln Leu Ser Ala Val Ile Phe
              1               5                   10

cct ttc att ttt tct gcc tgc gtt tca caa tct gcg tct agc tta gat       159
Pro Phe Ile Phe Ser Ala Cys Val Ser Gln Ser Ala Ser Ser Leu Asp
    15                  20                  25

cat caa gct gcc gcc aaa gcg cga gtg gaa ctc gct ttg agc tat ctt       207
His Gln Ala Ala Ala Lys Ala Arg Val Glu Leu Ala Leu Ser Tyr Leu
30                  35                  40                  45

cag caa aat aat cct caa ctg gct aaa atc aat tta gac aaa gca ctt       255
Gln Gln Asn Asn Pro Gln Leu Ala Lys Ile Asn Leu Asp Lys Ala Leu
                50                  55                  60

caa cac gat aaa aat tac tat ctc gta cat tca gca ctt gca cat tat       303
Gln His Asp Lys Asn Tyr Tyr Leu Val His Ser Ala Leu Ala His Tyr
            65                  70                  75

tat caa caa caa ggg caa ata gaa aat gcc ttt cgt gag tat gaa ata       351
Tyr Gln Gln Gln Gly Gln Ile Glu Asn Ala Phe Arg Glu Tyr Glu Ile
        80                  85                  90

gcc gta aaa ctt aat cat aaa caa ggc gat gta cat aat aat ttt ggt       399
Ala Val Lys Leu Asn His Lys Gln Gly Asp Val His Asn Asn Phe Gly
    95                  100                 105

acg ttt cta tgt agt caa aag aaa ttt gag caa gcc cag caa caa ttt       447
Thr Phe Leu Cys Ser Gln Lys Lys Phe Glu Gln Ala Gln Gln Gln Phe
110                 115                 120                 125

gaa tta gcc ctt aat tcg ccg aat tat tat cat caa gca gat aca ttt       495
Glu Leu Ala Leu Asn Ser Pro Asn Tyr Tyr His Gln Ala Asp Thr Phe
                130                 135                 140

gaa aat atc gcg ctt tgt gct tat tcc gcg aaa aaa atg gat att tat       543
Glu Asn Ile Ala Leu Cys Ala Tyr Ser Ala Lys Lys Met Asp Ile Tyr
            145                 150                 155

cag caa aca tta gaa aaa tta cgt caa atc aat gga aaa cgt gcg gaa       591
Gln Gln Thr Leu Glu Lys Leu Arg Gln Ile Asn Gly Lys Arg Ala Glu
        160                 165                 170

aaa ttc aat agt cta aaa taa agcattgcca aatcaagtat tggactttaa          642
Lys Phe Asn Ser Leu Lys
    175
```

```
aatttagccc ttatttaccg cctaattatt tgatt                              677


<210> SEQ ID NO 22
<211> LENGTH: 179
<212> TYPE: PRT
<213> ORGANISM: H. influenzae

<400> SEQUENCE: 22

Met Gln Thr Ile Ser Lys Gln Leu Ser Ala Val Ile Phe Pro Phe Ile
1               5                   10                  15

Phe Ser Ala Cys Val Ser Gln Ser Ala Ser Ser Leu Asp His Gln Ala
            20                  25                  30

Ala Ala Lys Ala Arg Val Glu Leu Ala Leu Ser Tyr Leu Gln Gln Asn
        35                  40                  45

Asn Pro Gln Leu Ala Lys Ile Asn Leu Asp Lys Ala Leu Gln His Asp
    50                  55                  60

Lys Asn Tyr Tyr Leu Val His Ser Ala Leu Ala His Tyr Tyr Gln Gln
65                  70                  75                  80

Gln Gly Gln Ile Glu Asn Ala Phe Arg Glu Tyr Glu Ile Ala Val Lys
                85                  90                  95

Leu Asn His Lys Gln Gly Asp Val His Asn Asn Phe Gly Thr Phe Leu
            100                 105                 110

Cys Ser Gln Lys Lys Phe Glu Gln Ala Gln Gln Gln Phe Glu Leu Ala
        115                 120                 125

Leu Asn Ser Pro Asn Tyr Tyr His Gln Ala Asp Thr Phe Glu Asn Ile
    130                 135                 140

Ala Leu Cys Ala Tyr Ser Ala Lys Lys Met Asp Ile Tyr Gln Gln Thr
145                 150                 155                 160

Leu Glu Lys Leu Arg Gln Ile Asn Gly Lys Arg Ala Glu Lys Phe Asn
                165                 170                 175

Ser Leu Lys


<210> SEQ ID NO 23
<211> LENGTH: 19
<212> TYPE: DNA
<213> ORGANISM: Artificial sequence
<220> FEATURE:
<223> OTHER INFORMATION: Synthetic primer

<400> SEQUENCE: 23

tgtgacactt ccgcaaaaa                                                 19


<210> SEQ ID NO 24
<211> LENGTH: 21
<212> TYPE: DNA
<213> ORGANISM: Artificial sequence
<220> FEATURE:
<223> OTHER INFORMATION: Synthetic primer

<400> SEQUENCE: 24

taataaaagg aaaatgaatg a                                              21


<210> SEQ ID NO 25
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 25
```

```
atg aaa tta aca aca cag caa acc ttg aaa aaa ggg ttt aca tta ata      48
Met Lys Leu Thr Thr Gln Gln Thr Leu Lys Lys Gly Phe Thr Leu Ile
1               5                   10                  15

gag cta atg att gtg att gca att att gct att tta gcc act atc gca      96
Glu Leu Met Ile Val Ile Ala Ile Ile Ala Ile Leu Ala Thr Ile Ala
            20                  25                  30

att ccc tct tat caa aat tat act aaa aaa gca gcg gta tct gaa tta     144
Ile Pro Ser Tyr Gln Asn Tyr Thr Lys Lys Ala Ala Val Ser Glu Leu
        35                  40                  45

ctg caa gcg tca gcg cct tat aag gct gat gtg gaa tta tgt gta tat     192
Leu Gln Ala Ser Ala Pro Tyr Lys Ala Asp Val Glu Leu Cys Val Tyr
    50                  55                  60

agc aca aat gaa aca aca aac tgt acg ggt gga aaa aat ggt att gca     240
Ser Thr Asn Glu Thr Thr Asn Cys Thr Gly Gly Lys Asn Gly Ile Ala
65                  70                  75                  80

gca gat ata acc aca gca aaa ggc tat gta aaa tca gtg aca aca agc     288
Ala Asp Ile Thr Thr Ala Lys Gly Tyr Val Lys Ser Val Thr Thr Ser
                85                  90                  95

aac ggt gca ata aca gta aaa ggg gat ggc aca ttg gca aat atg gaa     336
Asn Gly Ala Ile Thr Val Lys Gly Asp Gly Thr Leu Ala Asn Met Glu
            100                 105                 110

tat att ttg caa gct aca ggt aat gct gca aca ggt gta act tgg aca     384
Tyr Ile Leu Gln Ala Thr Gly Asn Ala Ala Thr Gly Val Thr Trp Thr
        115                 120                 125

aca act tgc aaa gga acg gat gcc tct tta ttt cca gca aat ttt tgc     432
Thr Thr Cys Lys Gly Thr Asp Ala Ser Leu Phe Pro Ala Asn Phe Cys
    130                 135                 140

gga agt gtc aca caa                                                 447
Gly Ser Val Thr Gln
145
```

<210> SEQ ID NO 26
<211> LENGTH: 149
<212> TYPE: PRT
<213> ORGANISM: H. influenzae

<400> SEQUENCE: 26

```
Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145
```

```
<210> SEQ ID NO 27
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 27

atg aaa tta aca aca cag caa acc ttg aaa aaa ggg ttt aca tta ata       48
Met Lys Leu Thr Thr Gln Gln Thr Leu Lys Lys Gly Phe Thr Leu Ile
1               5                   10                  15

gag cta atg att gtg att gca att att gct att tta gcc act atc gca       96
Glu Leu Met Ile Val Ile Ala Ile Ile Ala Ile Leu Ala Thr Ile Ala
            20                  25                  30

att ccc tct tat caa aat tat act aaa aaa gca gcg gta tct gaa tta      144
Ile Pro Ser Tyr Gln Asn Tyr Thr Lys Lys Ala Ala Val Ser Glu Leu
        35                  40                  45

ctg caa gcg tca gcg cct tat aag gct gat gtg gaa tta tgt gta tat      192
Leu Gln Ala Ser Ala Pro Tyr Lys Ala Asp Val Glu Leu Cys Val Tyr
    50                  55                  60

agc aca aat gaa aca aca aac tgt acg ggt gga aaa aat ggt att gca      240
Ser Thr Asn Glu Thr Thr Asn Cys Thr Gly Gly Lys Asn Gly Ile Ala
65                  70                  75                  80

gca gat ata acc aca gca aaa ggc tat gta aaa tca gtg aca aca agc      288
Ala Asp Ile Thr Thr Ala Lys Gly Tyr Val Lys Ser Val Thr Thr Ser
                85                  90                  95

aac ggt gca ata aca gta aaa ggg gat ggc aca ttg gca aat atg gaa      336
Asn Gly Ala Ile Thr Val Lys Gly Asp Gly Thr Leu Ala Asn Met Glu
            100                 105                 110

tat att ttg caa gct aca ggt aat gct gca aca ggt gta act tgg aca      384
Tyr Ile Leu Gln Ala Thr Gly Asn Ala Ala Thr Gly Val Thr Trp Thr
        115                 120                 125

aca act tgc aaa gga acg gat gcc tct tta ttt cca gca aat ttt tgc      432
Thr Thr Cys Lys Gly Thr Asp Ala Ser Leu Phe Pro Ala Asn Phe Cys
    130                 135                 140

gga agt gtc aca caa                                                  447
Gly Ser Val Thr Gln
145


<210> SEQ ID NO 28
<211> LENGTH: 149
<212> TYPE: PRT
<213> ORGANISM: H. influenzae

<400> SEQUENCE: 28

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110
```

```
Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145


<210> SEQ ID NO 29
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 29

atg aaa tta aca aca cag caa acc ttg aaa aaa ggg ttt aca tta ata       48
Met Lys Leu Thr Thr Gln Gln Thr Leu Lys Lys Gly Phe Thr Leu Ile
1               5                   10                  15

gag cta atg att gtg att gca att att gct att tta gcc act atc gca       96
Glu Leu Met Ile Val Ile Ala Ile Ile Ala Ile Leu Ala Thr Ile Ala
            20                  25                  30

att ccc tct tat caa aat tat act aaa aaa gca gcg gta tct gaa tta      144
Ile Pro Ser Tyr Gln Asn Tyr Thr Lys Lys Ala Ala Val Ser Glu Leu
        35                  40                  45

ctg caa gcg tca gcg cct tat aag gct gat gtg gaa tta tgt gta tat      192
Leu Gln Ala Ser Ala Pro Tyr Lys Ala Asp Val Glu Leu Cys Val Tyr
    50                  55                  60

agc aca aat gaa aca aca aac tgt acg ggt gga aaa aat ggt att gca      240
Ser Thr Asn Glu Thr Thr Asn Cys Thr Gly Gly Lys Asn Gly Ile Ala
65                  70                  75                  80

gca gat ata acc aca gca aaa ggc tat gta aaa tca gtg aca aca agc      288
Ala Asp Ile Thr Thr Ala Lys Gly Tyr Val Lys Ser Val Thr Thr Ser
                85                  90                  95

aac ggt gca ata aca gta aaa ggg gat ggc aca ttg gca aat atg gaa      336
Asn Gly Ala Ile Thr Val Lys Gly Asp Gly Thr Leu Ala Asn Met Glu
            100                 105                 110

tat att ttg caa gct aca ggt aat gct gca aca ggt gta act tgg aca      384
Tyr Ile Leu Gln Ala Thr Gly Asn Ala Ala Thr Gly Val Thr Trp Thr
        115                 120                 125

aca act tgc aaa gga acg gat gcc tct tta ttt cca gca aat ttt tgc      432
Thr Thr Cys Lys Gly Thr Asp Ala Ser Leu Phe Pro Ala Asn Phe Cys
    130                 135                 140

gga agt gtc aca caa                                                  447
Gly Ser Val Thr Gln
145


<210> SEQ ID NO 30
<211> LENGTH: 149
<212> TYPE: PRT
<213> ORGANISM: H. influenzae

<400> SEQUENCE: 30

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
```

```
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145


<210> SEQ ID NO 31
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 31

atg aaa tta aca aca cag caa acc ttg aaa aaa ggg ttt aca tta ata       48
Met Lys Leu Thr Thr Gln Gln Thr Leu Lys Lys Gly Phe Thr Leu Ile
1               5                   10                  15

gag cta atg att gtg att gca att att gct att tta gcc act atc gca       96
Glu Leu Met Ile Val Ile Ala Ile Ile Ala Ile Leu Ala Thr Ile Ala
            20                  25                  30

att ccc tct tat caa aat tat act aaa aaa gca gcg gta tct gaa tta      144
Ile Pro Ser Tyr Gln Asn Tyr Thr Lys Lys Ala Ala Val Ser Glu Leu
        35                  40                  45

ctg caa gcg tca gcg cct tat aag gct gat gtg gaa tta tgt gta tat      192
Leu Gln Ala Ser Ala Pro Tyr Lys Ala Asp Val Glu Leu Cys Val Tyr
    50                  55                  60

agc aca aat gaa aca aca aac tgt acg ggt gga aaa aat ggt att gca      240
Ser Thr Asn Glu Thr Thr Asn Cys Thr Gly Gly Lys Asn Gly Ile Ala
65                  70                  75                  80

gca gat ata acc aca gca aaa ggc tat gta aaa tca gtg aca aca agc      288
Ala Asp Ile Thr Thr Ala Lys Gly Tyr Val Lys Ser Val Thr Thr Ser
                85                  90                  95

aac ggt gca ata aca gta aaa ggg gat ggc aca ttg gca aat atg gaa      336
Asn Gly Ala Ile Thr Val Lys Gly Asp Gly Thr Leu Ala Asn Met Glu
            100                 105                 110

tat att ttg caa gct aca ggt aat gct gca aca ggt gta act tgg aca      384
Tyr Ile Leu Gln Ala Thr Gly Asn Ala Ala Thr Gly Val Thr Trp Thr
        115                 120                 125

aca act tgc aaa gga acg gat gcc tct tta ttt cca gca aat ttt tgc      432
Thr Thr Cys Lys Gly Thr Asp Ala Ser Leu Phe Pro Ala Asn Phe Cys
    130                 135                 140

gga agt gtc aca caa                                                  447
Gly Ser Val Thr Gln
145


<210> SEQ ID NO 32
<211> LENGTH: 149
<212> TYPE: PRT
<213> ORGANISM: H. influenzae

<400> SEQUENCE: 32
```

```
Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145


<210> SEQ ID NO 33
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 33

atg aaa tta aca aca cag caa acc ttg aaa aaa ggt ttt aca tta atc       48
Met Lys Leu Thr Thr Gln Gln Thr Leu Lys Lys Gly Phe Thr Leu Ile
1               5                   10                  15

gag cta atg att gtg att gca att att gct att tta gcc act atc gca       96
Glu Leu Met Ile Val Ile Ala Ile Ile Ala Ile Leu Ala Thr Ile Ala
            20                  25                  30

att cct tct tat caa aat tat acc aaa aaa gct tcg gta tcc gaa tta      144
Ile Pro Ser Tyr Gln Asn Tyr Thr Lys Lys Ala Ser Val Ser Glu Leu
        35                  40                  45

ctg caa gca tct gca cct tat aag gct gat gtg gaa tta tgt gta tat      192
Leu Gln Ala Ser Ala Pro Tyr Lys Ala Asp Val Glu Leu Cys Val Tyr
    50                  55                  60

agc aca aat gaa aca aca aac tgt acg ggt gga aaa aat ggt att gca      240
Ser Thr Asn Glu Thr Thr Asn Cys Thr Gly Gly Lys Asn Gly Ile Ala
65                  70                  75                  80

gct gat att aca aca gca aaa ggc tat gta gcc tca gtg aaa act caa      288
Ala Asp Ile Thr Thr Ala Lys Gly Tyr Val Ala Ser Val Lys Thr Gln
                85                  90                  95

tcg ggt ggc att aca gta aaa ggg aat ggc aca ttg gca aat atg gaa      336
Ser Gly Gly Ile Thr Val Lys Gly Asn Gly Thr Leu Ala Asn Met Glu
            100                 105                 110

tat att ttg caa gct aaa ggt aat gct aca gca ggt gta act tgg aca      384
Tyr Ile Leu Gln Ala Lys Gly Asn Ala Thr Ala Gly Val Thr Trp Thr
        115                 120                 125

aca acc tgc aaa gga acg gat gcc tct tta ttt cca gca aat ttt tgc      432
Thr Thr Cys Lys Gly Thr Asp Ala Ser Leu Phe Pro Ala Asn Phe Cys
    130                 135                 140

aga agt gtc aca aaa                                                  447
Arg Ser Val Thr Lys
```

145

<210> SEQ ID NO 34
<211> LENGTH: 149
<212> TYPE: PRT
<213> ORGANISM: H. influenzae

<400> SEQUENCE: 34

```
Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ser Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Arg Ser Val Thr Lys
145
```

<210> SEQ ID NO 35
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 35

```
atg aaa tta aca aca cag caa acc ttg aaa aaa ggg ttt aca tta ata       48
Met Lys Leu Thr Thr Gln Gln Thr Leu Lys Lys Gly Phe Thr Leu Ile
1               5                   10                  15

gag cta atg att gtg att gca att att gct att tta gcc acc atc gca       96
Glu Leu Met Ile Val Ile Ala Ile Ile Ala Ile Leu Ala Thr Ile Ala
            20                  25                  30

att cct tct tat aaa aat tat act aaa aaa gca gcg gta tct gaa tta      144
Ile Pro Ser Tyr Lys Asn Tyr Thr Lys Lys Ala Ala Val Ser Glu Leu
        35                  40                  45

ctg caa gct tct gcg cct tat aag gct gat gtg gaa tta tgt gta tat      192
Leu Gln Ala Ser Ala Pro Tyr Lys Ala Asp Val Glu Leu Cys Val Tyr
    50                  55                  60

agc aca aat gaa ata aca aat tgt atg ggt gga aaa aat ggt att gca      240
Ser Thr Asn Glu Ile Thr Asn Cys Met Gly Gly Lys Asn Gly Ile Ala
65                  70                  75                  80

gct gat att aca aca gca aaa ggc tat gta gcc tca gtg aaa act caa      288
Ala Asp Ile Thr Thr Ala Lys Gly Tyr Val Ala Ser Val Lys Thr Gln
                85                  90                  95

tcg ggt ggc att acc gta aaa ggg gat ggc aca ttg gca aat atg gaa      336
Ser Gly Gly Ile Thr Val Lys Gly Asp Gly Thr Leu Ala Asn Met Glu
            100                 105                 110
```

```
tat att ttg caa gct aca ggt aat gct gca gca ggt gta act tgg aca      384
Tyr Ile Leu Gln Ala Thr Gly Asn Ala Ala Ala Gly Val Thr Trp Thr
        115                 120                 125

aca acc tgc aaa gga acg gat gcc tct tta ttt cca gca aat ttt tgc      432
Thr Thr Cys Lys Gly Thr Asp Ala Ser Leu Phe Pro Ala Asn Phe Cys
    130                 135                 140

gga agt atc aca caa                                                  447
Gly Ser Ile Thr Gln
145


<210> SEQ ID NO 36
<211> LENGTH: 149
<212> TYPE: PRT
<213> ORGANISM: H. influenzae

<400> SEQUENCE: 36

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Lys Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Ile Thr Asn Cys Met Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Ala Gly Val Thr Trp Thr
        115                 120                 125

Thr Thr Cys Lys Gly Thr Asp Ala Ser Leu Phe Pro Ala Asn Phe Cys
    130                 135                 140

Gly Ser Ile Thr Gln
145


<210> SEQ ID NO 37
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 37

atg aaa tta aca aca ctg caa acc ttg aaa aaa ggg ttt aca tta atc       48
Met Lys Leu Thr Thr Leu Gln Thr Leu Lys Lys Gly Phe Thr Leu Ile
1               5                   10                  15

gag cta atg att gtg att gca att att gct att tta gcc act atc gca       96
Glu Leu Met Ile Val Ile Ala Ile Ile Ala Ile Leu Ala Thr Ile Ala
            20                  25                  30

att cct tct tat caa aat tat acc aaa aaa gct gcg gta tcc gaa tta      144
Ile Pro Ser Tyr Gln Asn Tyr Thr Lys Lys Ala Ala Val Ser Glu Leu
        35                  40                  45

ctg caa gct tct gcg cct tat aag gct gat gtg gaa tta tgc gtt tat      192
Leu Gln Ala Ser Ala Pro Tyr Lys Ala Asp Val Glu Leu Cys Val Tyr
    50                  55                  60

agc aca ggc aaa cct tct act tgc tca gga gga agc aat gga att gca      240
Ser Thr Gly Lys Pro Ser Thr Cys Ser Gly Gly Ser Asn Gly Ile Ala
```

```
65                  70                  75                  80

gct gat att acg aca gca aaa ggc tat gta gcc tca gtg aaa act caa      288
Ala Asp Ile Thr Thr Ala Lys Gly Tyr Val Ala Ser Val Lys Thr Gln
                85                  90                  95

tca ggt ggt att aca gta aaa ggg aat ggc aca ttg gca aat atg gaa      336
Ser Gly Gly Ile Thr Val Lys Gly Asn Gly Thr Leu Ala Asn Met Glu
            100                 105                 110

tat att ttg caa gct aca ggt aat gct gca aca ggt gta act tgg aca      384
Tyr Ile Leu Gln Ala Thr Gly Asn Ala Ala Thr Gly Val Thr Trp Thr
        115                 120                 125

aca act tgc aaa gga acg gat gcc tct tta ttt cca gca aat ttt tgc      432
Thr Thr Cys Lys Gly Thr Asp Ala Ser Leu Phe Pro Ala Asn Phe Cys
    130                 135                 140

gga agt gtc aca caa                                                  447
Gly Ser Val Thr Gln
145


<210> SEQ ID NO 38
<211> LENGTH: 149
<212> TYPE: PRT
<213> ORGANISM: H. influenzae

<400> SEQUENCE: 38

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145


<210> SEQ ID NO 39
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 39

atg aaa tta aca aca ctg caa acc ttg aaa aaa ggg ttt aca tta atc       48
Met Lys Leu Thr Thr Leu Gln Thr Leu Lys Lys Gly Phe Thr Leu Ile
1               5                   10                  15

gag cta atg att gtg att gca att att gct att tta gcc act atc gca       96
Glu Leu Met Ile Val Ile Ala Ile Ile Ala Ile Leu Ala Thr Ile Ala
            20                  25                  30
```

```
att cct tct tat caa aat tat acc aaa aaa gct gcg gta tcc gaa tta      144
Ile Pro Ser Tyr Gln Asn Tyr Thr Lys Lys Ala Ala Val Ser Glu Leu
        35                  40                  45

ctg caa gct tct gcg cct tat aag gct gat gtg gaa tta tgc gtt tat      192
Leu Gln Ala Ser Ala Pro Tyr Lys Ala Asp Val Glu Leu Cys Val Tyr
    50                  55                  60

agc aca ggc aaa ctt tct act tgc tca gga gga agc aat gga att gca      240
Ser Thr Gly Lys Leu Ser Thr Cys Ser Gly Gly Ser Asn Gly Ile Ala
65                  70                  75                  80

gct gat att aca aca gca aaa ggc tat gta gcc tca gtg aaa act caa      288
Ala Asp Ile Thr Thr Ala Lys Gly Tyr Val Ala Ser Val Lys Thr Gln
                85                  90                  95

tca ggt ggt att aca gta aaa ggg aat ggc aca ttg gca aat atg gaa      336
Ser Gly Gly Ile Thr Val Lys Gly Asn Gly Thr Leu Ala Asn Met Glu
            100                 105                 110

tat att ttg caa gct aaa ggt aat gct aca gca ggt gta act tgg aca      384
Tyr Ile Leu Gln Ala Lys Gly Asn Ala Thr Ala Gly Val Thr Trp Thr
        115                 120                 125

aca acc tgc aaa gga acg gat gcc tct tta ttt cca gca aat ttt tgc      432
Thr Thr Cys Lys Gly Thr Asp Ala Ser Leu Phe Pro Ala Asn Phe Cys
    130                 135                 140

gga agt gtc aca aaa                                                  447
Gly Ser Val Thr Lys
145


<210> SEQ ID NO 40
<211> LENGTH: 149
<212> TYPE: PRT
<213> ORGANISM: H. influenzae

<400> SEQUENCE: 40

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Leu Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Lys
145


<210> SEQ ID NO 41
<211> LENGTH: 447
<212> TYPE: DNA
<213> ORGANISM: H. influenzae
<220> FEATURE:
<221> NAME/KEY: CDS
<222> LOCATION: (1)..(447)
```

<400> SEQUENCE: 41

```
atg aaa tta aca aca cag caa acc ttg aaa aaa ggt ttt aca tta atc       48
Met Lys Leu Thr Thr Gln Gln Thr Leu Lys Lys Gly Phe Thr Leu Ile
1               5                   10                  15

gag cta atg att gtg att gca att att gct att tta gcc act atc gca       96
Glu Leu Met Ile Val Ile Ala Ile Ile Ala Ile Leu Ala Thr Ile Ala
            20                  25                  30

att cct tct tat caa aat tat acc aaa aaa gct tcg gta tcc gaa tta      144
Ile Pro Ser Tyr Gln Asn Tyr Thr Lys Lys Ala Ser Val Ser Glu Leu
        35                  40                  45

ctg caa gct tcc gca cct tat aag tca gat gtg gaa tta tgc gtt tat      192
Leu Gln Ala Ser Ala Pro Tyr Lys Ser Asp Val Glu Leu Cys Val Tyr
    50                  55                  60

agc aca ggc aaa cct tct act tgc tca gga gga agc aat gga att gca      240
Ser Thr Gly Lys Pro Ser Thr Cys Ser Gly Gly Ser Asn Gly Ile Ala
65                  70                  75                  80

gct gat att aca aca gca aaa ggc tat gta gcc tca gtg aaa act caa      288
Ala Asp Ile Thr Thr Ala Lys Gly Tyr Val Ala Ser Val Lys Thr Gln
                85                  90                  95

tca ggt ggt att aca gta aaa ggg aat ggc aca ttg gca aat atg gaa      336
Ser Gly Gly Ile Thr Val Lys Gly Asn Gly Thr Leu Ala Asn Met Glu
            100                 105                 110

tat att ttg caa gct aaa ggt aat gct aca gca ggt gta act tgg aca      384
Tyr Ile Leu Gln Ala Lys Gly Asn Ala Thr Ala Gly Val Thr Trp Thr
        115                 120                 125

aca acc tgc aaa gga acg gat gcc tct tta ttt cca gca aat ttt tgc      432
Thr Thr Cys Lys Gly Thr Asp Ala Ser Leu Phe Pro Ala Asn Phe Cys
    130                 135                 140

aga agt gtc aca aaa                                                  447
Arg Ser Val Thr Lys
145
```

<210> SEQ ID NO 42
<211> LENGTH: 149
<212> TYPE: PRT
<213> ORGANISM: H. influenzae

<400> SEQUENCE: 42

```
Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ser Val Ser Glu Leu
        35                  40                  45

Leu Gln Ala Ser Ala Pro Tyr Lys Ser Asp Val Glu Leu Cys Val Tyr
    50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Arg Ser Val Thr Lys
145
```

<210> SEQ ID NO 43
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 43

```
atg aaa tta aca aca cag caa acc ttg aaa aaa ggg ttt aca tta ata       48
Met Lys Leu Thr Thr Gln Gln Thr Leu Lys Lys Gly Phe Thr Leu Ile
1               5                   10                  15

gag cta atg att gtg att gca att att gct att tta gcc act atc gca       96
Glu Leu Met Ile Val Ile Ala Ile Ile Ala Ile Leu Ala Thr Ile Ala
            20                  25                  30

att ccc tct tat caa aat tat act aaa aaa gcg gcg gta tct gaa tta      144
Ile Pro Ser Tyr Gln Asn Tyr Thr Lys Lys Ala Ala Val Ser Glu Leu
        35                  40                  45

ctg caa gcg tca gcg cct tat aag gct gat gtg gaa tta tgt gta tat      192
Leu Gln Ala Ser Ala Pro Tyr Lys Ala Asp Val Glu Leu Cys Val Tyr
    50                  55                  60

agt aca ggt aaa cct tcc agt tgc tcg gga gga agc aat gga att gcg      240
Ser Thr Gly Lys Pro Ser Ser Cys Ser Gly Gly Ser Asn Gly Ile Ala
65                  70                  75                  80

gct gat att aca aca gca aaa ggc tat gta aaa tca gtg aca aca agc      288
Ala Asp Ile Thr Thr Ala Lys Gly Tyr Val Lys Ser Val Thr Thr Ser
                85                  90                  95

aac ggt gca ata aca gta aaa ggg gat ggc aca ttg gca aat atg gaa      336
Asn Gly Ala Ile Thr Val Lys Gly Asp Gly Thr Leu Ala Asn Met Glu
            100                 105                 110

tat att ttg caa gcc agt ggt aat gct gca aca ggt gta act tgg aca      384
Tyr Ile Leu Gln Ala Ser Gly Asn Ala Ala Thr Gly Val Thr Trp Thr
        115                 120                 125

aca act tgc aaa gga acg gat gcc tct tta ttt cca gca aat ttt tgc      432
Thr Thr Cys Lys Gly Thr Asp Ala Ser Leu Phe Pro Ala Asn Phe Cys
    130                 135                 140

gga agt gtc aca caa                                                  447
Gly Ser Val Thr Gln
145
```

<210> SEQ ID NO 44
<211> LENGTH: 149
<212> TYPE: PRT
<213> ORGANISM: H. influenzae

<400> SEQUENCE: 44

```
Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Ser Cys Ser Gly Gly Ser Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
```

```
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145


<210> SEQ ID NO 45
<211> LENGTH: 15
<212> TYPE: PRT
<213> ORGANISM: Haemophilus influenzae

<400> SEQUENCE: 45

Phe Thr Leu Ile Glu Leu Met Ile Val Ile Ala Ile Ile Ala Ile
1               5                   10                  15


<210> SEQ ID NO 46
<211> LENGTH: 15
<212> TYPE: PRT
<213> ORGANISM: Haemophilus influenzae

<400> SEQUENCE: 46

Ala Ile Ile Ala Ile Leu Ala Thr Ile Ala Ile Pro Ser Tyr Gln
1               5                   10                  15


<210> SEQ ID NO 47
<211> LENGTH: 15
<212> TYPE: PRT
<213> ORGANISM: Haemophilus influenzae

<400> SEQUENCE: 47

Ile Pro Ser Tyr Gln Asn Tyr Thr Lys Lys Ala Ala Val Ser Glu
1               5                   10                  15


<210> SEQ ID NO 48
<211> LENGTH: 15
<212> TYPE: PRT
<213> ORGANISM: Haemophilus influenzae

<400> SEQUENCE: 48

Ala Ala Val Ser Glu Leu Leu Gln Ala Ser Ala Pro Tyr Lys Ala
1               5                   10                  15


<210> SEQ ID NO 49
<211> LENGTH: 15
<212> TYPE: PRT
<213> ORGANISM: Haemophilus influenzae

<400> SEQUENCE: 49

Ala Pro Tyr Lys Ala Asp Val Glu Leu Cys Val Tyr Ser Thr Asn
1               5                   10                  15


<210> SEQ ID NO 50
<211> LENGTH: 15
<212> TYPE: PRT
<213> ORGANISM: Haemophilus influenzae

<400> SEQUENCE: 50

Val Tyr Ser Thr Asn Glu Thr Thr Asn Cys Thr Gly Gly Lys Asn
1               5                   10                  15


<210> SEQ ID NO 51
```

<211> LENGTH: 15
<212> TYPE: PRT
<213> ORGANISM: Haemophilus influenzae

<400> SEQUENCE: 51

Val Tyr Ser Thr Gly Lys Pro Ser Thr Cys Ser Gly Gly Ser Asn
1 5 10 15

<210> SEQ ID NO 52
<211> LENGTH: 15
<212> TYPE: PRT
<213> ORGANISM: Haemophilus influenzae

<400> SEQUENCE: 52

Thr Gly Gly Lys Asn Gly Ile Ala Ala Asp Ile Thr Thr Ala Lys
1 5 10 15

<210> SEQ ID NO 53
<211> LENGTH: 15
<212> TYPE: PRT
<213> ORGANISM: Haemophilus influenzae

<400> SEQUENCE: 53

Ile Thr Thr Ala Lys Gly Tyr Val Lys Ser Val Thr Thr Ser Asn
1 5 10 15

<210> SEQ ID NO 54
<211> LENGTH: 19
<212> TYPE: PRT
<213> ORGANISM: Haemophilus influenzae

<400> SEQUENCE: 54

Tyr Val Lys Ser Val Thr Thr Ser Asn Gly Ala Ile Thr Val Lys Gly
1 5 10 15

Asp Gly Thr

<210> SEQ ID NO 55
<211> LENGTH: 19
<212> TYPE: PRT
<213> ORGANISM: Haemophilus influenzae

<400> SEQUENCE: 55

Tyr Val Ala Ser Val Lys Thr Gln Ser Gly Gly Ile Thr Val Lys Gly
1 5 10 15

Asn Gly Thr

<210> SEQ ID NO 56
<211> LENGTH: 15
<212> TYPE: PRT
<213> ORGANISM: Haemophilus influenzae

<400> SEQUENCE: 56

Lys Gly Asp Gly Thr Leu Ala Asn Met Glu Tyr Ile Leu Gln Ala
1 5 10 15

<210> SEQ ID NO 57
<211> LENGTH: 15
<212> TYPE: PRT
<213> ORGANISM: Haemophilus influenzae

<400> SEQUENCE: 57

Tyr Ile Leu Gln Ala Thr Gly Asn Ala Ala Thr Gly Val Thr Trp
1 5 10 15

```
<210> SEQ ID NO 58
<211> LENGTH: 15
<212> TYPE: PRT
<213> ORGANISM: Haemophilus influenzae

<400> SEQUENCE: 58

Thr Gly Val Thr Trp Thr Thr Thr Cys Lys Gly Thr Asp Ala Ser
1               5                   10                  15


<210> SEQ ID NO 59
<211> LENGTH: 17
<212> TYPE: PRT
<213> ORGANISM: Haemophilus influenzae

<400> SEQUENCE: 59

Gly Thr Asp Ala Ser Leu Phe Pro Ala Asn Phe Cys Gly Ser Val Thr
1               5                   10                  15

Gln
```